US011040083B2

(12) United States Patent
Tran Van Nhieu et al.

(10) Patent No.: US 11,040,083 B2
(45) Date of Patent: Jun. 22, 2021

(54) POLYPEPTIDES COMPRISING VINCULIN BINDING SITES FOR THE TREATMENT OF PROLIFERATION AND/OR ADHESION RELATED DISEASES

(71) Applicants: PARIS SCIENCES ET LETTRES—QUARTIER LATIN, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR)

(72) Inventors: Guy Tran Van Nhieu, Orsay (FR); Cesar Valencia-Gallardo, Paris (FR); Nicole Quenech'Du, Paris (FR)

(73) Assignees: PARIS SCIENCES ET LETTRES—QUARTER LATIN, Paris (FR); CENTRE NATIONAL DE LA RECHERCHE SCIENTIFIQUE, Paris (FR); INSERM (INSTITUT NATIONAL DE LA SANTÉ ET DE AL RECHERCHE MÉDICALE), Paris (FR)

( * ) Notice: Subject to any disclaimer, the term of this patent is extended or adjusted under 35 U.S.C. 154(b) by 27 days.

(21) Appl. No.: 15/764,621

(22) PCT Filed: Sep. 29, 2016

(86) PCT No.: PCT/EP2016/073287
§ 371 (c)(1),
(2) Date: Mar. 29, 2018

(87) PCT Pub. No.: WO2017/055467
PCT Pub. Date: Apr. 6, 2017

(65) Prior Publication Data
US 2018/0264072 A1 Sep. 20, 2018

(30) Foreign Application Priority Data
Sep. 29, 2015 (EP) .................................... 15187486

(51) Int. Cl.
*C07K 14/25* (2006.01)
*C07K 4/04* (2006.01)
*A61K 38/06* (2006.01)
*A61P 35/04* (2006.01)
*A61K 48/00* (2006.01)

(52) U.S. Cl.
CPC ............ *A61K 38/06* (2013.01); *A61K 48/005* (2013.01); *A61P 35/04* (2018.01); *C07K 14/25* (2013.01)

(58) Field of Classification Search
None
See application file for complete search history.

(56) References Cited

U.S. PATENT DOCUMENTS

| 5,262,165 A | 11/1993 | Govil et al. |
| 5,948,433 A | 9/1999 | Burton et al. |
| 6,010,715 A | 1/2000 | Wick et al. |
| 6,071,531 A | 6/2000 | Jona et al. |

FOREIGN PATENT DOCUMENTS

NO    2014/042828 A2    3/2014

OTHER PUBLICATIONS

Park et al., "Novel Vinculin Binding Site of the IpaA Invasin of Shigella," J. Biol. Chem. 286:23214-23221, Suppl. Methods, pp. 1-7 (2011) (Year: 2011).*
Bourdet-Sicard et al., "Binding of theShigella protein IpaA to vinculin induces F-actin depolymerisation," Embo J. 18:5853-5862 (1999) (Year: 1999).*
S. flexneri Invasin Ipa (UniProtKB Accession No. P18010, accessed Jan. 20, 2020 at URL: uniprot.org/uniprot/P18010, pp. 1-6. Sequence entered Nov. 1, 1990. (Year: 1990).*
Invasin IpaA domain protein (UniProtKB Accession No. F5P4G8_SHIFL, accessed Jan. 20, 2020 at URL: uniprot.org/uniprot/ F5P4G8, pp. 1-3; sequence was entered Jul. 27, 2011 (Year: 2011).*
Yampolsky et al., "The Exchangeability of Amino Acids in Proteins," Genetics 170: 1459-1472 (2005) (Year: 2005).*
Anonymous, "EM_STD:AY206439", XP055237584, Oct. 23, 2003, retrieved on Dec. 18, 2015 (cited in ISR).
Borgon et al., "Crystal Structure of Human Vinculin", Structure, 2004, pp. 1189-1197, vol. 12, No. 7.
Nelson et al., "Vinculin activators target integrins from within the cell to increase melanoma sensitivity to chemotherapy", Molecular Cancer Research, 2011, pp. 712-723, vol. 9, No. 6.
Orchard et al., "Mimicking GEFs: a common theme for bacterial pathogens", Cellular Microbiology, 2012, pp. 10-18, vol. 14, No. 1.
Izard et al., "Shigella applies molecular mimicry to subvert vinculin and invade host cells", The Journal of Cell Biology, 2006, pp. 465-475, vol. 175, No. 3.
Tran Van Nhieu et al. "Vinculin binding in its closed conformation by a helix addition mechanism", The EMBO Journal, 2007, pp. 4588-4596, vol. 26, No. 21.
Park et al., "Rho-associated Kinase Connects a Cell Cycle-controlling Anchorage Signal to the Mammalian Target of Rapamycin Pathway", The Journal of Biological Chemistry, 2011, pp. 23132-23141, vol. 286, No. 26.
Devereux et al., "A comprehensive set of sequence analysis programs for the VAX", Nucleic Acids Research, 1984, pp. 387-395, vol. 12, No. 1.
Ramarao et al., "Capping of actin filaments by vinculin activated by the Shigella IpaA carboxyl-terminal domain", FEBS Letters, 2007, pp. 853-857, vol. 581, No. 5.
Papagrigoriou et al., "Activation of a vinculin-binding site in the talin rod involves rearrangement of a five-helix bundle", The EMBO Journal, 2004, pp. 2942-2951, vol. 23, No. 15.

(Continued)

*Primary Examiner* — Julie Ha
*Assistant Examiner* — Kristina M Hellman
(74) *Attorney, Agent, or Firm* — Nixon & Vanderhye

(57) ABSTRACT

Disclosed are polypeptides including at least one vinculin binding sites, to nucleic acid sequences encoding thereof and to their use for treating a proliferation and/or adhesion related disease.

2 Claims, 25 Drawing Sheets

Specification includes a Sequence Listing.

(56) References Cited

OTHER PUBLICATIONS

Tran Van Nhieu et al., "Modulation of bacterial entry into epithelial cells by association between vinculin and the Shigella IpaA invasin", The EMBO Journal, 1997, pp. 2717-2729, vol. 16, No. 10.
Gingras et al., "Mapping and Consensus Sequence Identification for Multiple Vinculin Binding Sites within the Talin Rod", The Journal of Biological Chemistry, 2005, pp. 37217-37224, vol. 280, No. 44.
Park et al., "Novel Vinculin Binding Site of the IpaA Invasin of Shigella", The Journal of Biological Chemistry, 2011, pp. 23214-23221, vol. 286, No. 26.
Anonymous, "UPI00069AA064", XP055237548, Aug. 22, 2015, retrieved on Dec. 18, 2015, http://www.uniprot.org/uniparc/UPI00069AA064.
Anonymous, "UPI00069B6C94", XP055237551, Aug. 22, 2015, retrieved on Dec. 18, 2015, http://www.uniprot.org/uniparc/UPI00069B6C94.
Anonymous, "UPI000326416B", XP055237552, Mar. 19, 2013, retrieved on Dec. 18, 2015, http://www.uniprot.org/uniparc/UPI000326416B.
International Search Report, dated Nov. 30, 2016, from corresponding PCT application No. PCT/EP2016/073287.
Database UniProt—B3X7C6 (B3X7C6_9ENTR), Sep. 23, 2008, Retrieved from https://www.uniprot.org/uniprot/B3X7C6.

* cited by examiner

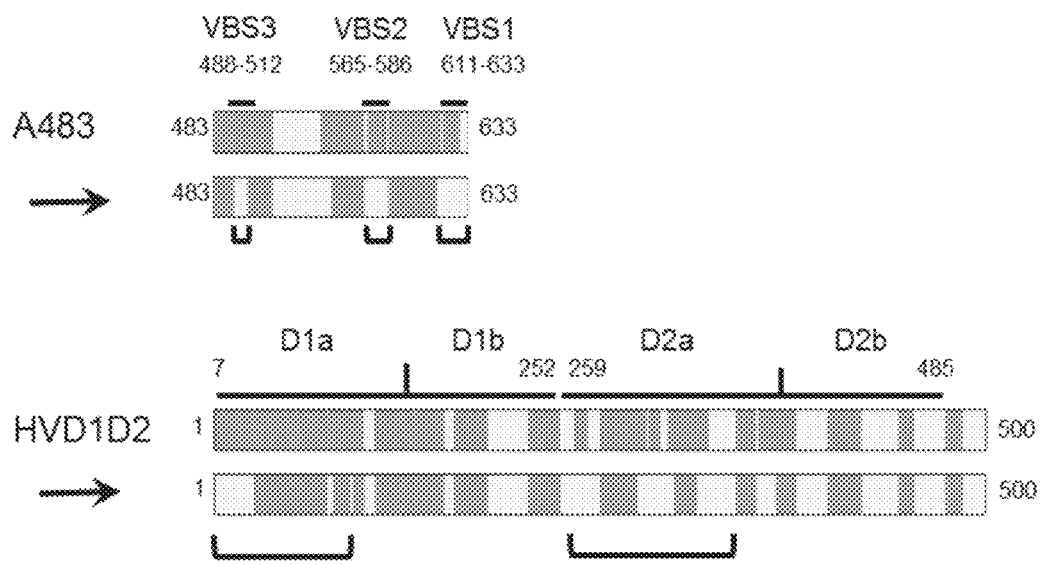
FIG. 3
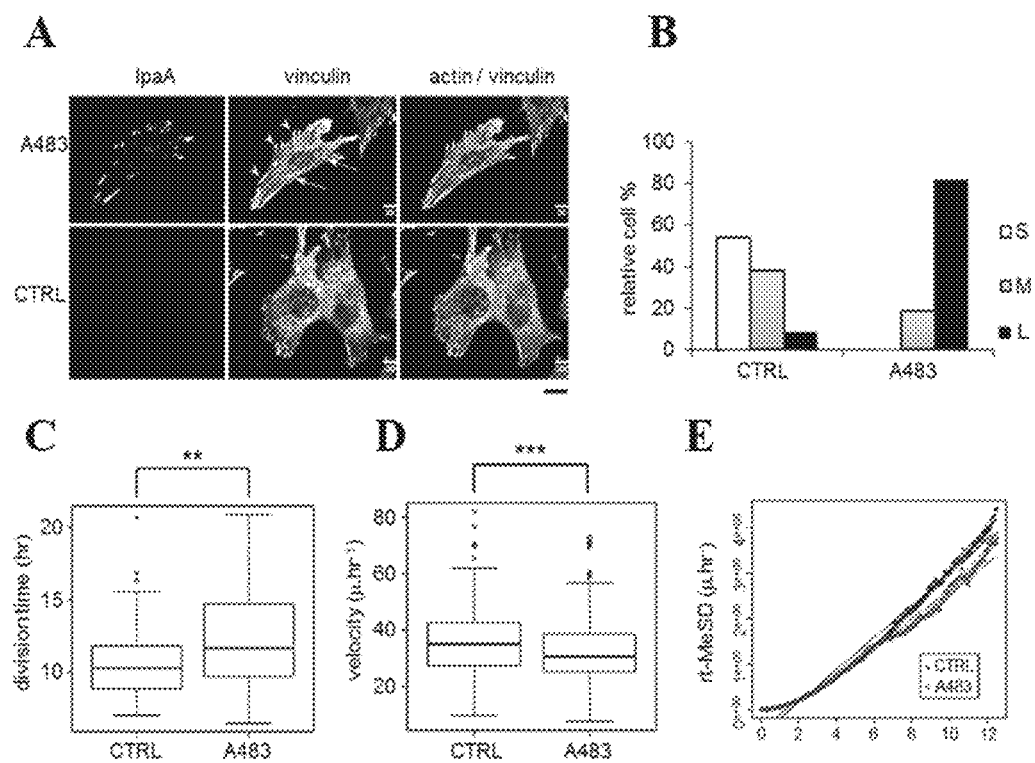
FIG. 4A-E

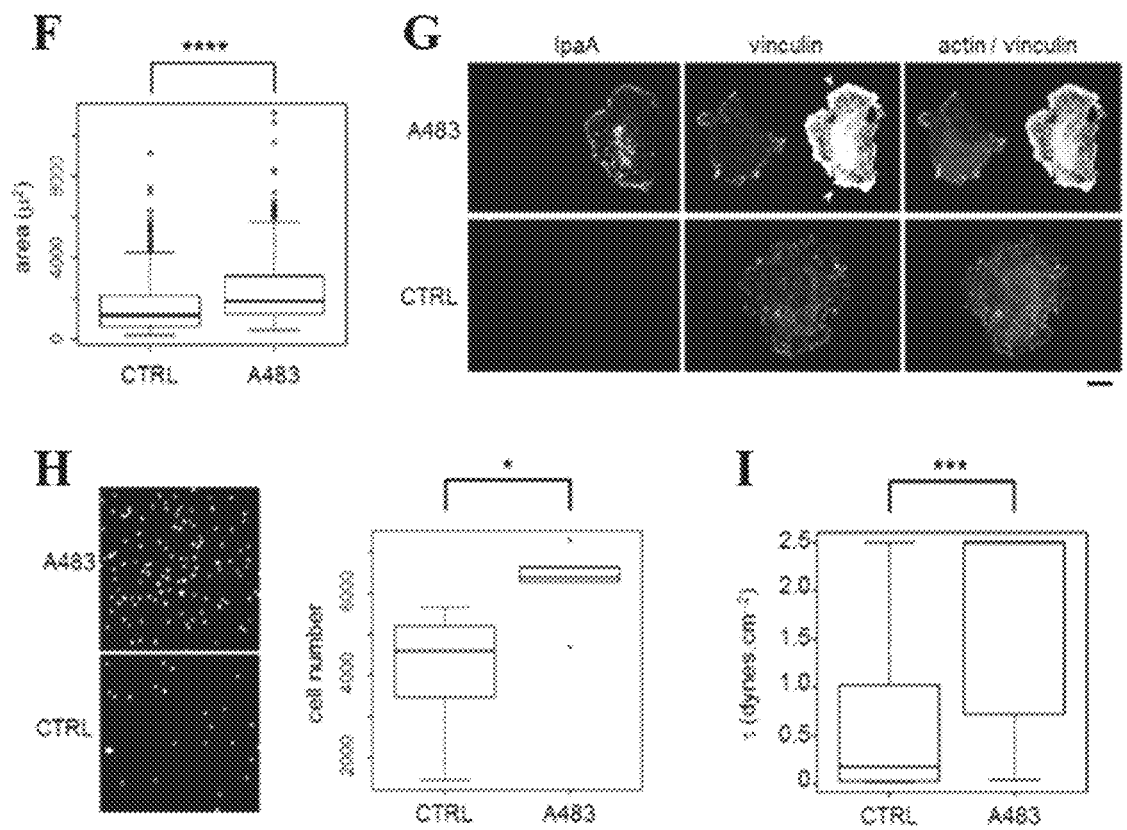
FIG. 4F-I
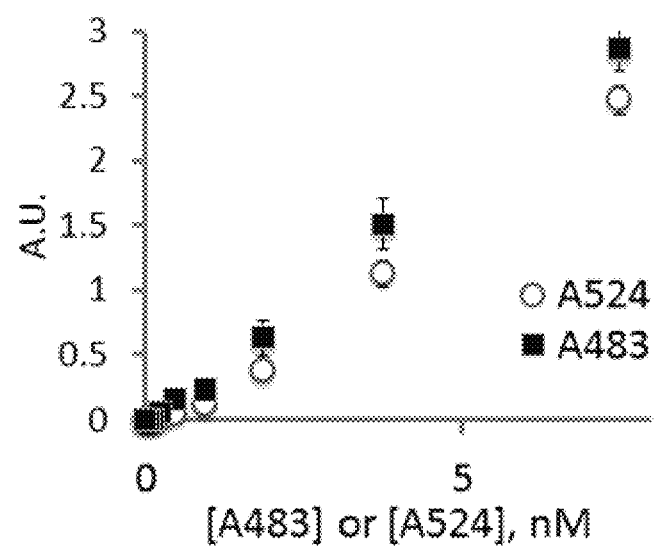
FIG. 5

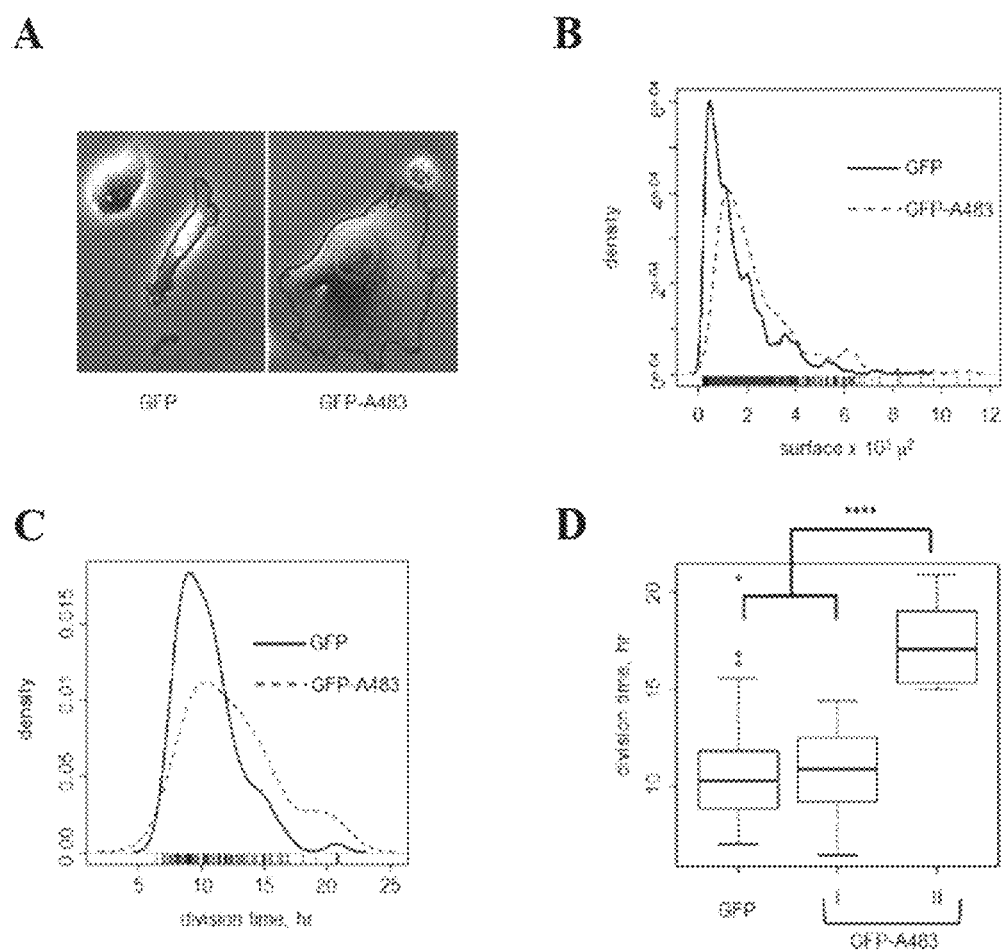
FIG. 7A-D

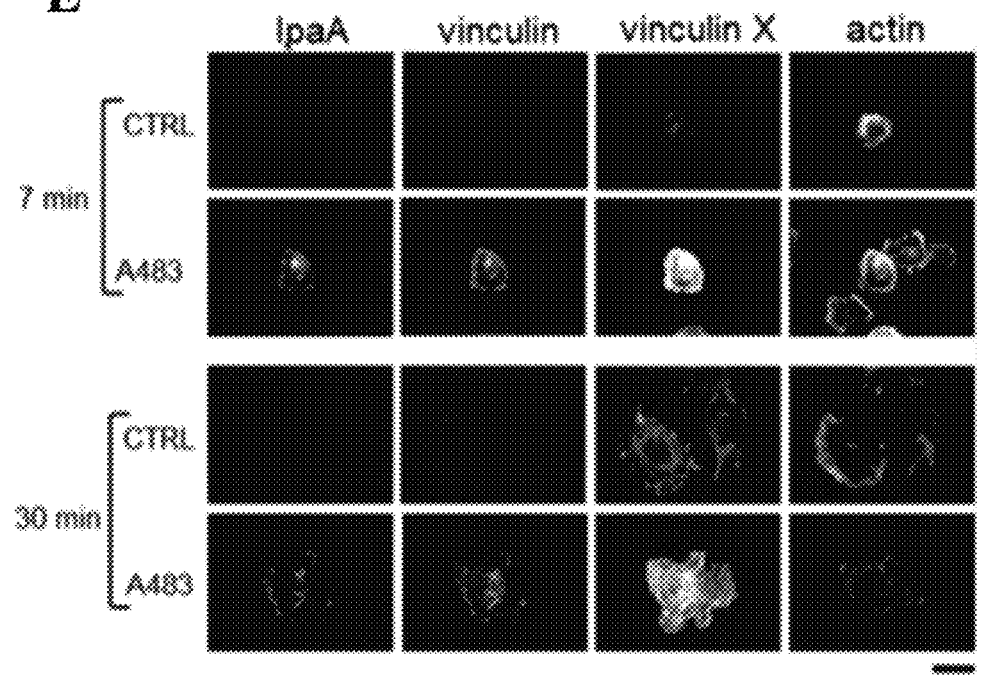
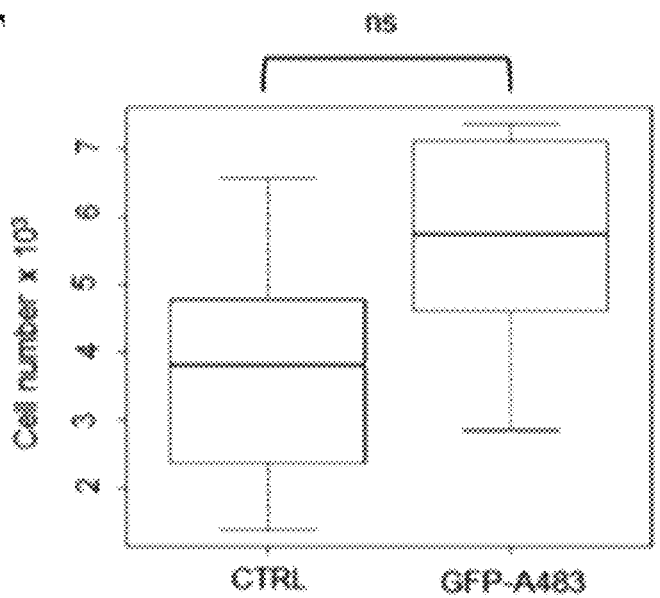
FIG. 7E-F

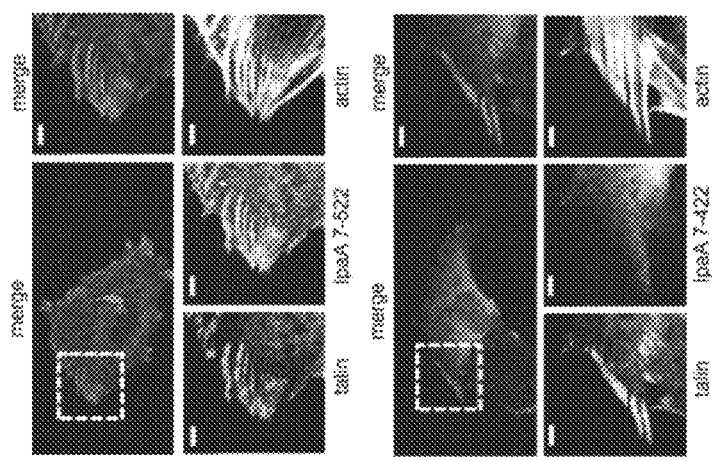
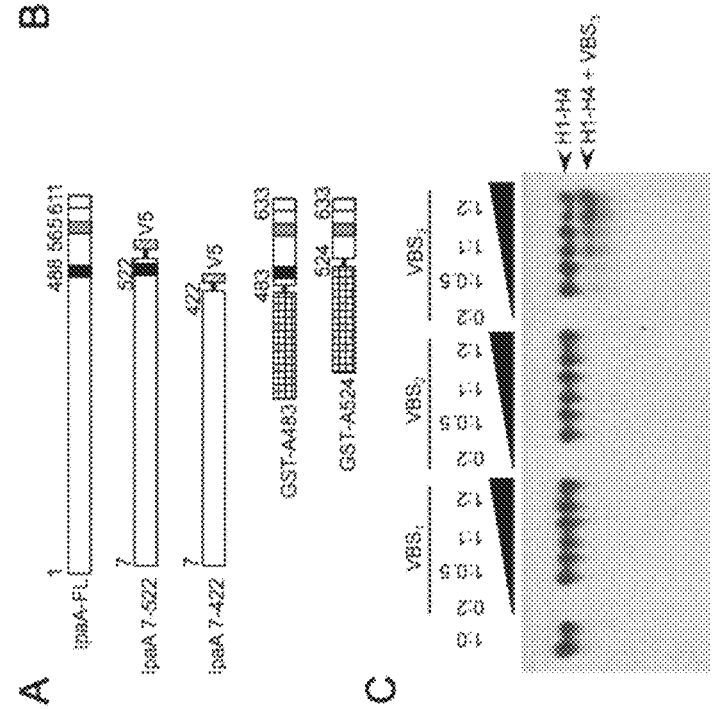
FIG. 8

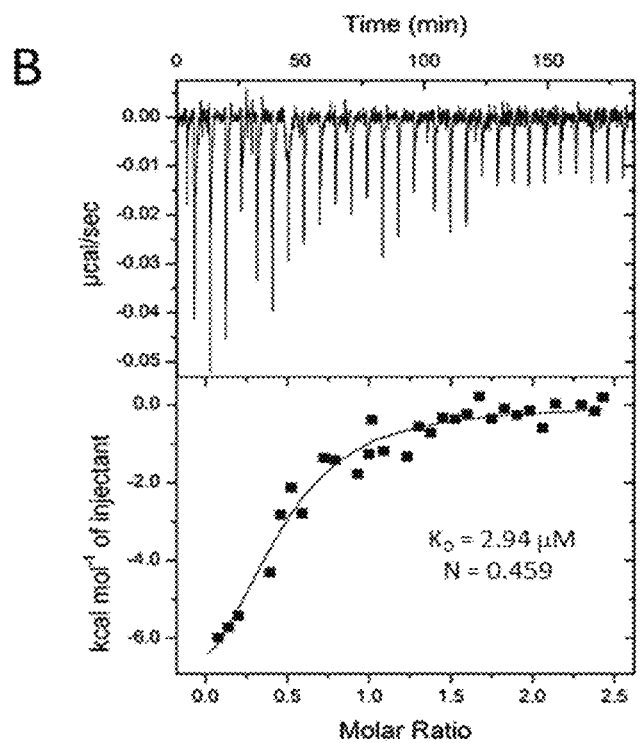
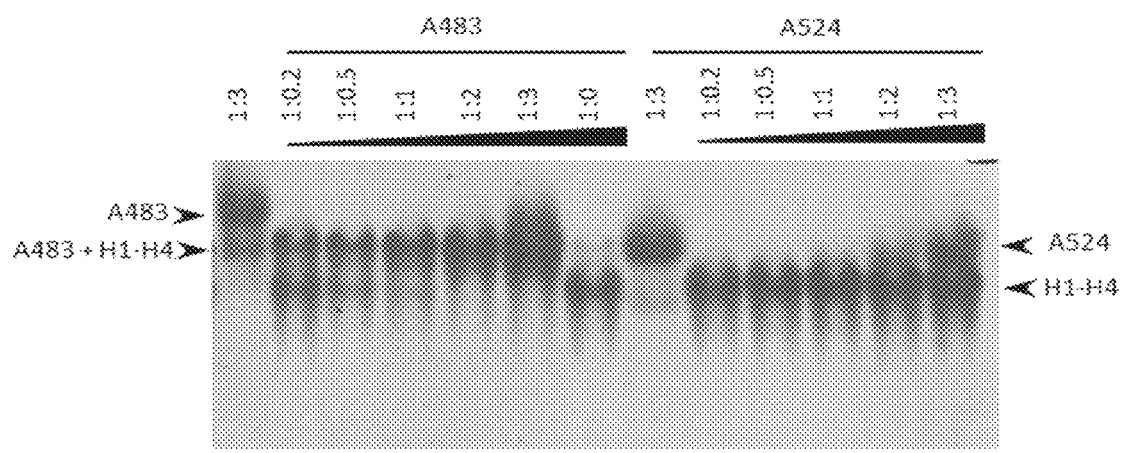
FIG. 9B-C

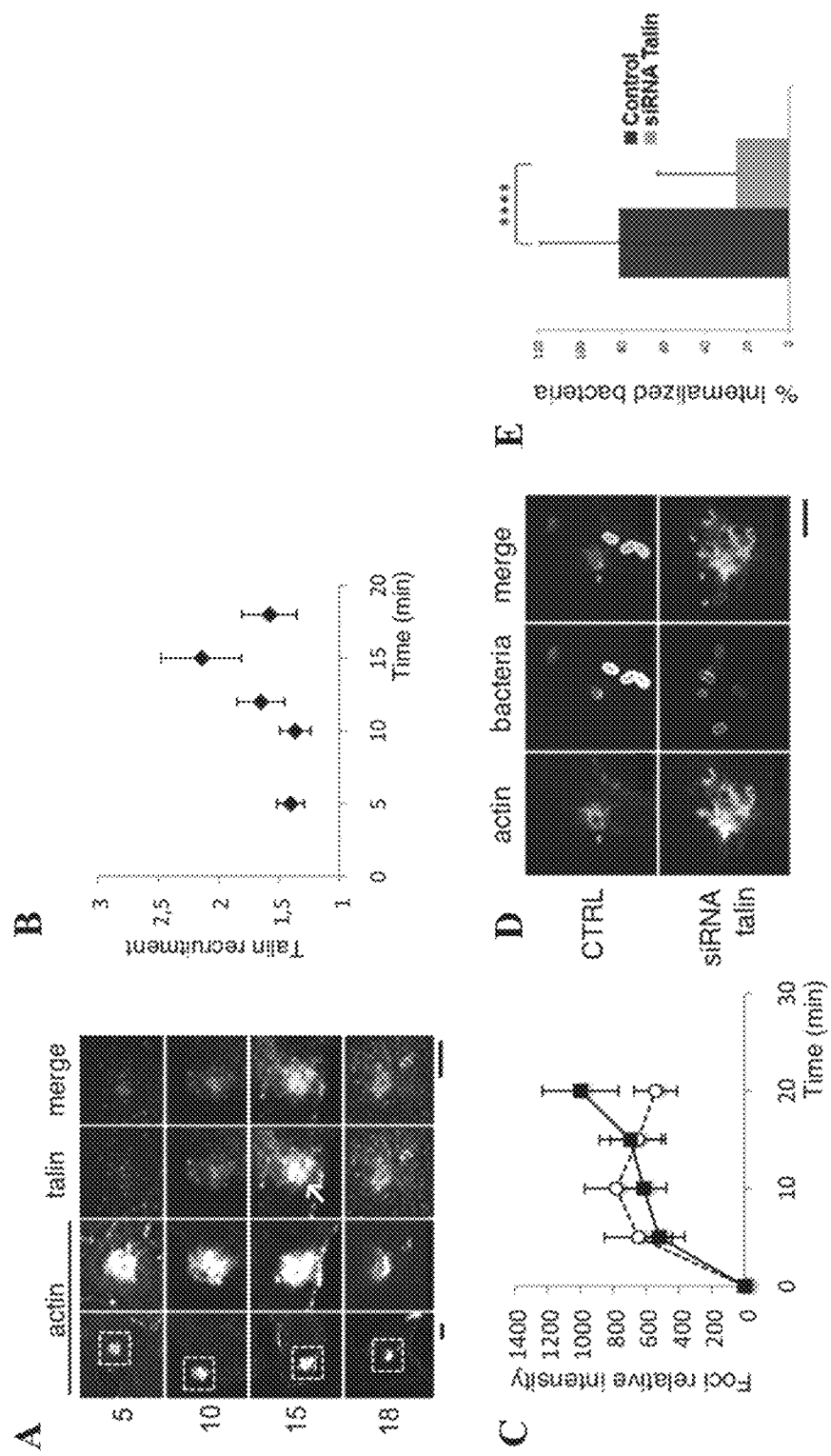
FIG. 11A-E

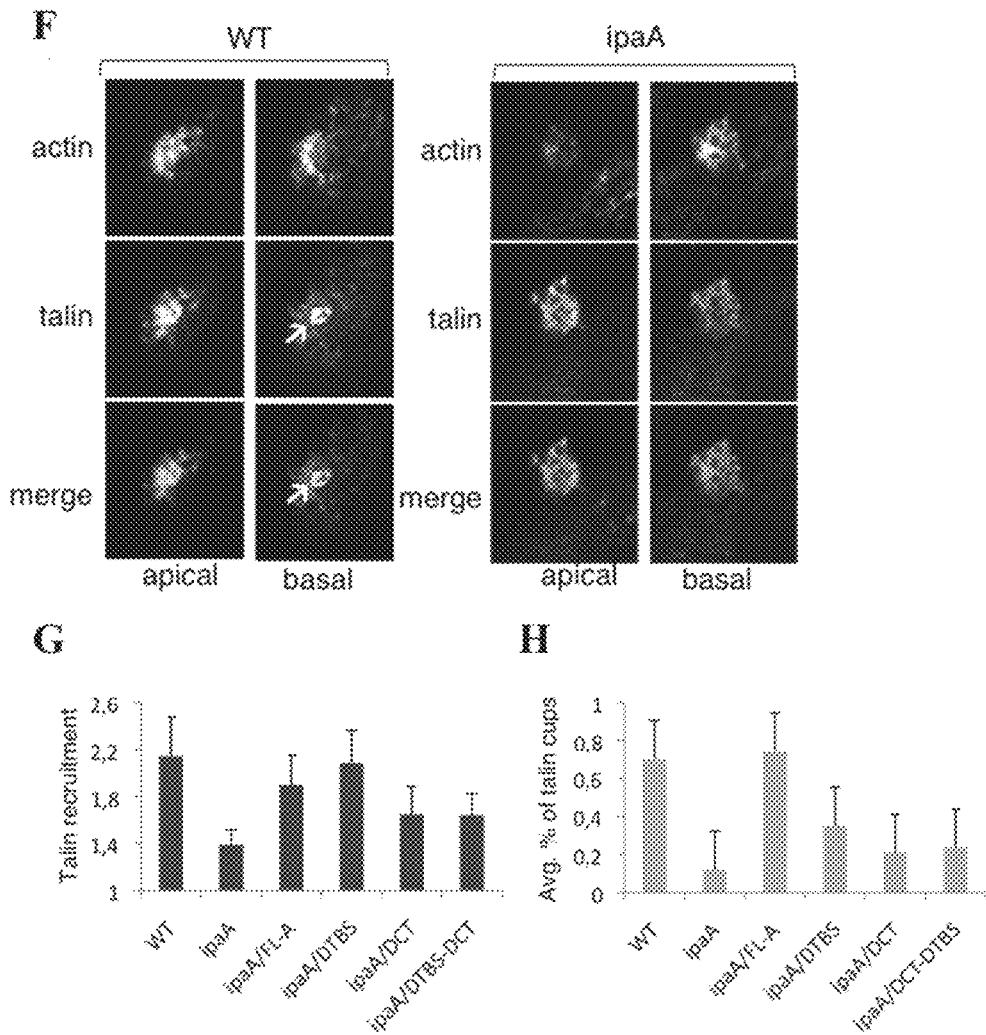
FIG. 11F-H

SEQUENCE LISTING

```
<160> NUMBER OF SEQ ID NOS: 79

<210> SEQ ID NO 1
<211> LENGTH: 633
<212> TYPE: PRT
<213> ORGANISM: Shigella flexneri
<220> FEATURE:
<223> OTHER INFORMATION: IpaA (1-633)

<400> SEQUENCE: 1

Met His Asn Val Asn Asn Thr Gln Ala Pro Thr Phe Leu Tyr Lys Ala
1               5                   10                  15
```

```
Thr Ser Pro Ser Ser Thr Glu Tyr Ser Glu Leu Lys Ser Lys Ile Ser
            20                  25                  30

Asp Ile His Ser Ser Gln Thr Ser Leu Lys Thr Pro Ala Ser Val Ser
        35                  40                  45

Glu Lys Glu Asn Phe Ala Thr Ser Phe Asn Gln Lys Cys Leu Asp Phe
50                  55                  60

Leu Phe Ser Ser Gly Lys Glu Asp Val Leu Arg Ser Ile Tyr Ser
65                  70                  75                  80

Asn Ser Met Asn Ala Tyr Ala Lys Ser Glu Ile Leu Glu Phe Ser Asn
                85                  90                  95

Val Leu Tyr Ser Leu Val His Gln Asn Gly Leu Asn Phe Glu Asn Glu
            100                 105                 110

Lys Gly Leu Gln Lys Ile Val Ala Gln Tyr Ser Glu Leu Ile Ile Lys
        115                 120                 125

Asp Lys Leu Ser Gln Asp Ser Ala Phe Gly Pro Trp Ser Ala Lys Asn
130                 135                 140

Lys Lys Leu His Gln Leu Arg Gln Asn Ile Glu His Arg Leu Ala Leu
145                 150                 155                 160

Leu Ala Gln Gln His Thr Ser Gly Glu Ala Leu Ser Leu Gly Gln Lys
                165                 170                 175

Leu Leu Asn Thr Glu Val Ser Ser Phe Ile Lys Asn Asn Ile Leu Ala
            180                 185                 190

Glu Leu Lys Leu Ser Asn Glu Thr Val Ser Ser Leu Lys Leu Asp Asp
        195                 200                 205

Leu Val Asp Ala Gln Ala Lys Leu Ala Phe Asp Ser Leu Arg Asn Gln
210                 215                 220

Arg Lys Asn Thr Ile Asp Ser Lys Gly Phe Gly Ile Gly Lys Leu Ser
225                 230                 235                 240

Arg Asp Leu Asn Thr Val Ala Val Phe Pro Glu Leu Leu Arg Lys Val
                245                 250                 255

Leu Asn Asp Ile Leu Glu Asp Ile Lys Asp Ser His Pro Ile Gln Asp
            260                 265                 270

Gly Leu Pro Thr Pro Pro Glu Asp Met Pro Asp Gly Gly Pro Thr Pro
        275                 280                 285

Gly Ala Asn Glu Lys Thr Ser Gln Pro Val Ile His Tyr His Ile Asn
290                 295                 300

Asn Asp Asn Arg Thr Tyr Asp Asn Arg Val Phe Asp Asn Arg Val Tyr
305                 310                 315                 320

Asp Asn Ser Tyr His Glu Asn Pro Glu Asn Asp Ala Gln Ser Pro Thr
                325                 330                 335

Ser Gln Thr Asn Asp Leu Leu Ser Arg Asn Gly Asn Ser Leu Leu Asn
            340                 345                 350

Pro Gln Arg Ala Leu Val Gln Lys Val Thr Ser Val Leu Pro His Ser
        355                 360                 365

Ile Ser Asp Thr Val Gln Thr Phe Ala Asn Asn Ser Ala Leu Glu Lys
370                 375                 380

Val Phe Asn His Thr Pro Asp Asn Ser Asp Gly Ile Gly Ser Asp Leu
385                 390                 395                 400

Leu Thr Thr Ser Ser Gln Glu Arg Ser Ala Asn Asn Ser Leu Ser Arg
                405                 410                 415

Gly His Arg Pro Leu Asn Ile Gln Asn Ser Ser Thr Pro Pro Leu
            420                 425                 430
```

His Pro Glu Gly Val Thr Ser Asn Asp Asn Ser Ser Asp Thr Thr
        435                 440                 445

Lys Ser Ser Ala Ser Leu Ser His Arg Val Ala Ser Gln Ile Asn Lys
450                 455                 460

Phe Asn Ser Asn Thr Asp Ser Lys Val Leu Gln Thr Asp Phe Leu Ser
465                 470                 475                 480

Arg Asn Gly Asp Thr Tyr Leu Thr Arg Glu Thr Ile Phe Glu Ala Ser
                485                 490                 495

Lys Lys Val Thr Asn Ser Leu Ser Asn Leu Ile Ser Leu Ile Gly Thr
            500                 505                 510

Lys Ser Gly Thr Gln Glu Arg Glu Leu Gln Glu Lys Ser Lys Asp Ile
        515                 520                 525

Thr Lys Ser Thr Thr Glu His Arg Ile Asn Asn Lys Leu Lys Val Thr
    530                 535                 540

Asp Ala Asn Ile Arg Asn Tyr Val Thr Glu Thr Asn Ala Asp Thr Ile
545                 550                 555                 560

Asp Lys Asn His Ala Ile Tyr Glu Lys Ala Lys Glu Val Ser Ser Ala
                565                 570                 575

Leu Ser Lys Val Leu Ser Lys Ile Asp Asp Thr Ser Ala Glu Leu Leu
            580                 585                 590

Thr Asp Asp Ile Ser Asp Leu Lys Asn Asn Asn Asp Ile Thr Ala Glu
        595                 600                 605

Asn Asn Asn Ile Tyr Lys Ala Ala Lys Asp Val Thr Thr Ser Leu Ser
    610                 615                 620

Lys Val Leu Lys Asn Ile Asn Lys Asp
625                 630

<210> SEQ ID NO 2
<211> LENGTH: 19
<212> TYPE: PRT
<213> ORGANISM: Shigella flexneri
<220> FEATURE:
<223> OTHER INFORMATION: IpaA VBS1

<400> SEQUENCE: 2

Ile Tyr Lys Ala Ala Lys Asp Val Thr Thr Ser Leu Ser Lys Val Leu
1               5                   10                  15

Lys Asn Ile

<210> SEQ ID NO 3
<211> LENGTH: 19
<212> TYPE: PRT
<213> ORGANISM: Shigella flexneri
<220> FEATURE:
<223> OTHER INFORMATION: IpaA VBS2

<400> SEQUENCE: 3

Ile Tyr Glu Lys Ala Lys Glu Val Ser Ser Ala Leu Ser Lys Val Leu
1               5                   10                  15

Ser Lys Ile

<210> SEQ ID NO 4
<211> LENGTH: 19
<212> TYPE: PRT
<213> ORGANISM: Shigella flexneri
<220> FEATURE:
<223> OTHER INFORMATION: IpaA VBS3

<400> SEQUENCE: 4

```
Ile Phe Glu Ala Ser Lys Lys Val Thr Asn Ser Leu Ser Asn Leu Ile
1               5                   10                  15

Ser Leu Ile
```

<210> SEQ ID NO 5
<211> LENGTH: 151
<212> TYPE: PRT
<213> ORGANISM: Shigella flexneri
<220> FEATURE:
<223> OTHER INFORMATION: A483 / IpaA (483-633)

<400> SEQUENCE: 5

```
Gly Asp Thr Tyr Leu Thr Arg Glu Thr Ile Phe Glu Ala Ser Lys Lys
1               5                   10                  15

Val Thr Asn Ser Leu Ser Asn Leu Ile Ser Leu Ile Gly Thr Lys Ser
                20                  25                  30

Gly Thr Gln Glu Arg Glu Leu Gln Glu Lys Ser Lys Asp Ile Thr Lys
            35                  40                  45

Ser Thr Thr Glu His Arg Ile Asn Asn Lys Leu Lys Val Thr Asp Ala
        50                  55                  60

Asn Ile Arg Asn Tyr Val Thr Glu Thr Asn Ala Asp Thr Ile Asp Lys
65                  70                  75                  80

Asn His Ala Ile Tyr Glu Lys Ala Lys Glu Val Ser Ser Ala Leu Ser
                85                  90                  95

Lys Val Leu Ser Lys Ile Asp Asp Thr Ser Ala Glu Leu Leu Thr Asp
                100                 105                 110

Asp Ile Ser Asp Leu Lys Asn Asn Asn Asp Ile Thr Ala Glu Asn Asn
            115                 120                 125

Asn Ile Tyr Lys Ala Ala Lys Asp Val Thr Thr Ser Leu Ser Lys Val
        130                 135                 140

Leu Lys Asn Ile Asn Lys Asp
145                 150
```

<210> SEQ ID NO 6
<211> LENGTH: 456
<212> TYPE: DNA
<213> ORGANISM: Shigella flexneri
<220> FEATURE:
<223> OTHER INFORMATION: A483 / IpaA (483-633)

<400> SEQUENCE: 6

```
ggagacacat atttaacacg ggaaacgata tttgaagctt caaaaaagt  aacaaactcc    60 ctaagtaatc ttatatctct cattggaact aaatcaggaa cacaagaacg agagttacag   120
gaaaaatcaa aggacattac aaaatccaca acagaacata aataaacaa  caattaaaa   180 gttacagatg caaatataag aaactacgta acagaaacca acgcagatac aattgataaa   240
aatcatgcga tctatgaaaa ggcaaaagaa gtatctagcg cccctcagcaa ggtattgtca   300 aaaattgacg ataccctctgc agaattactt acagatgata tatctgattt aaaaaataac   360
aatgatatta cagctgaaaa caataatata tataaagcag caaaagatgt aaccacttcc   420
ctatcaaaag tattaaagaa tatcaataag gattaa                              456
```

<210> SEQ ID NO 7
<211> LENGTH: 1902
<212> TYPE: DNA
<213> ORGANISM: Shigella flexneri
<220> FEATURE:
<223> OTHER INFORMATION: IpaA (1-633)

<400> SEQUENCE: 7

```
atgcataatg taaataatac tcaagcgcca acattcttat ataaggcaac ttcaccatca      60
tcaacagaat acagcgagtt aaaaagcaaa atatccgata tccatagttc gcaaacttct     120
ctaaaaacac cagcatcagt gtctgaaaaa gaaaactttg caacgtcttt taatcagaaa     180
tgtcttgatt ttttattttc ttcctcaggg aaagaagatg tgttaagaag catttattcc     240
aactcaatga atgcgtatgc caaaagcgag attctcgaat tttcaaatgt tttgtactcc     300
ttagtacatc aaaatggtct taattttgaa acgaaaagg gacttcaaaa aattgtcgca     360
cagtattcgg aactaattat aaaagataaa ttatcccaag attctgcctt tggaccatgg     420
tcggcaaaga ataagaaact ccatcaatta cgacaaaaca ttgagcacag acttgcacta     480
ttagcacaac aacacacatc tggtgaagct ttatcattgg acaaaaact cctcaatact     540
gaagtatcat catttatcaa gaataatatt cttgctgaat aaagttaag taatgaaact     600
gtttcatctc tcaaactaga tgatttagtt gacgcacagg caaaacttgc ctttgatagt     660
ttgcgcaatc aacgtaaaaa tactattgat agtaaaggat ttggtatagg taaactgtca     720
agagacttaa atacagtagc cgtgtttcct gagctgttga gaaaagtcct taatgatatt     780
ttagaagata taaaagattc gcatcctatc caagatggcc tccctacacc tcccgaagat     840
atgccagatg gcggaccaac ccccggagcc aatgagaaaa catcccaacc tgtaattcac     900
tatcatataa ataatgataa tagaacttac gataatagag tttttgacaa cagagtatat     960
gacaatagct atcacgagaa cccagaaaat gatgcacagt ctcctacttc tcagacaaac    1020
gatctattat cccgtaacgg aaactcatta ctaaatccac aaagagcact agttcaaaaa    1080
gtaacttccg ttctaccaca ctctatatca gatactgtcc agacatttgc aaataattca    1140
gctttagaaa aggttttcaa ccatactcca gataattcgg atggaatagg ttcagacctg    1200
ttaactacga gtagtcaaga agatctgca aataactctc tttctcgggg acacaggcct    1260
ctgaacatac agaactcttc aaccaccccc cctctccacc cggaaggagt gacaagcagt    1320
aatgataact catcagatac aactaaaagt agcgcttctc tttctcatag agtagcttcg    1380
caaatcaata aattcaactc aaacactgat tcaaaagtac ttcagactga ttttttatca    1440
agaaatggag acacatattt aacacgggaa acgatatttg aagcttcaaa aaaagtaaca    1500
aactcccctaa gtaatcttat atctctcatt ggaactaaat caggaacaca gaacgagag    1560
ttacaggaaa atcaaagga cattacaaaa tccacaacag aacatagaat aaacaacaaa    1620
ttaaaagtta cagatgcaaa tataagaaac tacgtaacag aaaccaacgc agatacaatt    1680
gataaaaatc atgcgatcta tgaaaaggca aaagaagtat ctagcgccct cagcaaggta    1740
ttgtcaaaaa ttgacgatac ctctgcagaa ttacttacag atgatatatc tgatttaaaa    1800
aataacaatg atattacagc tgaaaacaat aatatatata agcagcaaa agatgtaacc    1860
acttccctat caaagtatt aagaatatc aataaggatt aa                        1902
```

<210> SEQ ID NO 8
<211> LENGTH: 57
<212> TYPE: DNA
<213> ORGANISM: Shigella flexneri
<220> FEATURE:
<223> OTHER INFORMATION: IpaA VBS1

<400> SEQUENCE: 8

```
atatataaag cagcaaaaga tgtaaccact tccctatcaa agtattaaa gaatatc         57
```

```
<210> SEQ ID NO 9
<211> LENGTH: 57
<212> TYPE: DNA
<213> ORGANISM: Shigella flexneri
<220> FEATURE:
<223> OTHER INFORMATION: IpaA VBS2

<400> SEQUENCE: 9
atctatgaaa aggcaaaaga agtatctagc gccctcagca aggtattgtc aaaaatt    57

<210> SEQ ID NO 10
<211> LENGTH: 57
<212> TYPE: DNA
<213> ORGANISM: Shigella flexneri
<220> FEATURE:
<223> OTHER INFORMATION: IpaA VBS3

<400> SEQUENCE: 10
atatttgaag cttcaaaaaa agtaacaaac tccctaagta atcttatatc tctcatt    57

<210> SEQ ID NO 11
<211> LENGTH: 258
<212> TYPE: PRT
<213> ORGANISM: Homo sapiens
<220> FEATURE:
<223> OTHER INFORMATION: Vinculin domain D1 (HVD1)

<400> SEQUENCE: 11
```

Met Pro Val Phe His Thr Arg Thr Ile Glu Ser Ile Leu Glu Pro Val
1               5                   10                  15

Ala Gln Gln Ile Ser His Leu Val Ile Met His Glu Glu Gly Glu Val
            20                  25                  30

Asp Gly Lys Ala Ile Pro Asp Leu Thr Ala Pro Val Ala Ala Val Gln
        35                  40                  45

Ala Ala Val Ser Asn Leu Val Arg Val Gly Lys Glu Thr Val Gln Thr
    50                  55                  60

Thr Glu Asp Gln Ile Leu Lys Arg Asp Met Pro Pro Ala Phe Ile Lys
65                  70                  75                  80

Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
            100                 105                 110

Arg Gly Ile Leu Ser Gly Thr Ser Asp Leu Leu Leu Thr Phe Asp Glu
        115                 120                 125

Ala Glu Val Arg Lys Ile Ile Arg Val Cys Lys Gly Ile Leu Glu Tyr
    130                 135                 140

Leu Thr Val Ala Glu Val Val Glu Thr Met Glu Asp Leu Val Thr Tyr
145                 150                 155                 160

Thr Lys Asn Leu Gly Pro Gly Met Thr Lys Met Ala Lys Met Ile Asp
                165                 170                 175

Glu Arg Gln Gln Glu Leu Thr His Gln Glu His Arg Val Met Leu Val
            180                 185                 190

Asn Ser Met Asn Thr Val Lys Glu Leu Leu Pro Val Leu Ile Ser Ala
        195                 200                 205

Met Lys Ile Phe Val Thr Thr Lys Asn Ser Lys Asn Gln Gly Ile Glu
    210                 215                 220

Glu Ala Leu Lys Asn Arg Asn Phe Thr Val Glu Lys Met Ser Ala Glu
225                 230                 235                 240

Ile Asn Glu Ile Ile Arg Val Leu Gln Leu Thr Ser Trp Asp Glu Asp

```
                    245                 250                 255

Ala Trp

<210> SEQ ID NO 12
<211> LENGTH: 226
<212> TYPE: PRT
<213> ORGANISM: Homo sapiens
<220> FEATURE:
<223> OTHER INFORMATION: Vinculin domain D2 (HVD2)

<400> SEQUENCE: 12

Ala Ser Lys Asp Thr Glu Ala Met Lys Arg Ala Leu Ala Ser Ile Asp
1               5                   10                  15

Ser Lys Leu Asn Gln Ala Lys Gly Trp Leu Arg Asp Pro Ser Ala Ser
            20                  25                  30

Pro Gly Asp Ala Gly Glu Gln Ala Ile Arg Gln Ile Leu Asp Glu Ala
        35                  40                  45

Gly Lys Val Gly Glu Leu Cys Ala Gly Lys Glu Arg Arg Glu Ile Leu
    50                  55                  60

Gly Thr Cys Lys Met Leu Gly Gln Met Thr Asp Gln Val Ala Asp Leu
65                  70                  75                  80

Arg Ala Arg Gly Gln Gly Ser Ser Pro Val Ala Met Gln Lys Ala Gln
                85                  90                  95

Gln Val Ser Gln Gly Leu Asp Val Leu Thr Ala Lys Val Glu Asn Ala
            100                 105                 110

Ala Arg Lys Leu Glu Ala Met Thr Asn Ser Lys Gln Ser Ile Ala Lys
        115                 120                 125

Lys Ile Asp Ala Ala Gln Asn Trp Leu Ala Asp Pro Asn Gly Gly Pro
    130                 135                 140

Glu Gly Glu Glu Gln Ile Arg Gly Ala Leu Ala Glu Ala Arg Lys Ile
145                 150                 155                 160

Ala Glu Leu Cys Asp Asp Pro Lys Glu Arg Asp Asp Ile Leu Arg Ser
                165                 170                 175

Leu Gly Glu Ile Ser Ala Leu Thr Ser Lys Leu Ala Asp Leu Arg Arg
            180                 185                 190

Gln Gly Lys Gly Asp Ser Pro Glu Ala Arg Ala Leu Ala Lys Gln Val
        195                 200                 205

Ala Thr Ala Leu Gln Asn Leu Gln Thr Lys Thr Asn Arg Ala Val Ala
    210                 215                 220

Asn Ser
225

<210> SEQ ID NO 13
<211> LENGTH: 232
<212> TYPE: PRT
<213> ORGANISM: Homo sapiens
<220> FEATURE:
<223> OTHER INFORMATION: Vinculin domain D3 (HVD3)

<400> SEQUENCE: 13

Arg Pro Ala Lys Ala Ala Val His Leu Glu Gly Lys Ile Glu Gln Ala
1               5                   10                  15

Gln Arg Trp Ile Asp Asn Pro Thr Val Asp Asp Arg Gly Val Gly Gln
            20                  25                  30

Ala Ala Ile Arg Gly Leu Val Ala Glu Gly His Arg Leu Ala Asn Val
        35                  40                  45

Met Met Gly Pro Tyr Arg Gln Asp Leu Leu Ala Lys Cys Asp Arg Val
```

```
            50                  55                  60
Asp Gln Leu Thr Ala Gln Leu Ala Asp Leu Ala Ala Arg Gly Glu Gly
 65                  70                  75                  80

Glu Ser Pro Gln Ala Arg Ala Leu Ala Ser Gln Leu Gln Asp Ser Leu
                 85                  90                  95

Lys Asp Leu Lys Ala Arg Met Gln Glu Ala Met Thr Gln Glu Val Ser
            100                 105                 110

Asp Val Phe Ser Asp Thr Thr Thr Pro Ile Lys Leu Leu Ala Val Ala
        115                 120                 125

Ala Thr Ala Pro Pro Asp Ala Pro Asn Arg Glu Glu Val Phe Asp Glu
    130                 135                 140

Arg Ala Ala Asn Phe Glu Asn His Ser Gly Lys Leu Gly Ala Thr Ala
145                 150                 155                 160

Glu Lys Ala Ala Ala Val Gly Thr Ala Asn Lys Ser Thr Val Glu Gly
                165                 170                 175

Ile Gln Ala Ser Val Lys Thr Ala Arg Glu Leu Thr Pro Gln Val Val
            180                 185                 190

Ser Ala Ala Arg Ile Leu Leu Arg Asn Pro Gly Asn Gln Ala Ala Tyr
        195                 200                 205

Glu His Phe Glu Thr Met Lys Asn Gln Trp Ile Asp Asn Val Glu Lys
    210                 215                 220

Met Thr Gly Leu Val Asp Glu Ala
225                 230

<210> SEQ ID NO 14
<211> LENGTH: 118
<212> TYPE: PRT
<213> ORGANISM: Homo sapiens
<220> FEATURE:
<223> OTHER INFORMATION: Vinculin domain D4 (HVD4)

<400> SEQUENCE: 14

Ile Asp Thr Lys Ser Leu Leu Asp Ala Ser Glu Glu Ala Ile Lys Lys
 1               5                  10                  15

Asp Leu Asp Lys Cys Lys Val Ala Met Ala Asn Ile Gln Pro Gln Met
            20                  25                  30

Leu Val Ala Gly Ala Thr Ser Ile Ala Arg Arg Ala Asn Arg Ile Leu
        35                  40                  45

Leu Val Ala Lys Arg Glu Val Glu Asn Ser Glu Asp Pro Lys Phe Arg
    50                  55                  60

Glu Ala Val Lys Ala Ala Ser Asp Glu Leu Ser Lys Thr Ile Ser Pro
 65                  70                  75                  80

Met Val Met Asp Ala Lys Ala Val Ala Gly Asn Ile Ser Asp Pro Gly
                 85                  90                  95

Leu Gln Lys Ser Phe Leu Asp Ser Gly Tyr Arg Ile Leu Gly Ala Val
            100                 105                 110

Ala Lys Val Arg Glu Ala
        115

<210> SEQ ID NO 15
<211> LENGTH: 110
<212> TYPE: PRT
<213> ORGANISM: Shigella flexneri
<220> FEATURE:
<223> OTHER INFORMATION: A524 / IpaA (524-633)

<400> SEQUENCE: 15
```

Lys Ser Lys Asp Ile Thr Lys Ser Thr Thr Glu His Arg Ile Asn Asn
1               5                   10                  15

Lys Leu Lys Val Thr Asp Ala Asn Ile Arg Asn Tyr Val Thr Glu Thr
            20                  25                  30

Asn Ala Asp Thr Ile Asp Lys Asn His Ala Ile Tyr Glu Lys Ala Lys
            35                  40                  45

Glu Val Ser Ser Ala Leu Ser Lys Val Leu Ser Lys Ile Asp Asp Thr
        50                  55                  60

Ser Ala Glu Leu Leu Thr Asp Asp Ile Ser Asp Leu Lys Asn Asn Asn
65                  70                  75                  80

Asp Ile Thr Ala Glu Asn Asn Asn Ile Tyr Lys Ala Ala Lys Asp Val
                85                  90                  95

Thr Thr Ser Leu Ser Lys Val Leu Lys Asn Ile Asn Lys Asp
            100                 105                 110

<210> SEQ ID NO 16
<211> LENGTH: 3201
<212> TYPE: DNA
<213> ORGANISM: Artificial Sequence
<220> FEATURE:
<223> OTHER INFORMATION: Human vinculin construct (HV)

<400> SEQUENCE: 16

```
atgccagtgt tcatacgcg cacgatcgag agcatcctgg agccggtggc acagcagatc      60
tcccacctgg tgataatgca cgaggagggc gaggtggacg gcaaagccat tcctgacctc    120
accgcgcccg tggccgccgt gcaggcggcc gtcagcaacc tcgtccgggt tggaaaagag    180
actgttcaaa ccactgagga tcagattttg aagagagata tgccaccagc atttattaag    240
gttgagaatg cttgcaccaa gcttgtccag gcagctcaga tgcttcagtc agacccttac    300
tcagtgcctg ctcgagatta tctaattgat gggtcaaggg gcatcctctc tggaacatca    360
gacctgctcc ttaccttcga tgaggctgag gtccgtaaaa ttattagagt ttgcaaagga    420
attttggaat atcttacagt ggcagaggtg gtggagacta tggaagatt tggtcacttac    480 acaaagaatc ttgggccagg aatgactaag atggccaaga tgattgacga gagacagcag    540
gagctcactc accaggagca ccgagtgatg ttggtgaact cgatgaacac cgtgaaagag    600
ttgctgccag ttctcatttc agctatgaag attttgtaa caactaaaaa ctcaaaaaac    660
caaggcatag aggaagcttt aaaaaatcgc aattttactg tagaaaaaat gagtgctgaa    720
attaatgaga taattcgtgt gttacaactc acctcttggg atgaagatgc ctgggccagc    780
aaggacactg aagccatgaa gagagcattg gcctccatag actccaaact gaaccaggcc    840
aaaggttggc tccgtgaccc tagtgcctcc ccaggggatg ctggtgagca ggccatcaga    900
cagatcttag atgaagctgg aaaagttggt gaactctgtg caggcaaaga acgcagggag    960
attctgggaa cttgcaaaat gctagggcag atgactgatc aagtggctga cctccgtgcc   1020
agaggacaag atcctcacc ggtggccatg cagaaagctc agcaggtatc tcagggtctg   1080
gatgtgctca cagcaaaagt ggaaaatgca gctcgcaagc tggaagccat gaccaactca   1140
aagcagagca ttgcaaagaa gatcgatgct gctcagaact ggcttgcaga tccaaatggt   1200
ggaccggaag agaagagca gattcgaggt gctttggctg aagctcggaa atagcagaa    1260 ttatgtgatg atcctaaaga aagagatgac attctacgtt cccttgggga atatctgct    1320 ctgacttcta aattagcaga tctacgaaga caggggaaag gagattctcc agaggctcga    1380
gccttggcca acaggtggc cacggccctg cagaacctgc agaccaaaac caaccgggct    1440
```

```
gtggccaaca gcagaccggc caaagcagct gtacaccttg agggcaagat tgagcaagca    1500
cagcggtgga ttgataatcc cacagtggat gaccgtggag tcggtcaggc tgccatccgg    1560
gggcttgtgg ccgaagggca tcgtctggct aatgttatga tggggcctta tcggcaagat    1620
cttctcgcca gtgtgaccg agtggaccag ctgacagccc agctggctga cctggctgcc     1680
agaggggaag gggagagtcc tcaggcacga gcacttgcat ctcagctcca agactcctta    1740
aaggatctaa aagctcggat gcaggaggcc atgactcagg aagtgtcaga tgttttcagc    1800
gataccacaa ctcccatcaa gctgttggca gtggcagcca cggcgcctcc tgatgcgcct    1860
aacagggaag aggtatttga tgagagggca gctaactttg aaaaccattc aggaaagctt    1920
ggtgctacgg ccgagaaggc ggctgcggtt ggtactgcta ataaatcaac agtggaaggc    1980
attcaggcct cagtgaagac ggcccgagaa ctcacacccc aggtggtctc ggctgctcgt    2040
atcttactta ggaaccctgg aaatcaagct gcttatgaac attttgagac catgaagaac    2100
cagtggatcg ataatgttga aaaaatgaca gggctggtgg acgaagccat tgataccaaa    2160
tctctgttgg atgcttcaga agaagcaatt aaaaaagacc tggacaagtg caaggtagct    2220
atggccaaca ttcagcctca gatgctggtt gctgggcaa ccagtattgc tcgtcgggcc     2280
aaccggatcc tgctggtggc taagagggag gtggagaatt ccgaggatcc caagttccgt    2340
gaggctgtga agctgcctc tgatgaattg agcaaaacca tctccccaat ggtgatggat     2400
gcaaaagctg tggctggaaa catttccgac cctggactgc aaaagagctt cctggactca    2460
ggatatcgga tcctgggagc tgtggccaag gtcagagaag ccttccaacc tcaggagcct    2520
gacttcccgc cgcctccacc agaccttgaa caactccgac taacagatga gcttgctcct    2580
cccaaaccac ctctgcctga aggtgaggtc cctccaccta ggcctccacc accagaggaa    2640
aaggatgaag agttccctga gcagaaggcc ggggaggtga ttaaccagcc aatgatgatg    2700
gctgccagac agctccatga tgaagctcgc aaatggtcca gcaagggcaa tgacatcatt    2760
gcagcagcca gcgcatggc tctgctgatg gctgagatgt ctcggctggt aagaggggggc    2820 agtggtacca agcgggcact cattcagtgt gccaaggaca tcgccaaggc ctcagatgag    2880
gtgactcggt tggccaagga ggttgccaag cagtgcacag ataaacggat tagaaccaac    2940
ctcttacagg tatgtgagcg aatcccaacc ataagcaccc agctcaaaat cctgtccaca    3000
gtgaaggcca ccatgctggg ccggaccaac atcagtgatg aggagtctga gcaggccaca    3060
gagatgctgg ttcacaatgc ccagaacctc atgcagtctg tgaaggagac tgtgcgggaa    3120
gctgaagctg cttcaatcaa aattcgaaca gatgctggat ttacactgcg ctgggttaga    3180 aagactcct ggtaccagta g                                                3201
```

<210> SEQ ID NO 17
<211> LENGTH: 24
<212> TYPE: DNA
<213> ORGANISM: Artificial Sequence
<220> FEATURE:
<223> OTHER INFORMATION: HV Fwd primer

<400> SEQUENCE: 17
gcgcatatgc cagtgtttca tacg                                              24

<210> SEQ ID NO 18
<211> LENGTH: 25
<212> TYPE: DNA
<213> ORGANISM: Artificial Sequence
<220> FEATURE:
<223> OTHER INFORMATION: HV Rv primer

<400> SEQUENCE: 18
cgtcgactca ccaggcatct tcatc                                          25

<210> SEQ ID NO 19
<211> LENGTH: 26
<212> TYPE: DNA
<213> ORGANISM: Artificial Sequence
<220> FEATURE:
<223> OTHER INFORMATION: HV Rv primer

<400> SEQUENCE: 19
cgtcgactca gtgtacagct gctttg                                         26

<210> SEQ ID NO 20
<211> LENGTH: 41
<212> TYPE: DNA
<213> ORGANISM: Artificial Sequence
<220> FEATURE:
<223> OTHER INFORMATION: HV_K276R Fwd primer

<400> SEQUENCE: 20
gcattggcct ccatagactc ccgtctgaac caggccaaag g                        41

<210> SEQ ID NO 21
<211> LENGTH: 41
<212> TYPE: DNA
<213> ORGANISM: Artificial Sequence
<220> FEATURE:
<223> OTHER INFORMATION: HV_K276R Rv primer

<400> SEQUENCE: 21
cctttggcct ggttcagacg ggagtctatg gaggccaatg c                        41

<210> SEQ ID NO 22
<211> LENGTH: 41
<212> TYPE: DNA
<213> ORGANISM: Artificial Sequence
<220> FEATURE:
<223> OTHER INFORMATION: HV_E305Q Fwd primer

<400> SEQUENCE: 22
ggccatcaga cagatcttag atcaagctgg aaaagttggt g                        41

<210> SEQ ID NO 23
<211> LENGTH: 41
<212> TYPE: DNA
<213> ORGANISM: Artificial Sequence
<220> FEATURE:
<223> OTHER INFORMATION: HV_E305Q Rv primer

<400> SEQUENCE: 23
caccaacttt tccagcttga tctaagatct gtctgatggc c                        41

<210> SEQ ID NO 24
<211> LENGTH: 22
<212> TYPE: DNA
<213> ORGANISM: Artificial Sequence
<220> FEATURE:
<223> OTHER INFORMATION: GFP-IpaA483 Fwd primer

<400> SEQUENCE: 24
gcgatatcat ggccagcaaa gg                                             22

<210> SEQ ID NO 25

<210> SEQ ID NO 25
<211> LENGTH: 29
<212> TYPE: DNA
<213> ORGANISM: Artificial Sequence
<220> FEATURE:
<223> OTHER INFORMATION: GFP-IpaA483 Rv primer

<400> SEQUENCE: 25
gcgcggccgc ttaatcctta ttgatattc                                29

<210> SEQ ID NO 26
<211> LENGTH: 31
<212> TYPE: DNA
<213> ORGANISM: Artificial Sequence
<220> FEATURE:
<223> OTHER INFORMATION: GST-IpaA483 Fwd primer

<400> SEQUENCE: 26
ggcgaattcc cggagacaca tatttaacac g                             31

<210> SEQ ID NO 27
<211> LENGTH: 29
<212> TYPE: DNA
<213> ORGANISM: Artificial Sequence
<220> FEATURE:
<223> OTHER INFORMATION: GST-IpaA483 Rv primer

<400> SEQUENCE: 27
gccgtcgact taatccttat tgatattct                                29

<210> SEQ ID NO 28
<211> LENGTH: 1242
<212> TYPE: DNA
<213> ORGANISM: Artificial Sequence
<220> FEATURE:
<223> OTHER INFORMATION: GFP-IpaA483

<400> SEQUENCE: 28
atggccagca aaggagaaga acttttcact ggagttgtcc caattcttgt tgaattagat     60
ggtgatgtta atgggcacaa attttctgtc agtggagagg gtgaaggtga tgctacatac    120
ggaaagctta cccttaaatt tatttgcact actggaaaac tacctgttcc atggccaaca    180
cttgtcacta ctttctctta tggtgttcaa tgcttttccc gttatccgga tcatatgaaa    240
cggcatgact ttttcaagag tgccatgccc gaaggttatg tacaggaacg cactatatct    300
ttcaaagatg acgggaacta caagacgcgt gctgaagtca gtttgaaggt gatacccctt    360
gttaatcgta tcgagttaaa aggtattgat tttaaagaag atggaaacat tctcggacac    420
aaactcgagt acaactataa ctcacacaat gtatacatca cggcagacaa acaaaagaat    480
ggaatcaaag ctaacttcaa aattcgccac aacattgaag atggatccgt tcaactagca    540
gaccattatc aacaaaatac tccaattggc gatggccctg tccttttacc agacaaccat    600
tacctgtcga cacaatctgc cctttcgaaa gatcccaacg aaaagcgtga ccacatggtc    660
cttcttgagt ttgtaactgc tgctgggatt acacatggca tggatgagct ctacaaaagc    720
ggttccggac cggtgctagc ggtaccgagc tcggatccac tagtccagtg tggtggaatt    780
gcccttggag acatatattt aacacgggaa acgatatttg aagcttcaaa aaagtaaca    840
aactccctaa gtaatcttat atctctcatt ggaactaaat caggaacaca agaacgagag    900
ttacaggaaa aatcaaagga cattacaaaa tccacaacag aacatagaat aaacaacaaa    960
ttaaaagtta cagatgcaaa tataagaaac tacgtaacag aaaccaacgc agatacaatt   1020
gataaaaatc atgcgatcta tgaaaaggca aagaagtat ctagcgccct cagcaaggta   1080

| ttgtcaaaaa ttgacgatac ctctgcagaa ttacttacag atgatatatc tgatttaaaa | 1140 |
| aataacaatg atattacagc tgaaaacaat aatatatata aagcagcaaa agatgtaacc | 1200 |
| acttccctat caaaagtatt aaagaatatc aataaggatt aa | 1242 |

<210> SEQ ID NO 29
<211> LENGTH: 1146
<212> TYPE: DNA
<213> ORGANISM: Artificial Sequence
<220> FEATURE:
<223> OTHER INFORMATION: GST-IpaA483

<400> SEQUENCE: 29

| atgtccccta tactaggtta ttggaaaatt aagggccttg tgcaacccac tcgacttctt | 60 |
| ttggaatatc ttgaagaaaa atatgaagag catttgtatg agcgcgatga aggtgataaa | 120 |
| tggcgaaaca aaaagtttga attgggtttg agtttcccaa tcttccttta ttatattgat | 180 |
| ggtgatgtta aattaacaca gtctatggcc atcatacgtt atatagctga caagcacaac | 240 |
| atgttgggtg gttgtccaaa agagcgtgca gagatttcaa tgcttgaagg agcggttttg | 300 |
| gatattagat acggtgtttc gagaattgca tatagtaaag actttgaaac tctcaaagtt | 360 |
| gattttctta gcaagctacc tgaaatgctg aaaatgttcg aagatcgttt atgtcataaa | 420 |
| acatatttaa atggtgatca tgtaacccat cctgacttca tgttgtatga cgctcttgat | 480 |
| gttgttttat acatggaccc aatgtgcctg gatgcgttcc caaaattagt ttgttttaaa | 540 |
| aaacgtattg aagctatccc acaaattgat aagtacttga atccagcaa gtatatagca | 600 |
| tggcctttgc agggctggca agccacgttt ggtggtggcg accatcctcc aaaatcggat | 660 |
| ctggttccgc gtggatcccc aggaattccc ggagacacat atttaacacg ggaaacgata | 720 |
| tttgaagctt caaaaaaagt aacaaactcc ctaagtaatc ttatatctct cattggaact | 780 |
| aaatcaggaa cacaagaacg agagttacag gaaaaatcaa aggacattac aaaatccaca | 840 |
| acagaacata gaataaacaa caaattaaaa gttacagatg caaatataag aaactacgta | 900 |
| acagaaacca acgcagatac aattgataaa atcatgcga tctatgaaaa ggcaaaagaa | 960 |
| gtatctagcg ccctcagcaa ggtattgtca aaaattgacg atacctctgc agaattactt | 1020 |
| acagatgata tatctgattt aaaaaataac aatgatatta cagctgaaaa caataatata | 1080 |
| tataaagcag caaagatgt aaccacttcc ctatcaaaag tattaaagaa tatcaataag | 1140 |
| gattaa | 1146 |

<210> SEQ ID NO 30
<211> LENGTH: 25
<212> TYPE: RNA
<213> ORGANISM: Artificial Sequence
<220> FEATURE:
<223> OTHER INFORMATION: anti-talin 1 siRNA

<400> SEQUENCE: 30

| ccaagaacgg aaaccugcca gaguu | 25 |

<210> SEQ ID NO 31
<211> LENGTH: 1066
<212> TYPE: PRT
<213> ORGANISM: Homo sapiens
<220> FEATURE:
<223> OTHER INFORMATION: Human vinculin (HV)

<400> SEQUENCE: 31

```
Met Pro Val Phe His Thr Arg Thr Ile Glu Ser Ile Leu Glu Pro Val
1               5                   10                  15

Ala Gln Gln Ile Ser His Leu Val Ile Met His Glu Gly Glu Val
            20                  25                  30

Asp Gly Lys Ala Ile Pro Asp Leu Thr Ala Pro Val Ala Ala Val Gln
            35                  40                  45

Ala Ala Val Ser Asn Leu Val Arg Val Gly Lys Glu Thr Val Gln Thr
50                  55                  60

Thr Glu Asp Gln Ile Leu Lys Arg Asp Met Pro Ala Phe Ile Lys
65                  70                  75                  80

Val Glu Asn Ala Cys Thr Lys Leu Val Gln Ala Ala Gln Met Leu Gln
                85                  90                  95

Ser Asp Pro Tyr Ser Val Pro Ala Arg Asp Tyr Leu Ile Asp Gly Ser
                100                 105                 110

Arg Gly Ile Leu Ser Gly Thr Ser Asp Leu Leu Leu Thr Phe Asp Glu
            115                 120                 125

Ala Glu Val Arg Lys Ile Ile Arg Val Cys Lys Gly Ile Leu Glu Tyr
130                 135                 140

Leu Thr Val Ala Glu Val Val Glu Thr Met Glu Asp Leu Val Thr Tyr
145                 150                 155                 160

Thr Lys Asn Leu Gly Pro Gly Met Thr Lys Met Ala Lys Met Ile Asp
                165                 170                 175

Glu Arg Gln Gln Glu Leu Thr His Gln Glu His Arg Val Met Leu Val
            180                 185                 190

Asn Ser Met Asn Thr Val Lys Glu Leu Leu Pro Val Leu Ile Ser Ala
            195                 200                 205

Met Lys Ile Phe Val Thr Thr Lys Asn Ser Lys Asn Gln Gly Ile Glu
210                 215                 220

Glu Ala Leu Lys Asn Arg Asn Phe Thr Val Glu Lys Met Ser Ala Glu
225                 230                 235                 240

Ile Asn Glu Ile Ile Arg Val Leu Gln Leu Thr Ser Trp Asp Glu Asp
                245                 250                 255

Ala Trp Ala Ser Lys Asp Thr Glu Ala Met Lys Arg Ala Leu Ala Ser
            260                 265                 270

Ile Asp Ser Lys Leu Asn Gln Ala Lys Gly Trp Leu Arg Asp Pro Ser
            275                 280                 285

Ala Ser Pro Gly Asp Ala Gly Glu Gln Ala Ile Arg Gln Ile Leu Asp
290                 295                 300

Glu Ala Gly Lys Val Gly Glu Leu Cys Ala Gly Lys Glu Arg Arg Glu
305                 310                 315                 320

Ile Leu Gly Thr Cys Lys Met Leu Gly Gln Met Thr Asp Gln Val Ala
                325                 330                 335

Asp Leu Arg Ala Arg Gly Gln Gly Ser Ser Pro Val Ala Met Gln Lys
            340                 345                 350

Ala Gln Gln Val Ser Gln Gly Leu Asp Val Leu Thr Ala Lys Val Glu
            355                 360                 365

Asn Ala Ala Arg Lys Leu Glu Ala Met Thr Asn Ser Lys Gln Ser Ile
            370                 375                 380

Ala Lys Lys Ile Asp Ala Ala Gln Asn Trp Leu Ala Asp Pro Asn Gly
385                 390                 395                 400

Gly Pro Glu Gly Glu Glu Gln Ile Arg Gly Ala Leu Ala Glu Ala Arg
                405                 410                 415

Lys Ile Ala Glu Leu Cys Asp Asp Pro Lys Glu Arg Asp Asp Ile Leu
```

-continued

```
                420             425             430
Arg Ser Leu Gly Glu Ile Ser Ala Leu Thr Ser Lys Leu Ala Asp Leu
            435                 440                 445
Arg Arg Gln Gly Lys Gly Asp Ser Pro Glu Ala Arg Ala Leu Ala Lys
    450                 455                 460
Gln Val Ala Thr Ala Leu Gln Asn Leu Gln Thr Lys Thr Asn Arg Ala
465                 470                 475                 480
Val Ala Asn Ser Arg Pro Ala Lys Ala Val His Leu Glu Gly Lys
                485                 490                 495
Ile Glu Gln Ala Gln Arg Trp Ile Asp Asn Pro Thr Val Asp Asp Arg
            500                 505                 510
Gly Val Gly Gln Ala Ala Ile Arg Gly Leu Val Ala Glu Gly His Arg
        515                 520                 525
Leu Ala Asn Val Met Met Gly Pro Tyr Arg Gln Asp Leu Leu Ala Lys
        530                 535                 540
Cys Asp Arg Val Asp Gln Leu Thr Ala Gln Leu Ala Asp Leu Ala Ala
545                 550                 555                 560
Arg Gly Glu Gly Glu Ser Pro Gln Ala Arg Ala Leu Ala Ser Gln Leu
                565                 570                 575
Gln Asp Ser Leu Lys Asp Leu Lys Ala Arg Met Gln Glu Ala Met Thr
            580                 585                 590
Gln Glu Val Ser Asp Val Phe Ser Asp Thr Thr Thr Pro Ile Lys Leu
        595                 600                 605
Leu Ala Val Ala Ala Thr Ala Pro Pro Asp Ala Pro Asn Arg Glu Glu
        610                 615                 620
Val Phe Asp Glu Arg Ala Ala Asn Phe Glu Asn His Ser Gly Lys Leu
625                 630                 635                 640
Gly Ala Thr Ala Glu Lys Ala Ala Ala Val Gly Thr Ala Asn Lys Ser
                645                 650                 655
Thr Val Glu Gly Ile Gln Ala Ser Val Lys Thr Ala Arg Glu Leu Thr
            660                 665                 670
Pro Gln Val Val Ser Ala Ala Arg Ile Leu Leu Arg Asn Pro Gly Asn
        675                 680                 685
Gln Ala Ala Tyr Glu His Phe Glu Thr Met Lys Asn Gln Trp Ile Asp
        690                 695                 700
Asn Val Glu Lys Met Thr Gly Leu Val Asp Glu Ala Ile Asp Thr Lys
705                 710                 715                 720
Ser Leu Leu Asp Ala Ser Glu Glu Ala Ile Lys Lys Asp Leu Asp Lys
                725                 730                 735
Cys Lys Val Ala Met Ala Asn Ile Gln Pro Gln Met Leu Val Ala Gly
            740                 745                 750
Ala Thr Ser Ile Ala Arg Arg Ala Asn Arg Ile Leu Leu Val Ala Lys
        755                 760                 765
Arg Glu Val Glu Asn Ser Glu Asp Pro Lys Phe Arg Glu Ala Val Lys
    770                 775                 780
Ala Ala Ser Asp Glu Leu Ser Lys Thr Ile Ser Pro Met Val Met Asp
785                 790                 795                 800
Ala Lys Ala Val Ala Gly Asn Ile Ser Asp Pro Gly Leu Gln Lys Ser
                805                 810                 815
Phe Leu Asp Ser Gly Tyr Arg Ile Leu Gly Ala Val Ala Lys Val Arg
            820                 825                 830
Glu Ala Phe Gln Pro Gln Glu Pro Asp Phe Pro Pro Pro Pro Pro Asp
        835                 840                 845
```

```
Leu Glu Gln Leu Arg Leu Thr Asp Glu Leu Ala Pro Pro Lys Pro Pro
    850                 855                 860

Leu Pro Glu Gly Glu Val Pro Pro Pro Arg Pro Pro Pro Glu Glu
865                 870                 875                 880

Lys Asp Glu Glu Phe Pro Glu Gln Lys Ala Gly Glu Val Ile Asn Gln
                885                 890                 895

Pro Met Met Met Ala Ala Arg Gln Leu His Asp Glu Ala Arg Lys Trp
            900                 905                 910

Ser Ser Lys Gly Asn Asp Ile Ile Ala Ala Lys Arg Met Ala Leu
        915                 920                 925

Leu Met Ala Glu Met Ser Arg Leu Val Arg Gly Ser Gly Thr Lys
    930                 935                 940

Arg Ala Leu Ile Gln Cys Ala Lys Asp Ile Ala Lys Ala Ser Asp Glu
945                 950                 955                 960

Val Thr Arg Leu Ala Lys Glu Val Ala Lys Gln Cys Thr Asp Lys Arg
                965                 970                 975

Ile Arg Thr Asn Leu Leu Gln Val Cys Glu Arg Ile Pro Thr Ile Ser
            980                 985                 990

Thr Gln Leu Lys Ile Leu Ser Thr Val Lys Ala Thr Met Leu Gly Arg
        995                 1000                1005

Thr Asn Ile Ser Asp Glu Glu Ser Glu Gln Ala Thr Glu Met Leu Val
    1010                1015                1020

His Asn Ala Gln Asn Leu Met Gln Ser Val Lys Glu Thr Val Arg Glu
1025                1030                1035                1040

Ala Glu Ala Ala Ser Ile Lys Ile Arg Thr Asp Ala Gly Phe Thr Leu
                1045                1050                1055

Arg Trp Val Arg Lys Thr Pro Trp Tyr Gln
            1060                1065

<210> SEQ ID NO 32
<211> LENGTH: 333
<212> TYPE: DNA
<213> ORGANISM: Shigella flexneri
<220> FEATURE:
<223> OTHER INFORMATION: A524 / IpaA (524-633)

<400> SEQUENCE: 32
aaatcaaagg acattacaaa atccacaaca gaacatagaa taaacaacaa attaaaagtt      60
acagatgcaa atataagaaa ctacgtaaca gaaaccaacg cagatacaat tgataaaaat    120
catgcgatct atgaaaaggc aaaagaagta tctagcgccc tcagcaaggt attgtcaaaa    180
attgacgata cctctgcaga attacttaca gatgatatat ctgatttaaa aaataacaat    240
gatattacag ctgaaaacaa taatatatat aaagcagcaa agatgtaac cacttcccta    300 tcaaaagtat taaagaatat caataaggat taa                                  333

<210> SEQ ID NO 33
<211> LENGTH: 837
<212> TYPE: DNA
<213> ORGANISM: Artificial Sequence
<220> FEATURE:
<223> OTHER INFORMATION: Vinculin domain D1 (HVD1)

<400> SEQUENCE: 33
atgggcagca gccatcatca tcatcatcac agcagcggcc tggtgccgcg cggcagccat      60
atgccagtgt ttcatacgcg cacgatcgag agcatcctgg agccggtggc acagcagatc    120
```

| | |
|---|---:|
| tcccacctgg tgataatgca cgaggagggc gaggtggacg gcaaagccat tcctgacctc | 180 |
| accgcgcccg tggccgccgt gcaggcggcc gtcagcaacc tcgtccgggt tggaaaagag | 240 |
| actgttcaaa ccactgagga tcagattttg aagagagata tgccaccagc atttattaag | 300 |
| gttgagaatg cttgcaccaa gcttgtccag gcagctcaga tgcttcagtc agacccttac | 360 |
| tcagtgcctg ctcgagatta tctaattgat gggtcaaggg gcatcctctc tggaacatca | 420 |
| gacctgctcc ttaccttcga tgaggctgag gtccgtaaaa ttattagagt ttgcaaagga | 480 |
| attttggaat atcttacagt ggcagaggtg gtggagacta tggaagattt ggtcacttac | 540 |
| acaaagaatc ttgggccagg aatgactaag atggccaaga tgattgacga gagacagcag | 600 |
| gagctcactc accaggagca ccgagtgatg ttggtgaact cgatgaacac cgtgaaagag | 660 |
| ttgctgccag ttctcatttc agctatgaag attttttgtaa caactaaaaa ctcaaaaaac | 720 |
| caaggcatag aggaagcttt aaaaaatcgc aatttttactg tagaaaaaat gagtgctgaa | 780 |
| attaatgaga taattcgtgt gttacaactc acctcttggg atgaagatgc ctggtga | 837 |

<210> SEQ ID NO 34
<211> LENGTH: 1539
<212> TYPE: DNA
<213> ORGANISM: Artificial Sequence
<220> FEATURE:
<223> OTHER INFORMATION: Vinculin domains D1-D2 (HVD1D2)

<400> SEQUENCE: 34

| | |
|---|---:|
| atgggcagca gccatcatca tcatcatcac agcagcggcc tggtgccgcg cggcagccat | 60 |
| atgccagtgt tcatacgcg cacgatcgag agcatcctgg agccggtggc acagcagatc | 120 |
| tcccacctgg tgataatgca cgaggagggc gaggtggacg gcaaagccat tcctgacctc | 180 |
| accgcgcccg tggccgccgt gcaggcggcc gtcagcaacc tcgtccgggt tggaaaagag | 240 |
| actgttcaaa ccactgagga tcagattttg aagagagata tgccaccagc atttattaag | 300 |
| gttgagaatg cttgcaccaa gcttgtccag gcagctcaga tgcttcagtc agacccttac | 360 |
| tcagtgcctg ctcgagatta tctaattgat gggtcaaggg gcatcctctc tggaacatca | 420 |
| gacctgctcc ttaccttcga tgaggctgag gtccgtaaaa ttattagagt ttgcaaagga | 480 |
| attttggaat atcttacagt ggcagaggtg gtggagacta tggaagattt ggtcacttac | 540 |
| acaaagaatc ttgggccagg aatgactaag atggccaaga tgattgacga gagacagcag | 600 |
| gagctcactc accaggagca ccgagtgatg ttggtgaact cgatgaacac cgtgaaagag | 660 |
| ttgctgccag ttctcatttc agctatgaag attttttgtaa caactaaaaa ctcaaaaaac | 720 |
| caaggcatag aggaagcttt aaaaaatcgc aatttttactg tagaaaaaat gagtgctgaa | 780 |
| attaatgaga taattcgtgt gttacaactc acctcttggg atgaagatgc ctgggccagc | 840 |
| aaggacactg aagccatgaa gagagcattg gcctccatag actccaaact gaaccaggcc | 900 |
| aaaggttggc tccgtgaccc tagtgcctcc ccagggggatg ctggtgagca ggccatcaga | 960 |
| cagatcttag atgaagctgg aaaagttggt gaactctgtg caggcaaaga acgcagggag | 1020 |
| attctgggaa cttgcaaaat gctagggcag atgactgatc aagtggctga cctccgtgcc | 1080 |
| agaggacaag gatcctcacc ggtggccatg cagaaagctc agcaggtatc tcagggtctg | 1140 |
| gatgtgctca cagcaaaagt ggaaaatgca gctcgcaagc tggaagccat gaccaactca | 1200 |
| aagcagagca ttgcaaagaa gatcgatgct gctcagaact ggcttgcaga tccaaatggt | 1260 |
| ggaccggaag gagaagagca gattcgaggt gctttggctc aagctcggaa aatagcagaa | 1320 |
| ttatgtgatg atcctaaaga aagagatgac attctacgtt cccttgggga aatatctgct | 1380 |

```
ctgacttcta aattagcaga tctacgaaga caggggaaag gagattctcc agaggctcga    1440
gccttggcca acaggtggc cacggccctg cagaacctgc agaccaaaac caaccgggct    1500
gtggccaaca gcagaccggc caaagcagct gtacactga                           1539
```

<210> SEQ ID NO 35
<211> LENGTH: 512
<212> TYPE: PRT
<213> ORGANISM: Artificial Sequence
<220> FEATURE:
<223> OTHER INFORMATION: Vinculin domains D1-D2 (HVD1D2)

<400> SEQUENCE: 35

```
Met Gly Ser Ser His His His His His Ser Ser Gly Leu Val Pro
1               5                   10                  15

Arg Gly Ser His Met Pro Val Phe His Thr Arg Thr Ile Glu Ser Ile
            20                  25                  30

Leu Glu Pro Val Ala Gln Gln Ile Ser His Leu Val Ile Met His Glu
        35                  40                  45

Glu Gly Glu Val Asp Gly Lys Ala Ile Pro Asp Leu Thr Ala Pro Val
    50                  55                  60

Ala Ala Val Gln Ala Ala Val Ser Asn Leu Val Arg Val Gly Lys Glu
65                  70                  75                  80

Thr Val Gln Thr Thr Glu Asp Gln Ile Leu Lys Arg Asp Met Pro Pro
                85                  90                  95

Ala Phe Ile Lys Val Glu Asn Ala Cys Thr Lys Leu Val Gln Ala Ala
            100                 105                 110

Gln Met Leu Gln Ser Asp Pro Tyr Ser Val Pro Ala Arg Asp Tyr Leu
        115                 120                 125

Ile Asp Gly Ser Arg Gly Ile Leu Ser Gly Thr Ser Asp Leu Leu Leu
    130                 135                 140

Thr Phe Asp Glu Ala Glu Val Arg Lys Ile Ile Arg Val Cys Lys Gly
145                 150                 155                 160

Ile Leu Glu Tyr Leu Thr Val Ala Glu Val Val Glu Thr Met Glu Asp
                165                 170                 175

Leu Val Thr Tyr Thr Lys Asn Leu Gly Pro Gly Met Thr Lys Met Ala
            180                 185                 190

Lys Met Ile Asp Glu Arg Gln Gln Glu Leu Thr His Gln Glu His Arg
        195                 200                 205

Val Met Leu Val Asn Ser Met Asn Thr Val Lys Glu Leu Leu Pro Val
    210                 215                 220

Leu Ile Ser Ala Met Lys Ile Phe Val Thr Thr Lys Asn Ser Lys Asn
225                 230                 235                 240

Gln Gly Ile Glu Glu Ala Leu Lys Asn Arg Asn Phe Thr Val Glu Lys
                245                 250                 255

Met Ser Ala Glu Ile Asn Glu Ile Ile Arg Val Leu Gln Leu Thr Ser
            260                 265                 270

Trp Asp Glu Asp Ala Trp Ala Ser Lys Asp Thr Glu Ala Met Lys Arg
        275                 280                 285

Ala Leu Ala Ser Ile Asp Ser Lys Leu Asn Gln Ala Lys Gly Trp Leu
    290                 295                 300

Arg Asp Pro Ser Ala Ser Pro Gly Asp Ala Gly Glu Gln Ala Ile Arg
305                 310                 315                 320

Gln Ile Leu Asp Glu Ala Gly Lys Val Gly Glu Leu Cys Ala Gly Lys
                325                 330                 335
```

Glu Arg Arg Glu Ile Leu Gly Thr Cys Lys Met Leu Gly Gln Met Thr
            340                 345                 350

Asp Gln Val Ala Asp Leu Arg Ala Arg Gly Gln Gly Ser Ser Pro Val
        355                 360                 365

Ala Met Gln Lys Ala Gln Val Ser Gln Gly Leu Asp Val Leu Thr
    370                 375                 380

Ala Lys Val Glu Asn Ala Ala Arg Lys Leu Glu Ala Met Thr Asn Ser
385                 390                 395                 400

Lys Gln Ser Ile Ala Lys Lys Ile Asp Ala Ala Gln Asn Trp Leu Ala
                405                 410                 415

Asp Pro Asn Gly Gly Pro Glu Gly Glu Gln Ile Arg Gly Ala Leu
            420                 425                 430

Ala Glu Ala Arg Lys Ile Ala Glu Leu Cys Asp Asp Pro Lys Glu Arg
            435                 440                 445

Asp Asp Ile Leu Arg Ser Leu Gly Glu Ile Ser Ala Leu Thr Ser Lys
    450                 455                 460

Leu Ala Asp Leu Arg Arg Gln Gly Lys Gly Asp Ser Pro Glu Ala Arg
465                 470                 475                 480

Ala Leu Ala Lys Gln Val Ala Thr Ala Leu Gln Asn Leu Gln Thr Lys
                485                 490                 495

Thr Asn Arg Ala Val Ala Asn Ser Arg Pro Ala Lys Ala Ala Val His
            500                 505                 510

<210> SEQ ID NO 36
<211> LENGTH: 512
<212> TYPE: PRT
<213> ORGANISM: Artificial Sequence
<220> FEATURE:
<223> OTHER INFORMATION: Vinculin domains D1-D2 (HVD1D2) K276R

<400> SEQUENCE: 36

Met Gly Ser Ser His His His His His His Ser Ser Gly Leu Val Pro
1               5                   10                  15

Arg Gly Ser His Met Pro Val Phe His Thr Arg Thr Ile Glu Ser Ile
            20                  25                  30

Leu Glu Pro Val Ala Gln Gln Ile Ser His Leu Val Ile Met His Glu
        35                  40                  45

Glu Gly Glu Val Asp Gly Lys Ala Ile Pro Asp Leu Thr Ala Pro Val
    50                  55                  60

Ala Ala Val Gln Ala Ala Val Ser Asn Leu Val Arg Val Gly Lys Glu
65                  70                  75                  80

Thr Val Gln Thr Thr Glu Asp Gln Ile Leu Lys Arg Asp Met Pro Pro
                85                  90                  95

Ala Phe Ile Lys Val Glu Asn Ala Cys Thr Lys Leu Val Gln Ala Ala
            100                 105                 110

Gln Met Leu Gln Ser Asp Pro Tyr Ser Val Pro Ala Arg Asp Tyr Leu
        115                 120                 125

Ile Asp Gly Ser Arg Gly Ile Leu Ser Gly Thr Ser Asp Leu Leu Leu
    130                 135                 140

Thr Phe Asp Glu Ala Glu Val Arg Lys Ile Ile Arg Val Cys Lys Gly
145                 150                 155                 160

Ile Leu Glu Tyr Leu Thr Val Ala Glu Val Val Glu Thr Met Glu Asp
                165                 170                 175

Leu Val Thr Tyr Thr Lys Asn Leu Gly Pro Gly Met Thr Lys Met Ala
            180                 185                 190

```
Lys Met Ile Asp Glu Arg Gln Gln Glu Leu Thr His Gln Glu His Arg
            195                 200                 205

Val Met Leu Val Asn Ser Met Asn Thr Val Lys Glu Leu Leu Pro Val
        210                 215                 220

Leu Ile Ser Ala Met Lys Ile Phe Val Thr Thr Lys Asn Ser Lys Asn
225                 230                 235                 240

Gln Gly Ile Glu Glu Ala Leu Lys Asn Arg Asn Phe Thr Val Glu Lys
                245                 250                 255

Met Ser Ala Glu Ile Asn Glu Ile Ile Arg Val Leu Gln Leu Thr Ser
            260                 265                 270

Trp Asp Glu Asp Ala Trp Ala Ser Lys Asp Thr Glu Ala Met Lys Arg
        275                 280                 285

Ala Leu Ala Ser Ile Asp Ser Arg Leu Asn Gln Ala Lys Gly Trp Leu
            290                 295                 300

Arg Asp Pro Ser Ala Ser Pro Gly Asp Ala Gly Glu Gln Ala Ile Arg
305                 310                 315                 320

Gln Ile Leu Asp Glu Ala Gly Lys Val Gly Glu Leu Cys Ala Gly Lys
                325                 330                 335

Glu Arg Arg Glu Ile Leu Gly Thr Cys Lys Met Leu Gly Gln Met Thr
            340                 345                 350

Asp Gln Val Ala Asp Leu Arg Ala Arg Gly Gln Gly Ser Ser Pro Val
        355                 360                 365

Ala Met Gln Lys Ala Gln Gln Val Ser Gln Gly Leu Asp Val Leu Thr
        370                 375                 380

Ala Lys Val Glu Asn Ala Ala Arg Lys Leu Glu Ala Met Thr Asn Ser
385                 390                 395                 400

Lys Gln Ser Ile Ala Lys Lys Ile Asp Ala Ala Gln Asn Trp Leu Ala
                405                 410                 415

Asp Pro Asn Gly Gly Pro Glu Gly Glu Glu Gln Ile Arg Gly Ala Leu
            420                 425                 430

Ala Glu Ala Arg Lys Ile Ala Glu Leu Cys Asp Asp Pro Lys Glu Arg
        435                 440                 445

Asp Asp Ile Leu Arg Ser Leu Gly Glu Ile Ser Ala Leu Thr Ser Lys
        450                 455                 460

Leu Ala Asp Leu Arg Arg Gln Gly Lys Gly Asp Ser Pro Glu Ala Arg
465                 470                 475                 480

Ala Leu Ala Lys Gln Val Ala Thr Ala Leu Gln Asn Leu Gln Thr Lys
                485                 490                 495

Thr Asn Arg Ala Val Ala Asn Ser Arg Pro Ala Lys Ala Ala Val His
            500                 505                 510

<210> SEQ ID NO 37
<211> LENGTH: 512
<212> TYPE: PRT
<213> ORGANISM: Artificial Sequence
<220> FEATURE:
<223> OTHER INFORMATION: Vinculin domains D1-D2 (HVD1D2) E305Q

<400> SEQUENCE: 37

Met Gly Ser Ser His His His His His His Ser Ser Gly Leu Val Pro
1               5                   10                  15

Arg Gly Ser His Met Pro Val Phe His Thr Arg Thr Ile Glu Ser Ile
                20                  25                  30

Leu Glu Pro Val Ala Gln Gln Ile Ser His Leu Val Ile Met His Glu
            35                  40                  45
```

```
Glu Gly Glu Val Asp Gly Lys Ala Ile Pro Asp Leu Thr Ala Pro Val
        50                  55                  60

Ala Ala Val Gln Ala Val Ser Asn Leu Val Arg Val Gly Lys Glu
65                  70                  75                  80

Thr Val Gln Thr Thr Glu Asp Gln Ile Leu Lys Arg Asp Met Pro Pro
                85                  90                  95

Ala Phe Ile Lys Val Glu Asn Ala Cys Thr Lys Leu Val Gln Ala Ala
                100                 105                 110

Gln Met Leu Gln Ser Asp Pro Tyr Ser Val Pro Ala Arg Asp Tyr Leu
            115                 120                 125

Ile Asp Gly Ser Arg Gly Ile Leu Ser Gly Thr Ser Asp Leu Leu
130                 135                 140

Thr Phe Asp Glu Ala Glu Val Arg Lys Ile Ile Arg Val Cys Lys Gly
145                 150                 155                 160

Ile Leu Glu Tyr Leu Thr Val Ala Glu Val Val Glu Thr Met Glu Asp
                165                 170                 175

Leu Val Thr Tyr Thr Lys Asn Leu Gly Pro Gly Met Thr Lys Met Ala
            180                 185                 190

Lys Met Ile Asp Glu Arg Gln Gln Glu Leu Thr His Gln His Arg
        195                 200                 205

Val Met Leu Val Asn Ser Met Asn Thr Val Lys Glu Leu Leu Pro Val
210                 215                 220

Leu Ile Ser Ala Met Lys Ile Phe Val Thr Thr Lys Asn Ser Lys Asn
225                 230                 235                 240

Gln Gly Ile Glu Glu Ala Leu Lys Asn Arg Asn Phe Thr Val Glu Lys
                245                 250                 255

Met Ser Ala Glu Ile Asn Glu Ile Ile Arg Val Leu Gln Leu Thr Ser
            260                 265                 270

Trp Asp Glu Asp Ala Trp Ala Ser Lys Asp Thr Glu Ala Met Lys Arg
        275                 280                 285

Ala Leu Ala Ser Ile Asp Ser Lys Leu Asn Gln Ala Lys Gly Trp Leu
290                 295                 300

Arg Asp Pro Ser Ala Ser Pro Gly Asp Ala Gly Glu Gln Ala Ile Arg
305                 310                 315                 320

Gln Ile Leu Asp Gln Ala Gly Lys Val Gly Glu Leu Cys Ala Gly Lys
                325                 330                 335

Glu Arg Arg Glu Ile Leu Gly Thr Cys Lys Met Leu Gly Gln Met Thr
            340                 345                 350

Asp Gln Val Ala Asp Leu Arg Ala Arg Gly Gln Gly Ser Ser Pro Val
        355                 360                 365

Ala Met Gln Lys Ala Gln Gln Val Ser Gln Gly Leu Asp Val Leu Thr
370                 375                 380

Ala Lys Val Glu Asn Ala Ala Arg Lys Leu Glu Ala Met Thr Asn Ser
385                 390                 395                 400

Lys Gln Ser Ile Ala Lys Lys Ile Asp Ala Ala Gln Asn Trp Leu Ala
                405                 410                 415

Asp Pro Asn Gly Gly Pro Glu Gly Glu Glu Gln Ile Arg Gly Ala Leu
            420                 425                 430

Ala Glu Ala Arg Lys Ile Ala Glu Leu Cys Asp Asp Pro Lys Glu Arg
        435                 440                 445

Asp Asp Ile Leu Arg Ser Leu Gly Glu Ile Ser Ala Leu Thr Ser Lys
450                 455                 460
```

Leu Ala Asp Leu Arg Arg Gln Gly Lys Gly Asp Ser Pro Glu Ala Arg
465                 470                 475                 480

Ala Leu Ala Lys Gln Val Ala Thr Ala Leu Gln Asn Leu Gln Thr Lys
            485                 490                 495

Thr Asn Arg Ala Val Ala Asn Ser Arg Pro Ala Lys Ala Ala Val His
        500                 505                 510

<210> SEQ ID NO 38
<211> LENGTH: 155
<212> TYPE: PRT
<213> ORGANISM: Homo sapiens
<220> FEATURE:
<223> OTHER INFORMATION: Talin-1 VBS1 (482-636)

<400> SEQUENCE: 38

Arg Gly His Met Pro Pro Leu Thr Ser Ala Gln Gln Ala Leu Thr Gly
1               5                   10                  15

Thr Ile Asn Ser Ser Met Gln Ala Val Gln Ala Ala Gln Ala Thr Leu
            20                  25                  30

Asp Asp Phe Asp Thr Leu Pro Pro Leu Gly Gln Asp Ala Ala Ser Lys
        35                  40                  45

Ala Trp Arg Lys Asn Lys Met Asp Glu Ser Lys His Glu Ile His Ser
    50                  55                  60

Gln Val Asp Ala Ile Thr Ala Gly Thr Ala Ser Val Val Asn Leu Thr
65                  70                  75                  80

Ala Gly Asp Pro Ala Glu Thr Asp Tyr Thr Ala Val Gly Cys Ala Val
                85                  90                  95

Thr Thr Ile Ser Ser Asn Leu Thr Glu Met Ser Arg Gly Val Lys Leu
            100                 105                 110

Leu Ala Ala Leu Leu Glu Asp Glu Gly Gly Ser Gly Arg Pro Leu Leu
        115                 120                 125

Gln Ala Ala Lys Gly Leu Ala Gly Ala Val Ser Glu Leu Leu Arg Ser
    130                 135                 140

Ala Gln Pro Ala Ser Ala Glu Pro Arg Gln Asn
145                 150                 155

<210> SEQ ID NO 39
<211> LENGTH: 26
<212> TYPE: PRT
<213> ORGANISM: Homo sapiens
<220> FEATURE:
<223> OTHER INFORMATION: Talin-1 VBS2 (1944-1969)

<400> SEQUENCE: 39

Ala Tyr Thr Lys Lys Glu Leu Ile Glu Cys Ala Arg Arg Val Ser Glu
1               5                   10                  15

Lys Val Ser His Val Leu Ala Ala Leu Gln
            20                  25

<210> SEQ ID NO 40
<211> LENGTH: 9
<212> TYPE: PRT
<213> ORGANISM: Shigella flexneri
<220> FEATURE:
<223> OTHER INFORMATION: N-ter Domain

<400> SEQUENCE: 40

Gly Asp Thr Tyr Leu Thr Arg Glu Thr
1               5

```
<210> SEQ ID NO 41
<211> LENGTH: 55
<212> TYPE: PRT
<213> ORGANISM: Shigella flexneri
<220> FEATURE:
<223> OTHER INFORMATION: Interdomain VBS3-VBS2

<400> SEQUENCE: 41

Gly Thr Lys Ser Gly Thr Gln Glu Arg Glu Leu Gln Glu Lys Ser Lys
1               5                   10                  15

Asp Ile Thr Lys Ser Thr Thr Glu His Arg Ile Asn Asn Lys Leu Lys
            20                  25                  30

Val Thr Asp Ala Asn Ile Arg Asn Tyr Val Thr Glu Thr Asn Ala Asp
        35                  40                  45

Thr Ile Asp Lys Asn His Ala
    50                  55

<210> SEQ ID NO 42
<211> LENGTH: 27
<212> TYPE: PRT
<213> ORGANISM: Shigella flexneri
<220> FEATURE:
<223> OTHER INFORMATION: Interdomain VBS2-VBS1

<400> SEQUENCE: 42

Asp Asp Thr Ser Ala Glu Leu Leu Thr Asp Asp Ile Ser Asp Leu Lys
1               5                   10                  15

Asn Asn Asn Asp Ile Thr Ala Glu Asn Asn Asn
            20                  25

<210> SEQ ID NO 43
<211> LENGTH: 481
<212> TYPE: PRT
<213> ORGANISM: Shigella sonnei
<220> FEATURE:
<223> OTHER INFORMATION: SipA

<400> SEQUENCE: 43

Asn Ile Glu His Arg Leu Ala Leu Leu Ala Gln Gln His Thr Ser Gly
1               5                   10                  15

Glu Ala Leu Ser Leu Gly Gln Lys Leu Leu Asn Thr Glu Val Ser Ser
            20                  25                  30

Phe Ile Lys Asn Asn Ile Leu Ala Glu Leu Lys Leu Ser Asn Glu Thr
        35                  40                  45

Val Ser Ser Leu Lys Leu Asp Asp Leu Val Asp Ala Gln Ala Lys Leu
    50                  55                  60

Ala Phe Asp Ser Leu Arg Asn Gln Arg Lys Asn Thr Ile Asp Ser Lys
65                  70                  75                  80

Gly Phe Gly Ile Gly Lys Leu Ser Arg Asp Leu Asn Thr Val Ala Val
                85                  90                  95

Phe Pro Glu Leu Leu Arg Lys Val Leu Asn Asp Ile Leu Glu Asp Ile
            100                 105                 110

Lys Asp Ser His Pro Ile Gln Asp Gly Leu Pro Thr Pro Pro Glu Asp
        115                 120                 125

Met Pro Asp Gly Gly Pro Thr Pro Gly Ala Asn Glu Lys Thr Ser Gln
    130                 135                 140

Pro Val Ile His Tyr His Ile Asn Asn Asp Asn Arg Thr Tyr Asp Asn
145                 150                 155                 160

Arg Val Phe Asp Asn Arg Val Tyr Asp Asn Ser Tyr His Glu Asn Pro
                165                 170                 175
```

Glu Asn Asp Ala Gln Ser Pro Thr Ser Gln Thr Asn Asp Leu Leu Ser
            180                 185                 190

Arg Asn Gly Asn Ser Leu Leu Asn Pro Gln Arg Ala Leu Val Gln Lys
            195                 200                 205

Val Thr Ser Val Leu Pro His Ser Ile Ser Asp Thr Val Gln Thr Phe
210                 215                 220

Ala Asn Asn Ser Ala Leu Glu Lys Val Phe Asn His Thr Pro Asp Asn
225                 230                 235                 240

Ser Asp Gly Ile Gly Ser Asp Leu Leu Thr Thr Ser Ser Gln Glu Arg
                245                 250                 255

Ser Ala Asn Asn Ser Leu Ser Arg Gly His Arg Pro Leu Asn Ile Gln
            260                 265                 270

Asn Ser Ser Thr Thr Pro Pro Leu His Pro Glu Gly Val Thr Ser Ser
            275                 280                 285

Asn Asp Asn Ser Ser Asp Thr Thr Lys Ser Ser Ala Ser Leu Ser His
            290                 295                 300

Arg Val Ala Ser Gln Ile Asn Lys Phe Asn Ser Asn Thr Asp Ser Lys
305                 310                 315                 320

Val Leu Gln Thr Asp Phe Phe Ser Arg Asn Gly Asp Thr Tyr Leu Thr
                325                 330                 335

Arg Glu Thr Ile Phe Glu Ala Ser Lys Lys Val Thr Asn Ser Leu Ser
            340                 345                 350

Asn Leu Ile Ser Leu Ile Gly Thr Lys Ser Gly Thr Gln Glu Arg Glu
            355                 360                 365

Leu Gln Glu Lys Ser Lys Asp Ile Thr Lys Ser Thr Thr Glu His Arg
            370                 375                 380

Ile Asn Asn Lys Leu Lys Val Thr Asp Ala Asn Thr Ile Asn Tyr Val
385                 390                 395                 400

Thr Glu Thr Asn Ala Asp Thr Ile Asp Lys Asn His Ala Ile Tyr Glu
                405                 410                 415

Lys Ala Lys Glu Val Ser Ser Ala Leu Ser Lys Val Leu Ser Lys Ile
            420                 425                 430

Asp Asp Thr Ser Ala Glu Leu Leu Thr Asp Asp Ile Ser Asp Leu Lys
            435                 440                 445

Asn Asn Asn Asp Ile Thr Ala Glu Asn Asn Ile Tyr Lys Ala Ala
            450                 455                 460

Lys Asp Val Thr Thr Ser Leu Ser Lys Val Leu Lys Asn Ile Asn Lys
465                 470                 475                 480

Asp

<210> SEQ ID NO 44
<211> LENGTH: 500
<212> TYPE: PRT
<213> ORGANISM: Shigella sonnei
<220> FEATURE:
<223> OTHER INFORMATION: SipA

<400> SEQUENCE: 44

Val Ala Gln Tyr Ser Glu Leu Ile Ile Lys Asp Lys Leu Ser Gln Asp
1               5                   10                  15

Ser Ala Phe Gly Pro Trp Ser Ala Lys Asn Lys Lys Leu His Gln Leu
            20                  25                  30

Arg Gln Asn Ile Glu His Arg Leu Ala Leu Leu Ala Gln Gln His Thr
            35                  40                  45

```
Ser Gly Glu Ala Leu Ser Leu Gly Gln Lys Leu Leu Asn Thr Glu Val
 50                  55                  60

Ser Ser Phe Ile Lys Asn Asn Ile Leu Ala Glu Leu Lys Leu Ser Asn
 65                  70                  75                  80

Glu Thr Val Ser Ser Leu Lys Leu Asp Asp Leu Val Asp Ala Gln Ala
                 85                  90                  95

Lys Leu Ala Phe Asp Ser Leu Arg Asn Gln Arg Lys Asn Thr Ile Asp
                100                 105                 110

Ser Lys Gly Phe Gly Ile Gly Lys Leu Ser Arg Asp Leu Asn Thr Val
                115                 120                 125

Ala Val Phe Pro Glu Leu Leu Arg Lys Val Leu Asn Asp Ile Leu Glu
130                 135                 140

Asp Ile Lys Asp Ser His Pro Ile Gln Asp Gly Leu Pro Thr Pro Pro
145                 150                 155                 160

Glu Asp Met Pro Asp Gly Gly Pro Thr Pro Gly Ala Asn Glu Lys Thr
                165                 170                 175

Ser Gln Pro Val Ile His Tyr His Ile Asn Asn Asp Asn Arg Thr Tyr
                180                 185                 190

Asp Asn Arg Val Phe Asp Asn Arg Val Tyr Asp Asn Ser Tyr His Glu
                195                 200                 205

Asn Pro Glu Asn Asp Ala Gln Ser Pro Thr Ser Gln Thr Asn Asp Leu
210                 215                 220

Leu Ser Arg Asn Gly Asn Ser Leu Leu Asn Pro Gln Arg Ala Leu Val
225                 230                 235                 240

Gln Lys Val Thr Ser Val Leu Pro His Ser Ile Ser Asp Thr Val Gln
                245                 250                 255

Thr Phe Ala Asn Asn Ser Ala Leu Glu Lys Val Phe Asn His Thr Pro
                260                 265                 270

Asp Asn Ser Asp Gly Ile Gly Ser Asp Leu Leu Thr Thr Ser Ser Gln
                275                 280                 285

Glu Arg Ser Ala Asn Asn Ser Leu Ser Arg Gly His Arg Pro Leu Asn
                290                 295                 300

Ile Gln Asn Ser Ser Thr Thr Pro Pro Leu His Pro Glu Gly Val Thr
305                 310                 315                 320

Ser Ser Asn Asp Asn Ser Ser Asp Thr Thr Lys Ser Ser Ala Ser Leu
                325                 330                 335

Ser His Arg Val Ala Ser Gln Ile Asn Lys Phe Asn Ser Asn Thr Asp
                340                 345                 350

Ser Lys Val Leu Gln Thr Asp Phe Phe Ser Arg Asn Gly Asp Thr Tyr
                355                 360                 365

Leu Thr Arg Glu Thr Ile Phe Glu Ala Ser Lys Lys Val Thr Asn Ser
370                 375                 380

Leu Ser Asn Leu Ile Ser Leu Ile Gly Thr Lys Ser Gly Thr Gln Glu
385                 390                 395                 400

Arg Glu Leu Gln Glu Lys Ser Lys Asp Ile Thr Lys Ser Thr Thr Glu
                405                 410                 415

His Arg Ile Asn Asn Lys Leu Lys Val Thr Asp Ala Asn Thr Ile Asn
                420                 425                 430

Tyr Val Thr Glu Thr Asn Ala Asp Thr Ile Asp Lys Asn His Ala Ile
                435                 440                 445

Tyr Glu Lys Ala Lys Glu Val Ser Ser Ala Leu Ser Lys Val Leu Ser
450                 455                 460

Lys Ile Asp Asp Thr Ser Ala Glu Leu Leu Thr Asp Asp Ile Ser Asp
```

```
                465                 470                 475                 480
Leu Lys Asn Asn Asn Asp Ile Thr Ala Glu Asn Asn Asn Ile Tyr Lys
                    485                 490                 495

Ala Ala Lys Asp
            500

<210> SEQ ID NO 45
<211> LENGTH: 587
<212> TYPE: PRT
<213> ORGANISM: Shigella sonnei 53G
<220> FEATURE:
<223> OTHER INFORMATION: YopE

<400> SEQUENCE: 45

Met Ser Glu Lys Glu Ser Phe Ala Thr Ser Phe Asn Gln Lys Cys Leu
1               5                   10                  15

Asp Phe Leu Phe Ser Ser Ser Gly Lys Glu Asp Val Leu Arg Ser Ile
                20                  25                  30

Tyr Ser Asn Ser Met Asn Ala Tyr Ala Lys Ser Glu Ile Leu Glu Phe
            35                  40                  45

Ser Asn Val Leu Tyr Ser Leu Val His Gln Asn Gly Leu Asn Phe Glu
        50                  55                  60

Asn Glu Lys Gly Leu Gln Lys Ile Val Ala Gln Tyr Ser Glu Leu Ile
65                  70                  75                  80

Ile Lys Asp Lys Leu Ser Gln Asp Ser Ala Phe Gly Pro Trp Ser Ala
                85                  90                  95

Lys Asn Lys Lys Leu His Gln Leu Arg Gln Asn Ile Glu His Arg Leu
            100                 105                 110

Ala Leu Leu Ala Gln Gln His Thr Ser Gly Glu Ala Leu Ser Leu Gly
        115                 120                 125

Gln Lys Leu Leu Asn Thr Glu Val Ser Ser Phe Ile Lys Asn Asn Ile
    130                 135                 140

Leu Ala Glu Leu Lys Leu Ser Asn Glu Thr Val Ser Ser Leu Lys Leu
145                 150                 155                 160

Asp Asp Leu Val Asp Ala Gln Ala Lys Leu Ala Phe Asp Ser Leu Arg
                165                 170                 175

Asn Gln Arg Lys Asn Thr Ile Asp Ser Lys Gly Phe Gly Ile Gly Lys
            180                 185                 190

Leu Ser Arg Asp Leu Asn Thr Val Ala Val Phe Pro Glu Leu Leu Arg
        195                 200                 205

Lys Val Leu Asn Asp Ile Leu Glu Asp Ile Lys Asp Ser His Pro Ile
    210                 215                 220

Gln Asp Gly Leu Pro Thr Pro Glu Asp Met Pro Asp Gly Gly Pro
225                 230                 235                 240

Thr Pro Gly Ala Asn Glu Lys Thr Ser Gln Pro Val Ile His Tyr His
                245                 250                 255

Ile Asn Asn Asp Asn Arg Thr Tyr Asp Asn Arg Val Phe Asp Asn Arg
            260                 265                 270

Val Tyr Asp Asn Ser Tyr His Glu Asn Pro Glu Asn Asp Ala Gln Ser
        275                 280                 285

Pro Thr Ser Gln Thr Asn Asp Leu Leu Ser Arg Asn Gly Asn Ser Leu
    290                 295                 300

Leu Asn Pro Gln Arg Ala Leu Val Gln Lys Val Thr Ser Val Leu Pro
305                 310                 315                 320

His Ser Ile Ser Asp Thr Val Gln Thr Phe Ala Asn Asn Ser Ala Leu
```

```
                    325                 330                 335
Glu Lys Val Phe Asn His Thr Pro Asp Asn Ser Asp Gly Ile Gly Ser
                340                 345                 350

Asp Leu Leu Thr Thr Ser Ser Gln Glu Arg Ser Ala Asn Asn Ser Leu
            355                 360                 365

Ser Arg Gly His Arg Pro Leu Asn Ile Gln Asn Ser Ser Thr Thr Pro
370                 375                 380

Pro Leu His Pro Glu Gly Val Thr Ser Ser Asn Asp Asn Ser Ser Asp
385                 390                 395                 400

Thr Thr Lys Ser Ser Ala Ser Leu Ser His Arg Val Ala Ser Gln Ile
                405                 410                 415

Asn Lys Phe Asn Ser Asn Thr Asp Ser Lys Val Leu Gln Thr Asp Phe
                420                 425                 430

Phe Ser Arg Asn Gly Asp Thr Tyr Leu Thr Arg Glu Thr Ile Phe Glu
                435                 440                 445

Ala Ser Lys Lys Val Thr Asn Ser Leu Ser Asn Leu Ile Ser Leu Ile
450                 455                 460

Gly Thr Lys Ser Gly Thr Gln Glu Arg Glu Leu Gln Glu Lys Ser Lys
465                 470                 475                 480

Asp Ile Thr Lys Ser Thr Thr Glu His Arg Ile Asn Asn Lys Leu Lys
                485                 490                 495

Val Thr Asp Ala Asn Thr Ile Asn Tyr Val Thr Glu Thr Asn Ala Asp
                500                 505                 510

Thr Ile Asp Lys Asn His Ala Ile Tyr Glu Lys Ala Lys Glu Val Ser
                515                 520                 525

Ser Ala Leu Ser Lys Val Leu Ser Lys Ile Asp Asp Thr Ser Ala Glu
            530                 535                 540

Leu Leu Thr Asp Asp Ile Ser Asp Leu Lys Asn Asn Asn Asp Ile Thr
545                 550                 555                 560

Ala Glu Asn Asn Asn Ile Tyr Lys Ala Ala Lys Asp Val Thr Thr Ser
                565                 570                 575

Leu Ser Lys Val Leu Lys Asn Ile Asn Lys Asp
            580                 585

<210> SEQ ID NO 46
<211> LENGTH: 1902
<212> TYPE: DNA
<213> ORGANISM: Shigella flexneri 6
<220> FEATURE:
<223> OTHER INFORMATION: pINV_F6_M1382 (3109-5010)

<400> SEQUENCE: 46
ttaatcctta ttgatattct ttaatacttt tgatagggaa gtggttacat cttttgctgc      60
tttatatata ttattgtttt cagctgtaat atcattgtta ttttttaaat cagatatatc     120
atctgtaagt aattctgcag aggtatcgtc aattttttgac aataccttgc tgagggcgct    180
agatacttct tttgcctttt catagatcgc atgattttta tcaattgtat ctgcgttggt     240
ttctgttacg tagtttattg tatttgcatc tgtaactttt aatttgttgt ttattctgtg     300
ttctgttgtg gattttgtaa tgtcctttga ttttcctgt aactctcgtt cttgtgttcc      360
tgatttagtt ccaatgagag atataagatt acttagggag tttgttactt tttttgaagc    420
ttcaaatatc gtttcccgtg ttaaatatgt gtctccattt cttgataaaa aatcagtctg     480
aagtactttt gaatcagtgt ttgagttgaa ttattgatt tgcgaagcta ctctatgaga     540
aagagaagcg ctacttttag ttgtatctga tgagttatca ttactgcttg tcactccttc    600
```

```
cgggtggaga ggggggggtgg ttgaagagtt ctgtatgttc agaggcctgt gtccccgaga    660
aagagagtta tttgtagatc tttcttgact actcgtagtt aacaggtctg aacctattcc    720
atccgaatta tctggagtat ggttgaaaac ctttctaaa gctgaattat ttgcaaatgt     780
ctggacagca tctgatatag agtgtggtag aacggaagtt acttttgaa ctagtgctct     840 ttgtggattt agtaatgagt ttccgttacg ggataataga tcgtttgtct gagaagtagg    900
agactgtgca tcatttctg ggttctcgtg atagctattg tcatatactc tgttgtcaaa     960
aactctatta tcgtaagttc tattatcatt atttatatga tagtgaatta caggttggga   1020
tgttttctca ttggctccgg ggttggtcc gccatctggc atatcttcgg gaggtgtagg    1080
gaggccatct tggataggat gcgaatcttt tatatcttct aaaatatcat taaggacttt   1140
tctcaacagc tcaggaaaca cggctactgt atttaagtct cttgacagtt tacctatacc   1200
aaatccttta ctatcaatag tatttttacg ttgattgcgc aaactatcaa aggcaagttt   1260
tgcctgtgcg tcaactaaat catctagttt gagagatgaa acagtttcat tacttaactt   1320
taattcagca agaatattat tcttgataaa tgatgatact tcagtattga ggagttttg    1380 tcccaatgat aaagcttcac cagatgtgtg ttgttgtgct aatagtgcaa gtctgtgctc   1440
aatgttttgt cgtaattgat ggagtttctt attctttgcc gaccatggtc caaaggcaga   1500
atcttgggat aatttatctt ttataattag ttccgaatac tgtgcgacaa tttttgaag    1560 tcccttttcg ttttcaaaat taagatcatt ttgatgtact aaggagtaca aacatttga    1620 aaattcgaga atctcgcttt tggcatacgc attcattgag ttggaataaa tgcttcttaa   1680
cacatcttct ttccctgagg aagaaaataa aaatcaaga catttctgat taaaagacgt    1740
tgcaaagttt tcttttcag acactgatgc tggtgttttt agagaagttt gcgaactatg    1800
gatatcggat attttgcttt ttaactcgct gtattctgtt gatgatggtg aagttgcctt   1860
atataagaat gttggcgctt gagtattatt tacattatgc at                      1902
```

<210> SEQ ID NO 47
<211> LENGTH: 20
<212> TYPE: PRT
<213> ORGANISM: Chlamydia trachomatis L2
<220> FEATURE:
<223> OTHER INFORMATION: TarP VBS1

<400> SEQUENCE: 47

Leu Phe Gln Ala Ala Thr Gln Thr Thr Gln Ala Leu Ser Ser Leu Ile
1               5                   10                  15

Asp Thr Val Gly
            20

<210> SEQ ID NO 48
<211> LENGTH: 24
<212> TYPE: PRT
<213> ORGANISM: Chlamydia trachomatis L2
<220> FEATURE:
<223> OTHER INFORMATION: TarP VBS2

<400> SEQUENCE: 48

Leu Phe Gln Ala Ala Ala Val Thr Gln Ala Leu Gly Asn Val Ala Gly
1               5                   10                  15

Lys Val Asn Leu Ala Ile Gln Gly
            20

<210> SEQ ID NO 49

```
<211> LENGTH: 19
<212> TYPE: PRT
<213> ORGANISM: Chlamydophila caviae GPIC
<220> FEATURE:
<223> OTHER INFORMATION: TarP VBS1

<400> SEQUENCE: 49

Leu Leu Glu Ala Ala Arg Asn Thr Thr Thr Met Leu Ser Lys Thr Leu
1               5                   10                  15

Ser Lys Val

<210> SEQ ID NO 50
<211> LENGTH: 19
<212> TYPE: PRT
<213> ORGANISM: Chlamydophila caviae GPIC
<220> FEATURE:
<223> OTHER INFORMATION: TarP VBS2

<400> SEQUENCE: 50

Ile Pro Gly Ala Ala Ala Asn Val Thr Ala Thr Leu Ser Ser Val Ala
1               5                   10                  15

Asn Lys Ile

<210> SEQ ID NO 51
<211> LENGTH: 19
<212> TYPE: PRT
<213> ORGANISM: Chlamydophila caviae GPIC
<220> FEATURE:
<223> OTHER INFORMATION: TarP VBS3

<400> SEQUENCE: 51

Leu His Gly Ala Ala Lys Gly Val Ala Asp Ser Leu Ser Asn Leu Leu
1               5                   10                  15

Gln Ala Ala

<210> SEQ ID NO 52
<211> LENGTH: 19
<212> TYPE: PRT
<213> ORGANISM: Chlamydophila abortus
<220> FEATURE:
<223> OTHER INFORMATION: TarP VBS1

<400> SEQUENCE: 52

Leu Ala Asp Ala Ala Arg Asn Val Thr Thr Gln Leu Ser Lys Thr Leu
1               5                   10                  15

Ser Lys Ala

<210> SEQ ID NO 53
<211> LENGTH: 19
<212> TYPE: PRT
<213> ORGANISM: Chlamydophila abortus
<220> FEATURE:
<223> OTHER INFORMATION: TarP VBS2

<400> SEQUENCE: 53

Ile Pro Glu Ala Ala Gly Asn Val Ile Gln Ala Leu Ser Asn Val Ala
1               5                   10                  15

Lys Lys Ile

<210> SEQ ID NO 54
<211> LENGTH: 19
<212> TYPE: PRT
<213> ORGANISM: Chlamydophila abortus
<220> FEATURE:
```

-continued

<223> OTHER INFORMATION: TarP VBS3

<400> SEQUENCE: 54

Leu His Gly Ala Ala Arg Asp Val Ala Ser Ser Leu Ser Asn Leu Leu
1               5                   10                  15

Glu Ala Ala

<210> SEQ ID NO 55
<211> LENGTH: 19
<212> TYPE: PRT
<213> ORGANISM: Chlamydophila felis
<220> FEATURE:
<223> OTHER INFORMATION: TarP VBS1

<400> SEQUENCE: 55

Leu Phe Asp Ala Ala Lys Gln Thr Thr Ala Gln Leu Ser Lys Met Ile
1               5                   10                  15

Tyr Arg Ala

<210> SEQ ID NO 56
<211> LENGTH: 19
<212> TYPE: PRT
<213> ORGANISM: Chlamydophila felis
<220> FEATURE:
<223> OTHER INFORMATION: TarP VBS2

<400> SEQUENCE: 56

Ile Pro Gln Ala Ala Ala Asn Val Thr Gln Thr Leu Ser Asn Val Thr
1               5                   10                  15

Gln Lys Leu

<210> SEQ ID NO 57
<211> LENGTH: 19
<212> TYPE: PRT
<213> ORGANISM: Chlamydophila felis
<220> FEATURE:
<223> OTHER INFORMATION: TarP VBS3

<400> SEQUENCE: 57

Leu Tyr Ala Ala Ala Gly Asn Val Ala Asp Ser Leu Ser Asn Leu Leu
1               5                   10                  15

Gln Ala Ala

<210> SEQ ID NO 58
<211> LENGTH: 19
<212> TYPE: PRT
<213> ORGANISM: Chlamydia muridarum
<220> FEATURE:
<223> OTHER INFORMATION: TarP VBS1

<400> SEQUENCE: 58

Leu Phe Ala Ala Ala Arg Ala Thr Thr Gln Ser Leu Ser Ser Leu Ile
1               5                   10                  15

Gly Thr Val

<210> SEQ ID NO 59
<211> LENGTH: 19
<212> TYPE: PRT
<213> ORGANISM: Chlamydia muridarum
<220> FEATURE:
<223> OTHER INFORMATION: TarP VBS2

<400> SEQUENCE: 59

```
Leu Tyr Asp Ala Ala Lys Asn Val Thr Gln Ala Leu Thr Ser Val Thr
1               5                   10                  15

Asn Lys Val

<210> SEQ ID NO 60
<211> LENGTH: 26
<212> TYPE: PRT
<213> ORGANISM: Homo sapiens
<220> FEATURE:
<223> OTHER INFORMATION: Talin-1 Helix 46 (H46)

<400> SEQUENCE: 60

Tyr Thr Lys Lys Glu Leu Ile Glu Cys Ala Arg Arg Val Ser Glu Lys
1               5                   10                  15

Val Ser His Val Leu Ala Ala Leu Gln Ala
            20                  25

<210> SEQ ID NO 61
<211> LENGTH: 9
<212> TYPE: PRT
<213> ORGANISM: Shigella flexneri 5a
<220> FEATURE:
<223> OTHER INFORMATION: N-ter domain

<400> SEQUENCE: 61

Gly Asp Pro Tyr Leu Thr Arg Glu Thr
1               5

<210> SEQ ID NO 62
<211> LENGTH: 55
<212> TYPE: PRT
<213> ORGANISM: Shigella flexneri 5a
<220> FEATURE:
<223> OTHER INFORMATION: Interdomain VBS3-VBS2

<400> SEQUENCE: 62

Gly Thr Lys Ser Gly Thr Gln Glu Arg Glu Leu Gln Glu Lys Ser Lys
1               5                   10                  15

Asp Ile Thr Lys Ser Thr Thr Glu His Arg Ile Asn Asn Lys Leu Lys
            20                  25                  30

Ile Thr Asp Ala Asn Thr Ile Asn Tyr Val Thr Glu Thr Asn Ala Asp
        35                  40                  45

Thr Ile Asp Lys Asn His Ala
        50              55

<210> SEQ ID NO 63
<211> LENGTH: 55
<212> TYPE: PRT
<213> ORGANISM: Shigella sonnei 53G
<220> FEATURE:
<223> OTHER INFORMATION: Interdomain VBS3-VBS2

<400> SEQUENCE: 63

Gly Thr Lys Ser Gly Thr Gln Glu Arg Glu Leu Gln Glu Lys Ser Lys
1               5                   10                  15

Asp Ile Thr Lys Ser Thr Thr Glu His Arg Ile Asn Asn Lys Leu Lys
            20                  25                  30

Val Thr Asp Ala Asn Thr Ile Asn Tyr Val Thr Glu Thr Asn Ala Asp
        35                  40                  45

Thr Ile Asp Lys Asn His Ala
        50              55
```

-continued

```
<210> SEQ ID NO 64
<211> LENGTH: 55
<212> TYPE: PRT
<213> ORGANISM: Shigella dysenteriae
<220> FEATURE:
<223> OTHER INFORMATION: Interdomain VBS3-VBS2

<400> SEQUENCE: 64

Gly Thr Lys Ser Gly Thr Gln Glu Arg Glu Leu Gln Glu Lys Ser Lys
1               5                   10                  15

Asp Ile Thr Lys Ser Thr Thr Glu His Arg Ile Asn Asn Lys Leu Lys
            20                  25                  30

Ile Thr Asp Ala Asn Thr Arg Asn Tyr Val Thr Glu Thr Asn Ala Asp
        35                  40                  45

Thr Ile Asp Lys Asn His Ala
    50                  55

<210> SEQ ID NO 65
<211> LENGTH: 27
<212> TYPE: PRT
<213> ORGANISM: Shigella flexneri 5a
<220> FEATURE:
<223> OTHER INFORMATION: Interdomain VBS2-VBS1

<400> SEQUENCE: 65

Asp Asp Thr Ser Ala Glu Leu Leu Thr Glu Asp Ile Ser Asn Leu Lys
1               5                   10                  15

Asn Asn Asn Asp Ile Thr Ala Glu Asn Asn Asn
            20                  25

<210> SEQ ID NO 66
<211> LENGTH: 22
<212> TYPE: PRT
<213> ORGANISM: Shigella flexneri
<220> FEATURE:
<223> OTHER INFORMATION: IpaA VBS1

<400> SEQUENCE: 66

Ile Tyr Lys Ala Ala Lys Asp Val Thr Thr Ser Leu Ser Lys Val Leu
1               5                   10                  15

Lys Asn Ile Asn Lys Asp
            20

<210> SEQ ID NO 67
<211> LENGTH: 21
<212> TYPE: PRT
<213> ORGANISM: Shigella flexneri
<220> FEATURE:
<223> OTHER INFORMATION: IpaA VBS2

<400> SEQUENCE: 67

Ile Tyr Glu Lys Ala Lys Glu Val Ser Ser Ala Leu Ser Lys Val Leu
1               5                   10                  15

Ser Lys Ile Asp Asp
            20

<210> SEQ ID NO 68
<211> LENGTH: 25
<212> TYPE: PRT
<213> ORGANISM: Shigella flexneri
<220> FEATURE:
<223> OTHER INFORMATION: IpaA VBS3

<400> SEQUENCE: 68
```

```
Thr Arg Glu Thr Ile Phe Glu Ala Ser Lys Lys Val Thr Asn Ser Leu
1               5                   10                  15
Ser Asn Leu Ile Ser Leu Ile Gly Thr
            20                  25
```

<210> SEQ ID NO 69
<211> LENGTH: 66
<212> TYPE: DNA
<213> ORGANISM: Shigella flexneri
<220> FEATURE:
<223> OTHER INFORMATION: IpaA VBS1

<400> SEQUENCE: 69
atatataaag cagcaaaaga tgtaaccact tccctatcaa agtattaaa gaatatcaat   60 aaggat                                                            66

<210> SEQ ID NO 70
<211> LENGTH: 63
<212> TYPE: DNA
<213> ORGANISM: Shigella flexneri
<220> FEATURE:
<223> OTHER INFORMATION: IpaA VBS2

<400> SEQUENCE: 70
atctatgaaa aggcaaaaga agtatctagc gccctcagca aggtattgtc aaaaattgac   60
gat                                                                63

<210> SEQ ID NO 71
<211> LENGTH: 75
<212> TYPE: DNA
<213> ORGANISM: Shigella flexneri
<220> FEATURE:
<223> OTHER INFORMATION: IpaA VBS3

<400> SEQUENCE: 71
acacgggaaa cgatatttga agcttcaaaa aaagtaacaa actccctaag taatcttata   60
tctctcattg gaact                                                   75

<210> SEQ ID NO 72
<211> LENGTH: 5
<212> TYPE: PRT
<213> ORGANISM: Shigella flexneri
<220> FEATURE:
<223> OTHER INFORMATION: N-ter domain

<400> SEQUENCE: 72

```
Gly Asp Thr Tyr Leu
1               5
```

<210> SEQ ID NO 73
<211> LENGTH: 53
<212> TYPE: PRT
<213> ORGANISM: Shigella flexneri
<220> FEATURE:
<223> OTHER INFORMATION: Interdomain VBS3-VBS2

<400> SEQUENCE: 73

```
Lys Ser Gly Thr Gln Glu Arg Glu Leu Gln Lys Ser Lys Asp Ile
1               5                   10                  15
Thr Lys Ser Thr Thr Glu His Arg Ile Asn Asn Lys Leu Lys Val Thr
                20                  25                  30
Asp Ala Asn Ile Arg Asn Tyr Val Thr Glu Thr Asn Ala Asp Thr Ile
            35                  40                  45
```

Asp Lys Asn His Ala
    50

<210> SEQ ID NO 74
<211> LENGTH: 25
<212> TYPE: PRT
<213> ORGANISM: Shigella flexneri
<220> FEATURE:
<223> OTHER INFORMATION: Interdomain VBS2-VBS1

<400> SEQUENCE: 74

Thr Ser Ala Glu Leu Leu Thr Asp Asp Ile Ser Asp Leu Lys Asn Asn
1               5                   10                  15

Asn Asp Ile Thr Ala Glu Asn Asn Asn
            20                  25

<210> SEQ ID NO 75
<211> LENGTH: 5
<212> TYPE: PRT
<213> ORGANISM: Shigella flexneri 5a
<220> FEATURE:
<223> OTHER INFORMATION: N-ter domain

<400> SEQUENCE: 75

Gly Asp Pro Tyr Leu
1               5

<210> SEQ ID NO 76
<211> LENGTH: 53
<212> TYPE: PRT
<213> ORGANISM: Shigella flexneri 5a
<220> FEATURE:
<223> OTHER INFORMATION: Interdomain VBS3-VBS2

<400> SEQUENCE: 76

Lys Ser Gly Thr Gln Glu Arg Glu Leu Gln Glu Lys Ser Lys Asp Ile
1               5                   10                  15

Thr Lys Ser Thr Thr Glu His Arg Ile Asn Asn Lys Leu Lys Ile Thr
            20                  25                  30

Asp Ala Asn Thr Ile Asn Tyr Val Thr Glu Thr Asn Ala Asp Thr Ile
        35                  40                  45

Asp Lys Asn His Ala
    50

<210> SEQ ID NO 77
<211> LENGTH: 53
<212> TYPE: PRT
<213> ORGANISM: Shigella sonnei 53G
<220> FEATURE:
<223> OTHER INFORMATION: Interdomain VBS3-VBS2

<400> SEQUENCE: 77

Lys Ser Gly Thr Gln Glu Arg Glu Leu Gln Glu Lys Ser Lys Asp Ile
1               5                   10                  15

Thr Lys Ser Thr Thr Glu His Arg Ile Asn Asn Lys Leu Lys Val Thr
            20                  25                  30

Asp Ala Asn Thr Ile Asn Tyr Val Thr Glu Thr Asn Ala Asp Thr Ile
        35                  40                  45

Asp Lys Asn His Ala
    50

<210> SEQ ID NO 78

-continued

```
<211> LENGTH: 53
<212> TYPE: PRT
<213> ORGANISM: Shigella dysenteriae
<220> FEATURE:
<223> OTHER INFORMATION: Interdomain VBS3-VBS2

<400> SEQUENCE: 78

Lys Ser Gly Thr Gln Glu Arg Glu Leu Gln Glu Lys Ser Lys Asp Ile
1               5                   10                  15

Thr Lys Ser Thr Thr Glu His Arg Ile Asn Asn Lys Leu Lys Ile Thr
            20                  25                  30

Asp Ala Asn Thr Arg Asn Tyr Val Thr Glu Thr Asn Ala Asp Thr Ile
        35                  40                  45

Asp Lys Asn His Ala
    50

<210> SEQ ID NO 79
<211> LENGTH: 25
<212> TYPE: PRT
<213> ORGANISM: Shigella flexneri 5a
<220> FEATURE:
<223> OTHER INFORMATION: Interdomain VBS2-VBS1

<400> SEQUENCE: 79

Thr Ser Ala Glu Leu Leu Thr Glu Asp Ile Ser Asn Leu Lys Asn Asn
1               5                   10                  15

Asn Asp Ile Thr Ala Glu Asn Asn Asn
            20                  25
```

POLYPEPTIDES COMPRISING VINCULIN BINDING SITES FOR THE TREATMENT OF PROLIFERATION AND/OR ADHESION RELATED DISEASES

FIELD OF INVENTION

The present invention relates to the treatment of proliferation and/or adhesion related diseases, such as cancer and metastasis. In particular, the present invention relates to polypeptides that comprise vinculin binding sites (VBSs), and to the use thereof for treating proliferation and/or adhesion related diseases.

BACKGROUND OF INVENTION

Cancer and tumor cells are characterized by dysregulation of the cellular cycle leading to abnormal proliferation. These cells also exhibit dysregulation in adherence properties which are characteristics associated with increased invasive and migratory properties determining the metastatic potential of cells.

Generally, anticancer drugs include protein kinases inhibitors, microtubules inhibitors, or anti-metabolite agents targeting cells that divide rapidly. Therefore, besides cancer cells, blood cells are also targeted. When blood cells are affected, patients are more likely to get infections, or bleed easily, and may feel unusually weak and very tired. Rapidly dividing cells in hair roots and cells that line the digestive tract may also be affected. Therefore, there is a need to develop novel strategies to fight cancer and to avoid this cytotoxic effect.

Another characteristic of cancer cells is a decrease in adhesion properties. The Applicant's strategy thus consists in targeting the anchoring to the cellular matrix. The purpose of this alternative treatment is thus inhibiting the proliferation, modulating the adhesion properties and the invasiveness of the cancer cells. In particular, the Applicant aimed at developing novel agents for inducing strong adherence of cells independently of the mechanosensing phenomenon, thereby inducing cellular adherence de novo (for example of non-adherent cells, especially of metastasis) or thereby reinforcing already existent cellular adherence.

*Shigella* is a bacterium injecting proteins into host cells that reorganize the cytoskeleton, to trigger its internalization by epithelial cells. Among these proteins, IpaA is involved in bacterial internalization by promoting anchorage of the bacteria on host cells. Analysis demonstrated that the C-terminus of IpaA was involved in these processes due the presence of vinculin binding sites (VBSs) (Orchard R. C. & Alto N. M., 2012. *Cell Microbiol.* 14:10-8; Izard T. et al., 2006. *J. Cell Biol.* 175:465-75; Tran Van Nhieu G. & Izard T., 2007. *EMBO J.* 26:4588-96; Park H. et al., 2011. *J. Biol. Chem.* 286:23214-21). The binding of IpaA to vinculin induces changes in vinculin's conformation from an inactive to an active state.

The Applicant surprisingly demonstrates that a peptide derived from IpaA, and in particular a peptide comprising the 3 VBSs of IpaA, induces a novel conformational state of vinculin, defined as a "supra-activation state", thereby inducing cell anchoring to a support. This supra-activation of vinculin is only observed in presence of VBS3, but not when only VBS1 and VBS2 are comprised in the peptide. This result was particularly unexpected, because VBS3 previously described in the art as functionally redundant with the other two IpaA-VBSs (Park H. et al. 2011. *J. Biol. Chem.* 286:23214-21).

Moreover, the results of the Applicant presented in the present application demonstrate an unexpected synergistic effect between the three VBSs of IpaA. Strikingly, cell anchorage induced by the peptide of the invention is independent of the mechanosensing phenomenon.

Therefore, a peptide comprising the 3 VBSs of IpaA may be used for treating cancer, and in particular for treating or preventing metastasis.

SUMMARY

One object of the present invention is a polypeptide comprising the three following vinculin binding sites (VBS):
  VBS1: IYKAAKDVTTSLSKVLKNI (SEQ ID NO: 2) or a fragment or variant thereof;
  VBS2: IYEKAKEVSSALSKVLSKI (SEQ ID NO: 3) or a fragment or variant thereof;
  VBS3: IFEASKKVTNSLSNLISLI (SEQ ID NO: 4) or a fragment or variant thereof;
  or any sequence having at least 60% identity with SEQ ID NO: 2; 3 and 4;
  wherein said polypeptide is not SEQ ID NO: 1.

In one embodiment, said polypeptide is SEQ ID NO: 5 or a variant thereof.

Another object of the present invention is a nucleic acid comprising the three following domains:
  VBS1 (SEQ ID NO: 8);
  VBS2 (SEQ ID NO: 9);
  VBS3 (SEQ ID NO: 10);
  or any nucleic acid sequence having at least 60% identity with SEQ ID NO: 8; 9 and 10;
  wherein said nucleic acid is not SEQ ID NO: 7.

In one embodiment, said nucleic acid is SEQ ID NO: 6.

Another object of the present invention is a vector encoding the polypeptide as described above, or comprising the nucleic acid sequence as described above.

Another object of the present invention is a composition comprising the polypeptide as described above or the nucleic acid sequence as described above or the vector as described above.

Another object of the present invention is a pharmaceutical composition comprising the polypeptide as described above or the nucleic acid sequence as described above or the vector as described above and at least one pharmaceutically acceptable excipient.

Another object of the present invention is a medicament comprising the polypeptide as described above or the nucleic acid sequence as described above or the vector as described above.

In one embodiment, the composition as described above or the pharmaceutical composition as described above or the medicament as described above are for use in the treatment of a proliferation and/or adhesion related disease.

In another embodiment, the proliferation and/or adhesion related disease is a cancer.

In another embodiment, the proliferation and/or adhesion related disease is a tumor.

In another embodiment, the proliferation and/or adhesion related disease is metastasis.

In another embodiment, the composition, the pharmaceutical composition or the medicament as described above, is to be administered in combination with another anti-cancer agent.

Definitions

In the present invention, the following terms have the following meanings:

"Binding Site" refers to a domain responsible for selectively binding to a polypeptide. Binding domains or binding regions comprise at least one binding site. Exemplary binding sites comprise VBS1 (SEQ ID NO: 2), VBS2 (SEQ ID NO: 3) and VBS3 (SEQ ID NO: 4).

"Identity" when used in a relationship between the sequences of two or more nucleic acid sequences or amino acid sequences, refers to the degree of sequence relatedness between the sequences, as determined by the number of matches between strings of two or more base pairs of nucleic acid or amino acid residues. "Identity" measures the percent of identical matches between the smaller of two or more sequences with gap alignments (if any) addressed by a particular mathematical model or computer program (i.e., "algorithms"). Identity of related nucleic acid sequences or amino acid sequences can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NTH Bethesda, Md. 20894; Altschul et al., supra). The well-known Smith Waterman algorithm may also be used to determine identity.

"Nucleic acid sequence" encompasses nucleic acids having the sequences set forth below as well as variants thereof including for example fragments, deletions, insertions and substitutions that comprise the VBS domains as described in the present invention.

"Polypeptide" is used in its conventional meaning, i.e., as a sequence of amino acids. Unless otherwise specified, a polypeptide is not limited to a specific length of the product. Peptides, oligopeptides, and proteins are included within the definition of polypeptide, and such terms may be used interchangeably herein unless specifically indicated otherwise. This term may also include post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising VBSs. An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver staining. Isolated polypeptide includes the polypeptide in situ within recombinant cells since at least one component of the polypeptide's natural environment will not be present. Ordinarily, however, isolated polypeptide will be prepared by at least one purification step.

"Pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

"Therapeutically effective amount" means level or amount of agent that is aimed at, without causing significant negative or adverse side effects to the target, (1) delaying or preventing the onset of a disease, disorder, or condition related to proliferation and/or adhesion; (2) slowing down or stopping the progression, aggravation, or deterioration of one or more symptoms of the disease, disorder, or condition related to proliferation and/or adhesion; (3) bringing about ameliorations of the symptoms of the disease, disorder, or condition related to proliferation and/or adhesion; (4) reducing the severity or incidence of the disease, disorder, or condition related to proliferation and/or adhesion; or (5) curing the disease, disorder, or condition related to proliferation and/or adhesion. A therapeutically effective amount may be administered prior to the onset of the disease, disorder, or condition related to proliferation and/or adhesion, for a prophylactic or preventive action. Alternatively or additionally, the therapeutically effective amount may be administered after initiation of the disease, disorder, or condition related to proliferation and/or adhesion, for a therapeutic action.

"Treating" or "treatment" refer to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for the targeted pathologic condition or disorder if, after receiving a therapeutic amount of the polypeptide according to the present invention, the subject shows observable and/or measurable reduction in or absence of one or more of the following: reduction in the number of pathogenic cells; reduction in the percent of total cells that are pathogenic; and/or relief to some extent, of one or more of the symptoms associated with the specific disease or condition; reduced morbidity and mortality, and improvement in quality of life issues. The above parameters for assessing successful treatment and improvement in the disease are readily measurable by routine procedures familiar to a physician.

"Subject" refers to an animal, including a human. In the sense of the present invention, a subject may be a patient, i.e. a person receiving medical attention, undergoing or having underwent a medical treatment, or monitored for the development of a disease. In one embodiment, the subject is a male. In another embodiment, the subject is a female.

"About" preceding a figure means plus or less 10% of the value of said figure.

DETAILED DESCRIPTION

One object of the invention is a polypeptide comprising at least one of the following VBSs:
VBS1: IYKAAKDVTTSLSKVLKNI (SEQ ID NO: 2) or IYKAAKDVTTSLSKVLKNINKD (SEQ ID NO: 66) or a fragment or variant thereof;
VBS2: IYEKAKEVSSALSKVLSKI (SEQ ID NO: 3) or TYEKAKEVSSALSKVLSKIDD (SEQ ID NO: 67) or a fragment or variant thereof;
VBS3: IFEASKKVTNSLSNLISLI (SEQ ID NO: 4) or TRETIFEASKKKVTNSLSNLISLIGT (SEQ ID NO: 68) or a fragment or variant thereof;
or any fragment or variant thereof having at least 60; 65; 70; 75; 80; 85; 90; 95; 96; 97; 98; 99% identity with SEQ ID NO: 2; 3; 4; 66; 67 and 68.

In one embodiment, the polypeptide comprises at least one of the following VBSs:
VBS1: TYKAAKDVTTSLSKVLKNI (SEQ ID NO: 2) or a fragment or variant thereof;
VBS2: IYEKAKEVSSALSKVLSKI (SEQ ID NO: 3) or a fragment or variant thereof;
VBS3: IFEASKKVTNSLSNLISLI (SEQ ID NO: 4) or a fragment or variant thereof;
or any fragment or variant thereof having at least 60; 65; 70; 75; 80; 85; 90; 95; 96; 97; 98; 99% identity with SEQ ID NO: 2; 3 or 4.

In one embodiment, the polypeptide comprises at least one of the following VBSs:
VBS1: IYKAAKDVTTSLSKVLKNINKD (SEQ ID NO: 66) or a fragment or variant thereof;
VBS2: IYEKAKEVSSALSKVLSKIDD (SEQ ID NO: 67) or a fragment or variant thereof;
VBS3: TRETIFEASKKKVTNSLSNLISLIGT (SEQ ID NO: 68) or a fragment or variant thereof;
or any fragment or variant thereof having at least 60; 65; 70; 75; 80; 85; 90; 95; 96; 97; 98; 99% identity with SEQ ID NO: 66; 67 or 68.

In one embodiment, the polypeptide of the invention comprises two VBS (or a fragment or variant thereof) selected from SEQ ID NO: 2-4. In one embodiment, the polypeptide of the invention comprises two VBS (or a fragment or variant thereof) selected from SEQ ID NO: 66-68. In another embodiment, the polypeptide of the invention comprises the three VBSs (or a fragment or variant thereof) as described hereinabove.

In one embodiment, the polypeptide of the invention comprises, from Nterm to Cterm:
optionally an amino acid sequence comprising from 1 to 20 amino acids, preferably from 1 to 10 amino acids;
a sequence consisting of SEQ ID NO: 4 or SEQ ID NO: 68 or a variant thereof;
optionally an amino acid sequence comprising from 1 to 100 amino acids, preferably from 1 to 60 amino acids;
a sequence consisting of SEQ ID NO: 3 or SEQ ID NO: 67 or a variant thereof;
optionally an amino acid sequence comprising from 1 to 50 amino acids, preferably from 1 to 30 amino acids;
a sequence consisting of SEQ ID NO: 2 or SEQ ID NO: 66 or a variant thereof, and
optionally an amino acid sequence comprising from 1 to 20 amino acids, preferably from 1 to 10 amino acids, more preferably from 1 to 5 amino acids.

In one embodiment, the polypeptide of the invention comprises, from Nterm to Cterm:
0, 1, 2, 3, 4, 5, 6, 7, 8 or 9 amino acids;
a sequence consisting of SEQ ID NO: 4 or SEQ ID NO: 68 or a variant thereof;
0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids;
a sequence consisting of SEQ ID NO: 3 or SEQ ID NO: 67 or a variant thereof;
0,1,2,3,4,5,6,7,8,9,10, 11,12,13,14,15,16,17, 18,19,20,21, 22,23,24,25, 26 or 27 amino acids;
a sequence consisting of SEQ ID NO: 2 or SEQ ID NO: 66 or a variant thereof, and
0, 1, 2, 3, 4, 5, 6, 7, 8 or 9 amino acids.

In one embodiment, the polypeptide of the invention comprises, from Nterm to Cterm:
optionally, an amino acid sequence comprising or consisting of GDTYLTRET (SEQ ID NO: 40) or a variant thereof;
a sequence consisting of SEQ ID NO: 4 or a variant thereof;
optionally, an amino acid sequence comprising or consisting of GTKSGTQERELQEKSKDITKSTTEH-RINNKLKVTDANIRNYVTETNADTIDK NHA (SEQ ID NO: 41) or a variant thereof;
a sequence consisting of SEQ ID NO: 3 or a variant thereof;
optionally, an amino acid sequence comprising or consisting of DDTSAELLTDDISDLKNNNDITAENNN (SEQ ID NO: 42) or a variant thereof;
a sequence consisting of SEQ ID NO: 2 or a variant thereof; and
optionally, an amino acid sequence comprising or consisting of NKD or a variant thereof.

In one embodiment, the polypeptide of the invention comprises, from Nterm to Cterm:
optionally, an amino acid sequence comprising or consisting of GDTYL (SEQ ID NO: 72) or a variant thereof;
a sequence consisting of SEQ ID NO: 68 or a variant thereof;
optionally, an amino acid sequence comprising or consisting of KSGTQERELQEKSKDITKSTTEH-RINNKLKVTDANIRNYVTETNADTIDKNH A (SEQ ID NO: 73) or a variant thereof;
a sequence consisting of SEQ ID NO: 67 or a variant thereof;
optionally, an amino acid sequence comprising or consisting of TSAELLTDDISDLKNNNDITAENNN (SEQ ID NO: 74) or a variant thereof, and
a sequence consisting of SEQ ID NO: 66 or a variant thereof.

In one embodiment, the polypeptide of the invention comprises, from Nterm to Cterm:
- an amino acid sequence comprising or consisting of SEQ ID NO: 40 or a fragment or a variant thereof;
- a sequence consisting of SEQ ID NO: 4 or a variant thereof;
- an amino acid sequence comprising or consisting of SEQ ID NO: 41 or a fragment or a variant thereof;
- a sequence consisting of SEQ ID NO: 3 or a variant thereof;
- an amino acid sequence comprising or consisting of SEQ ID NO: 42 or a fragment or a variant thereof;
- a sequence consisting of SEQ ID NO: 2 or a variant thereof; and
- an amino acid sequence comprising or consisting of NKD or a variant thereof.

In one embodiment, the polypeptide of the invention comprises, from Nterm to Cterm:
- an amino acid sequence comprising or consisting of SEQ ID NO: 72 or a fragment or a variant thereof;
- a sequence consisting of SEQ ID NO: 68 or a variant thereof;
- an amino acid sequence comprising or consisting of SEQ ID NO: 73 or a fragment or a variant thereof;
- a sequence consisting of SEQ ID NO: 67 or a variant thereof;
- an amino acid sequence comprising or consisting of SEQ ID NO: 74 or a fragment or a variant thereof; and
- a sequence consisting of SEQ ID NO: 66 or a variant thereof.

In one embodiment, the polypeptide of the invention comprises, from Cterm to Nterm:
- optionally an amino acid sequence comprising from 1 to 20 amino acids, preferably from 1 to 10 amino acids;
- a sequence consisting of SEQ ID NO: 4 or SEQ ID NO: 68 or a variant thereof;
- optionally an amino acid sequence comprising from 1 to 100 amino acids, preferably from 1 to 60 amino acids;
- a sequence consisting of SEQ ID NO: 3 or SEQ ID NO: 67 or a variant thereof;
- optionally an amino acid sequence comprising from 1 to 50 amino acids, preferably from 1 to 30 amino acids;
- a sequence consisting of SEQ ID NO: 2 or SEQ ID NO: 66 or a variant thereof; and
- optionally an amino acid sequence comprising from 1 to 20 amino acids, preferably from 1 to 10 amino acids, more preferably from 1 to 5 amino acids.

In one embodiment, the polypeptide of the invention comprises, from Cterm to Nterm:
- 0, 1, 2, 3, 4, 5, 6, 7, 8 or 9 amino acids;
- a sequence consisting of SEQ ID NO: 4 or SEQ ID NO: 68 or a variant thereof;
- 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids;
- a sequence consisting of SEQ ID NO: 3 or SEQ ID NO: 67 or a variant thereof;
- 0, 1, 2, 3, 4, 5, 6, 7, 8, 9, 10, 11, 12, 13, 14, 15, 16, 17, 18, 19, 20, 21, 22, 23, 24, 25, 26 or 27 amino acids;
- a sequence consisting of SEQ ID NO: 2 or SEQ ID NO: 66 or a variant thereof, and
- 0, 1, 2, 3, 4, 5, 6, 7, 8 or 9 amino acids.

In one embodiment, the polypeptide of the invention comprises, from Cterm to Nterm:
- optionally, an amino acid sequence comprising or consisting of SEQ ID NO: 40 or a variant thereof;
- a sequence consisting of SEQ ID NO: 4 or a variant thereof;
- optionally, an amino acid sequence comprising or consisting of SEQ ID NO: 41 or a variant thereof;
- a sequence consisting of SEQ ID NO: 3 or a variant thereof;
- optionally, an amino acid sequence comprising or consisting of SEQ ID NO: 42 or a variant thereof;
- a sequence consisting of SEQ ID NO: 2 or a variant thereof; and
- optionally, an amino acid sequence comprising or consisting of NKD or a variant thereof.

In one embodiment, the polypeptide of the invention comprises, from Cterm to Nterm:
- optionally, an amino acid sequence comprising or consisting of SEQ ID NO: 72 or a variant thereof;
- a sequence consisting of SEQ ID NO: 68 or a variant thereof;
- optionally, an amino acid sequence comprising or consisting of SEQ ID NO: 73 or a variant thereof;
- a sequence consisting of SEQ ID NO: 67 or a variant thereof;
- optionally, an amino acid sequence comprising or consisting of SEQ ID NO: 74 or a variant thereof; and
- a sequence consisting of SEQ ID NO: 66 or a variant thereof.

In one embodiment, the polypeptide of the invention comprises, from Cterm to Nterm:
- an amino acid sequence comprising or consisting of SEQ ID NO: 40 or a fragment or a variant thereof;
- a sequence consisting of SEQ ID NO: 4 or a variant thereof;
- an amino acid sequence comprising or consisting of SEQ ID NO: 41 or a fragment or a variant thereof;
- a sequence consisting of SEQ ID NO: 3 or a variant thereof;
- an amino acid sequence comprising or consisting of SEQ ID NO: 42 or a fragment or a variant thereof;
- a sequence consisting of SEQ ID NO: 2 or a variant thereof; and
- an amino acid sequence comprising or consisting of NKD or a variant thereof.

In one embodiment, the polypeptide of the invention comprises, from Cterm to Nterm:
- an amino acid sequence comprising or consisting of SEQ ID NO: 72 or a fragment or a variant thereof;
- a sequence consisting of SEQ ID NO: 68 or a variant thereof;
- an amino acid sequence comprising or consisting of SEQ ID NO: 73 or a fragment or a variant thereof;
- a sequence consisting of SEQ ID NO: 67 or a variant thereof;
- an amino acid sequence comprising or consisting of SEQ ID NO: 74 or a fragment or a variant thereof; and
- a sequence consisting of SEQ ID NO: 66 or a variant thereof.

In one embodiment, a variant of SEQ ID NO: 2, 3, 4, 40, 41, 42, 66, 67 or 68 comprises conservative amino acid substitutions as compared to the sequence of SEQ ID NO: 2, 3, 4, 40, 41, 42, 66, 67 or 68, respectively.

In another embodiment, a variant of SEQ ID NO: 2, 3, 4, 40, 41, 42, 66, 67 or 68 is a polypeptide having a sequence identity of at least 70%, preferably of at least 75, 80, 85, 90, 95, 96, 97, 98, 99% or more with SEQ ID NO: 2, 3, 4, 40, 41, 42, 66, 67 or 68, respectively.

In another embodiment, a variant of SEQ ID NO: 2, 3, 4, 40, 41, 42, 66, 67 or 68 is a polypeptide wherein 1, 2, 3, 4, or 5 amino acids from the sequence of SEQ ID NO: 2, 3, 4, 40, 41, 42, 66, 67 or 68 (respectively) is/are absent, or substituted by any amino acid, or wherein 1, 2, 3, 4 or 5 amino acids (either contiguous or not) is/are added.

In one embodiment, a variant of SEQ ID NO: 2 or SEQ ID NO: 66 comprises amino acid residues K6 or K14 of SEQ ID NO: 2 or 66. In another embodiment, a variant of SEQ ID NO: 2 or SEQ ID NO: 66 comprises amino acid residues K6 and K14 of SEQ ID NO: 2 or 66.

In one embodiment, a variant of SEQ ID NO: 2 or SEQ ID NO: 66 is SEQ ID NO: 47 (LFQAATQTTQALSSLIDTVG). SEQ ID NO: 47 corresponds to VBS1 of the translocated actin recruiting phosphoprotein from Chlamydia trachomatis serovar L2. In one embodiment, a variant of SEQ ID NO: 2 or SEQ ID NO: 66 is SEQ ID NO: 49 (LLEAARNTTTMLSKTLSKV). SEQ ID NO: 49 corresponds to VBS1 of the translocated actin recruiting phosphoprotein from Chlamydophila caviae, strain GPIC.

In one embodiment, a variant of SEQ ID NO: 2 or SEQ ID NO: 66 is SEQ ID NO: 52 (LADAARNVTTQLSKTLSKA). SEQ ID NO: 52 corresponds to VBS1 of the translocated actin recruiting phosphoprotein from Chlamydophila abortus.

In one embodiment, a variant of SEQ ID NO: 2 or SEQ ID NO: 66 is SEQ ID NO: 55 (LFDAAKQTTAQLSKMIYRA). SEQ ID NO: 55 corresponds to VBS1 of the translocated actin recruiting phosphoprotein from Chlamydophila felis.

In one embodiment, a variant of SEQ ID NO: 2 or SEQ ID NO: 66 is SEQ ID NO: 58 (LFAAARATTQSLSSLIGTV). SEQ ID NO: 58 corresponds to VBS1 of the translocated actin recruiting phosphoprotein from Chlamydia muridarum.

In one embodiment, a variant of SEQ ID NO: 3 or SEQ ID NO: 67 comprises amino acid residues K6 or K14 of SEQ ID NO: 3 or 67. In another embodiment, a variant of SEQ ID NO: 3 or SEQ ID NO: 67 comprises amino acid residues K6 and K14 of SEQ ID NO: 3 or 67.

In one embodiment, a variant of SEQ ID NO: 3 or SEQ ID NO: 67 is SEQ ID NO: 48 (LFQAAAVTQALGNVAGKVNLAIQG). SEQ ID NO: 48 corresponds to VBS2 of the translocated actin recruiting phosphoprotein from Chlamydia trachomatis serovar L2.

In one embodiment, a variant of SEQ ID NO: 3 or SEQ ID NO: 67 is SEQ ID NO: 50 (IPGAAANVTATLSSVANKI). SEQ ID NO: 50 corresponds to VBS2 of the translocated actin recruiting phosphoprotein from Chlamydophila caviae, strain GPIC.

In one embodiment, a variant of SEQ ID NO: 3 or SEQ ID NO: 67 is SEQ ID NO: 53 (IPEAAGNVIQALSNVAKKI). SEQ ID NO: 53 corresponds to VBS2 of the translocated actin recruiting phosphoprotein from Chlamydophila abortus.

In one embodiment, a variant of SEQ ID NO: 3 or SEQ ID NO: 67 is SEQ ID NO: 56 (IPQAAANVTQTLSNVTQKL). SEQ ID NO: 56 corresponds to VBS2 of the translocated actin recruiting phosphoprotein from Chlamydophila felis.

In one embodiment, a variant of SEQ ID NO: 3 or SEQ ID NO: 67 is SEQ ID NO: 59 (LYDAAKNVTQALTSVTNKV). SEQ ID NO: 59 corresponds to VBS2 of the translocated actin recruiting phosphoprotein from Chlamydia muridarum.

In one embodiment, a variant of SEQ ID NO: 4 comprises amino acid residue K7 of SEQ ID NO: 4. In one embodiment, a variant of SEQ ID NO: 68 comprises amino acid residue K11 of SEQ ID NO: 68.

In one embodiment, a variant of SEQ ID NO: 4 or SEQ ID NO: 68 is SEQ ID NO: 51 (LHGAAKGVADSLSNLLQAA). SEQ ID NO: 51 corresponds to VBS3 of the translocated actin recruiting phosphoprotein from Chlamydophila caviae, strain GPIC.

In one embodiment, a variant of SEQ ID NO: 4 or SEQ ID NO: 68 is SEQ ID NO: 54 (LHGAARDVASSLSNLLEAA). SEQ ID NO: 54 corresponds to VBS3 of the translocated actin recruiting phosphoprotein from Chlamydophila abortus.

In one embodiment, a variant of SEQ ID NO: 4 or SEQ ID NO: 68 is SEQ ID NO: 57 (LYAAAGNVADSLSNLLQAA). SEQ ID NO: 57 corresponds to VBS3 of the translocated actin recruiting phosphoprotein from Chlamydophila felis.

In one embodiment, a variant of SEQ ID NO: 4 or SEQ ID NO: 68 is SEQ ID NO: 60 (YTKKELIECARRVSEKVSHVLAALQA), corresponding to talin H46.

In one embodiment, a variant of SEQ ID NO: 40 or SEQ ID NO: 72 comprises amino acid residue D2 of SEQ ID NO: 40 or 72.

In one embodiment, a variant of SEQ ID NO: 40 is SEQ ID NO: 61 (GDPYLTRET). In one embodiment, a variant of SEQ ID NO: 72 is SEQ ID NO: 75 (GDPYL).

In one embodiment, a variant of SEQ ID NO: 41 comprises amino acid residues K3, K16, K20, K30, K32, E44, D48, D51 or K61 of SEQ ID NO: 41. In one embodiment, a variant of SEQ ID NO: 73 comprises amino acid residues K1, K14, K18, K28, K30, E42, D46, D49 or K59 of SEQ ID NO: 73.

In one embodiment, a variant of SEQ ID NO: 41 comprises amino acid residues K3, K16, K20, K30, K32, E44, D48, D51 and K61 of SEQ ID NO: 41. In one embodiment, a variant of SEQ ID NO: 73 comprises amino acid residues K1, K14, K18, K28, K30, E42, D46, D49 and K59 of SEQ ID NO: 73.

In one embodiment, a variant of SEQ ID NO: 41 comprises at least one (e.g., 1, 2, 3, 4, 5, 6, 7, 8, 9) amino acid residues selected from the group consisting of K3, K16, K20, K30, K32, E44, D48, D51 and K61 of SEQ ID NO: 41. In one embodiment, a variant of SEQ ID NO: 73 comprises at least one (e.g., 1, 2, 3, 4, 5, 6, 7, 8, 9) amino acid residues selected from the group consisting of K1, K14, K18, K28, K30, E42, D46, D49 and K59 of SEQ ID NO: 73.

In one embodiment, a variant of SEQ ID NO: 41 comprises amino acid residue K3 of SEQ ID NO: 41. In one embodiment, a variant of SEQ ID NO: 41 comprises amino acid residue K16 of SEQ ID NO: 41. In one embodiment, a variant of SEQ ID NO: 41 comprises amino acid residue K20 of SEQ ID NO: 41. In one embodiment, a variant of SEQ ID NO: 41 comprises amino acid residue K30 of SEQ ID NO: 41. In one embodiment, a variant of SEQ ID NO: 41 comprises amino acid residue K32 of SEQ ID NO: 41. In one embodiment, a variant of SEQ ID NO: 41 comprises amino acid residue E44 of SEQ ID NO: 41. In one embodiment, a variant of SEQ ID NO: 41 comprises amino acid residue D48 of SEQ ID NO: 41. In one embodiment, a variant of SEQ ID NO: 41 comprises amino acid residue D51 of SEQ ID NO: 41. In one embodiment, a variant of SEQ ID NO: 41 comprises amino acid residue K61 of SEQ ID NO: 41. In one embodiment, a variant of SEQ ID NO: 73 comprises amino acid residue K1 of SEQ ID NO: 73. In one embodiment, a variant of SEQ ID NO: 73 comprises amino acid residue K14 of SEQ ID NO: 73. In one embodiment, a variant of SEQ ID NO: 73 comprises amino acid residue K18 of SEQ ID NO: 73. In one embodiment, a variant of SEQ ID NO: 73 comprises amino acid residue K28 of SEQ ID NO: 73. In one embodiment, a variant of SEQ ID NO: 73 comprises amino acid residue K30 of SEQ ID NO: 73. In one embodiment, a variant of SEQ ID NO: 73 comprises amino acid residue E42 of SEQ ID NO: 73. In one embodiment, a variant of SEQ ID NO: 73 comprises amino acid residue D46 of SEQ ID NO: 73. In one embodiment, a variant of SEQ ID NO: 73 comprises amino acid residue D49 of SEQ ID NO: 73. In one embodiment, a variant of SEQ ID NO: 73 comprises amino acid residue K59 of SEQ ID NO: 73.

In one embodiment, a variant of SEQ ID NO: 41 is SEQ ID NO: 62 (GTKSGTQERELQEKSKDITKSTTEH-RINNKLKITDANTINYVTETNADTIDKNH A). In one embodiment, a variant of SEQ ID NO: 73 is SEQ ID NO: 76 (KSGTQERELQEKSKDITKSTTEHRINNKLKIT-DANTINYVTETNADTIDKNHA). In one embodiment, a variant of SEQ ID NO: 41 is SEQ ID NO: 63 (GTKSGTQERELQEKSKDITKSTTEHRINNKLKVT-DANTINYVTETNADTIDKNH A). In one embodiment, a variant of SEQ ID NO: 73 is SEQ ID NO: 77 (KSGTQERELQEKSKDITKSTTEHRINNKLKVT-DANTINYVTETNADTIDKNHA). In one embodiment, a variant of SEQ ID NO: 41 is SEQ ID NO: 64 (GTKSGTQERELQEKSKDITKSTTEHRINNKLKITD-ANTRNYVTETNADTIDKNH A). In one embodiment, a variant of SEQ ID NO: 73 is SEQ ID NO: 78 (KSGTQERELQEKSKDITKSTTEHRINNKLKITDANT-RNYVTETNADTIDKNHA).

In one embodiment, a variant of SEQ ID NO: 42 comprises amino acid residues E6, D10, D11, or K16 of SEQ ID NO: 42. In one embodiment, a variant of SEQ ID NO: 74 comprises amino acid residues E4, D8, D9, or K14 of SEQ ID NO: 74.

In one embodiment, a variant of SEQ ID NO: 42 comprises amino acid residues E6, D10, D11, and K16 of SEQ ID NO: 42. In one embodiment, a variant of SEQ ID NO: 74 comprises amino acid residues E4, D8, D9, or K14 of SEQ ID NO: 74.

In one embodiment, a variant of SEQ ID NO: 42 comprises at least one (e.g., 1, 2, 3, 4) amino acid residues selected from the group consisting of E6, D10, D1, and K16 of SEQ ID NO: 42. In one embodiment, a variant of SEQ ID NO: 74 comprises at least one (e.g., 1, 2, 3, 4) amino acid residues selected from the group consisting of E4, D8, D9, and K14 of SEQ ID NO: 74.

In one embodiment, a variant of SEQ ID NO: 42 comprises amino acid residue E6 of SEQ ID NO: 42. In one embodiment, a variant of SEQ ID NO: 42 comprises amino acid residue D10 of SEQ ID NO: 42. In one embodiment, a variant of SEQ ID NO: 42 comprises amino acid residue D11 of SEQ ID NO: 42. In one embodiment, a variant of SEQ ID NO: 42 comprises amino acid residue K16 of SEQ ID NO: 42. In one embodiment, a variant of SEQ ID NO: 74 comprises amino acid residue E4 of SEQ ID NO: 74. In one embodiment, a variant of SEQ ID NO: 74 comprises amino acid residue D8 of SEQ ID NO: 74. In one embodiment, a variant of SEQ ID NO: 74 comprises amino acid residue D9 of SEQ ID NO: 74. In one embodiment, a variant of SEQ ID NO: 74 comprises amino acid residue K14 of SEQ ID NO: 74.

In one embodiment, a variant of SEQ ID NO: 42 is SEQ ID NO: 65 (DDTSAELLTEDISNLKNNNDITAENNN). In one embodiment, a variant of SEQ ID NO: 74 is SEQ ID NO: 79 (TSAELLTEDISNLKNNNDITAENNN).

In one embodiment, the polypeptide of the invention does not comprise or consist of the IpaA protein full-length (SEQ ID NO: 1, EMBL accession AL391753.1; NCBI Reference Sequence: WP_005063225.1), which is known to be cytotoxic upon cell transfection.

```
                                        SEQ ID NO: 1
MHNVNNTQAPTFLYKATSPSSTEYSELKSKISDIHSSQTSLKTPASVSEK

ENFATSFNQKCLDFLFSSSGKEDVLRSIYSNSMNAYAKSEILEFSNVLYS

LVHQNGLNFENEKGLQKIVAQYSELIIKDKLSQDSAFGPWSAKNKKLHQL

RQNIEHRLALLAQQHTSGEALSLGQKLLNTEVSSFIKNNILAELKLSNET

VSSLKLDDLVDAQAKLAFDSLRNQRKNTIDSKGFGIGKLSRDLNTVAVFP

ELLRKVLNDILEDIKDSHPIQDGLPTPPEDMPDGGPTPGANEKTSQPVIH

YHINNDNRTYDNRVFDNRVYDNSYHENPENDAQSPTSQTNDLLSRNGNSL

LNPQRALVQKVTSVLPHSISDTVQTFANNSALEKVFNHTPDNSDGIGSDL

LTTSSQERSANNSLSRGHRPLNIQNSSTTPPLHPEGVTSSNDNSSDTTKS

SASLSHRVASQINKFNSNTDSKVLQTDFLSRNGDTYLTRETIFEASKKVT

NSLSNLISLIGTKSGTQERELQEKSKDITKSTTEHRINNKLKVTDANIRN

YVTETNADTIDKNHAIYEKAKEVSSALSKVLSKIDDTSAELLTDDISDLK

NNNDITAENNNIYKAAKDVTTSLSKVLKNINKD.
```

In another embodiment, the polypeptide of the invention does not comprise or consist of SEQ ID NO: 43 (*Shigella sonnei* SipA protein, NCBI reference Sequence WP_052992066.1).

```
                                        SEQ ID NO: 43
NIEHRLALLAQQHTSGEALSLGQKLLNTEVSSFIKNNILAELKLSNETVS

SLKLDDLVDAQAKLAFDSLRNQRKNTIDSKGFGIGKLSRDLNTVAVFPEL

LRKVLNDILEDIKDSHPIQDGLPTPPEDMPDGGPTPGANEKTSQPVIHYH

INNDNRTYDNRVFDNRVYDNSYHENPENDAQSPTSQTNDLLSRNGNSLLN

PQRALVQKVTSVLPHSISDTVQTFANNSALEKVFNHTPDNSDGIGSDLLT

TSSQERSANNSLSRGHRPLNIQNSSTTPPLHPEGVTSSNDNSSDTTKSSA

SLSHRVASQINKFNSNTDSKVLQTDFFSRNGDTYLTRETIFEASKKVTNS

LSNLISLIGTKSGTQERELQEKSKDITKSTTEHRINNKLKVTDANTINYV

TETNADTIDKNHAIYEKAKEVSSALSKVLSKIDDTSAELLTDDISDLKNN

NDITAENNNIYKAAKDVTTSLSKVLKNINKD.
```

In another embodiment, the polypeptide of the invention does not comprise or consist of SEQ ID NO: 44 (*Shigella sonnei* SipA protein, NCBI reference Sequence WP_052981248.1).

```
                                        SEQ ID NO: 44
VAQYSELIIKDKLSQDSAFGPWSAKNKKLHQLRQNIEHRLALLAQQHTSG

EALSLGQKLLNTEVSSFIKNNILAELKLSNETVSSLKLDDLVDAQAKLAF

DSLRNQRKNTIDSKGFGIGKLSRDLNTVAVFPELLRKVLNDILEDIKDSH

PIQDGLPTPPEDMPDGGPTPGANEKTSQPVIHYHINNDNRTYDNRVFDNR

VYDNSYHENPENDAQSPTSQTNDLLSRNGNSLLNPQRALVQKVTSVLPHS
```

-continued

ISDTVQTFANNSALEKVFNHTPDNSDGIGSDLLTTSSQERSANNSLSRGH

RPLNIQNSSTTPPLHPEGVTSSNDNSSDTTKSSASLSHRVASQINKFNSN

TDSKVLQTDFFSRNGDTYLTRETIFEASKKVTNSLSNLISLIGTKSGTQE

RELQEKSKDITKSTTEHRINNKLKVTDANTINYVTETNADTIDKNHAIYE

KAKEVSSALSKVLSKIDDTSAELLTDDISDLKNNNDITAENNNIYKAAKD

VTTSLSKVLKNINKD.

In another embodiment, the polypeptide of the invention does not comprise or consist of SEQ ID NO: 45 (*Shigella sonnei* 53G's YopE protein, referenced under SEED reference fig|216599.1.peg.1346).

SEQ ID NO: 45
MSEKESFATSFNQKCLDFLFSSSGKEDVLRSIYSNSMNAYAKSEILEFSN

VLYSLVHQNGLNFENEKGLQKIVAQYSELIIKDKLSQDSAFGPWSAKNKK

LHQLRQNIEHRLALLAQQHTSGEALSLGQKLLNTEVSSFIKNNILAELKL

SNETVSSLKLDDLVDAQAKLAFDSLRNQRKNTIDSKGFGIGKLSRDLNTV

AVFPELLRKVLNDILEDIKDSHPIQDGLPTPPEDMPDGGPTPGANEKTSQ

PVIHYHINNDNRTYDNRVFDNRVYDNSYHENPENDAQSPTSQTNDLLSRN

GNSLLNPQRALVQKVTSVLPHSISDTVQTFANNSALEKVFNHTPDNSDGI

GSDLLTTSSQERSANNSLSRGHRPLNIQNSSTTPPLHPEGVTSSNDNSSD

TTKSSASLSHRVASQINKFNSNTDSKVLQTDFFSRNGDTYLTRETIFEAS

KKVTNSLSNLISLIGTKSGTQERELQEKSKDITKSTTEHRINNKLKVTDA

NTINYVTETNADTIDKNHAIYEKAKEVSSALSKVLSKIDDTSAELLTDDI

SDLKNNNDITAENNNIYKAAKDVTTSLSKVLKNINKD.

In another embodiment, the polypeptide of the invention is a fragment of SEQ ID NO: 1 and comprises or consists of a sequence starting from amino acids 2; 3; 4; 5; 6; 7; 8; 9; 10; 11; 12; 13; 14; 15; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; 185; 186; 187; 188; 189; 190; 191; 192; 193; 194; 195; 196; 197; 198; 199; 200; 201; 202; 203; 204; 205; 206; 207; 208; 209; 210; 211; 212; 213; 214; 215; 216; 217; 218; 219; 220; 221; 222; 223; 224; 225; 226; 227; 228; 229; 230; 231; 232; 233; 234; 235; 236; 237; 238; 239; 240; 241; 242; 243; 244; 245; 246; 247; 248; 249; 250; 251; 252; 253; 254; 255; 256; 257; 258; 259; 260; 261; 262; 263; 264; 265; 266; 267; 268; 269; 270; 271; 272; 273; 274; 275; 276; 277; 278; 279; 280; 281; 282; 283; 284; 285; 286; 287; 288; 289; 290; 291; 292; 293; 294; 295; 296; 297; 298; 299; 300; 301; 302; 303; 304; 305; 306; 307; 308; 309; 310; 311; 312; 313; 314; 315; 316; 317; 318; 319; 320; 321; 322; 323; 324; 325; 326; 327; 328; 329; 330; 331; 332; 333; 334; 335; 336; 337; 338; 339; 340; 341; 342; 343; 344; 345; 346; 347; 348; 349; 350; 351; 352; 353; 354; 355; 356; 357; 358; 359; 360; 361; 362; 363; 364; 365; 366; 367; 368; 369; 370; 371; 372; 373; 374; 375; 376; 377; 378; 379; 380; 381; 382; 383; 384; 385; 386; 387; 388; 389; 390; 391; 392; 393; 394; 395; 396; 397; 398; 399; 400; 401; 402; 403; 404; 405; 406; 407; 408; 409; 410; 411; 412; 413; 414; 415; 416; 417; 418; 419; 420; 421; 422; 423; 424; 425; 426; 427; 428; 429; 430; 431; 432; 433; 434; 435; 436; 437; 438; 439; 440; 441; 442; 443; 444; 445; 446; 447; 448; 449; 450; 451; 452; 453; 454; 455; 456; 457; 458; 459; 460; 461; 462; 463; 464; 465; 466; 467; 468; 469; 470; 471; 472; 473; 474; 475 476; 477; 478; 479; 480; 481; 482; 483; 484; 485; 486; 487; 488; 489; 490; 491 or 492 and ending at amino acid 631, 632 or 633 of SEQ ID NO: 1.

In another embodiment, the polypeptide of the invention is a fragment of SEQ ID NO: 1 and comprises or consists of a sequence starting from amino acids 477, 478, 479, 480, 481, 482; 483; 484; 485; 486; 487; 488; 489; 490; 491 or 492 and ending at amino acid 631, 632 or 633 of SEQ ID NO: 1.

In another embodiment, the polypeptide of the invention is a fragment of SEQ ID NO: 1 and comprises or consists of a sequence starting from amino acids 492 and ending at amino acid 631 of SEQ ID NO: 1.

In one embodiment, the polypeptide of the invention comprises or consists of 19 to 500 amino acids, preferably from 70 to about 400 amino acids, more preferably from about 90 to about 300 amino acids, even more preferably from about 110 to about 200 amino acids and still even more preferably from about 140 to about 160 amino acids.

As used herein, the term "polypeptide" means molecules formed from the linking, in a defined order, of amino acids, and of at least 19, 38, 57, 60, 70, 80, 90, 100, 125 or 150 amino acids.

In one embodiment, the polypeptide according to the invention has a length of at least 19, 38, 57, 60, 70, 80, 90, 100, 125 or 150 amino acids. In one embodiment, the polypeptide of the invention has a length of at least 151 amino acids.

In one embodiment, the polypeptide of the invention is SEQ ID NO: 5. SEQ ID NO: 5 consists in amino acids 483 to 633 of SEQ ID NO: 1.

SEQ ID NO: 5
GDTYLTRETIFEASKKVTNSLSNLISLIGTKSGTQERELQEKSKDITKST

TEHRINNKLKVTDANIRNYVTETNADTIDKNHAIYEKAKEVSSALSKVLS

KIDDTSAELLTDDISDLKNNNDITAENNNIYKAAKDVTTSLSKVLKNINK

D.

In one embodiment of the invention, said peptide has about 151, 155, 160, 175, 200, 250, 300 or 350 amino acids length and comprises the peptide sequence SEQ ID NO: 5.

In one embodiment, the polypeptide of the invention comprises SEQ ID NO: 5 and 1, 2, 3, 4, 5, 6, 7, 8, 9, 10 or more amino acids in C-term, and/or 1, 2, 3, 4, 5, 6, 7, 8, 9, 10 or more amino acids in N-term.

As used herein, "amino acids" are represented by their full name, their three letter code or their one letter code as well known in the art. Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

As used herein, the term "amino acids" includes both natural and synthetic amino acids, and both D and L amino acids. "Standard amino acid" or "naturally occurring amino acid" means any of the twenty standard L-amino acids commonly found in naturally occurring peptides. "Non-standard amino acid residue" means any amino acid, other than the standard amino acids, regardless of whether it is prepared synthetically or derived from a natural source. For example, naphtlylalanine can be substituted for tryptophan to facilitate synthesis. Other synthetic amino acids that can be substituted include, but are not limited to, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl.

As used herein, "amino acid" also encompasses chemically modified amino acids, including but not limited to salts, amino acid derivatives (such as amides), and substitutions. Amino acids contained within the polypeptides of the present invention, and particularly at the carboxy- or amino-terminus, can be modified by methylation, amidation, acetylation or substitution with other chemical groups which can change the polypeptide's circulating half-life without adversely affecting their activity. Additionally, a disulfide linkage may be present or absent in the polypeptides of the invention.

The polypeptides of the invention may comprise naturally standard amino acids or non-standard amino acids. Polypeptide mimetics include polypeptides having the following modifications: i) polypeptides wherein one or more of the peptidyl —C(O)NR— linkages (bonds) have been replaced by a non-peptidyl linkage such as a —CH$_2$-carbamate linkage (—CH$_2$OC(O)NR—), a phosphonate linkage, a —CH$_2$-sulfonamide (—CH$_2$—S(O)$_2$NR—) linkage, a urea (—NHC(O)NH—) linkage, a —CH$_2$-secondary amine linkage, or with an alkylated peptidyl linkage (—C(O)NR—) wherein R is C$_1$-C$_4$ alkyl; ii) polypeptides wherein the N-terminus is derivatized to a —NRR$^1$ group, to a —NRC(O)R group, to a —NRC(O)OR group, to a —NRS(O)$_2$R group, to a —NHC(O)NHR group where R and R$^1$ are hydrogen or C$_1$-C$_4$ alkyl with the proviso that R and R$^1$ are not both hydrogen; iii) polypeptides wherein the C terminus is derivatized to —C(O)R$^2$ where R$^2$ is selected from the group consisting of C$_1$-C$_4$ alkoxy, and —NR$^3$R$^4$ where R$^3$ and R$^4$ are independently selected from the group consisting of hydrogen and C$_1$-C$_4$ alkyl.

In one embodiment, the polypeptide of the invention comprises or consists in SEQ ID NO: 5 or a variant thereof. In one embodiment, a variant of SEQ ID NO: 5 binds to vinculin and/or talin with an equivalent affinity to the one of SEQ ID NO: 5. In one embodiment, a variant of SEQ ID NO: 5 conserves the activity of SEQ ID NO: 5 on cell proliferation and/or anchoring.

In one embodiment, a variant of SEQ ID NO: 5 comprises conservative amino acid substitutions as compared to the sequence of SEQ ID NO: 5.

As used herein, the term "conservative amino acid substitution" is defined herein as an amino acid exchange within one of the following five groups:
I. Small aliphatic, nonpolar or slightly polar residues: Ala, Ser, Thr, Pro, Gly;
II. Polar, negatively charged residues and their amides: Asp, Asn, Glu, Gln;
III. Polar, positively charged residues: His, Arg, Lys;
IV. Large, aliphatic, nonpolar residues: Met, Leu, Ile, Val, Cys;
V. Large, aromatic residues: Phe, Tyr, Trp.

In another embodiment, a variant of SEQ ID NO: 5 is a polypeptide having a sequence identity of at least 70%, preferably of at least 75, 80, 85, 90, 95, 96, 97, 98, 99% or more with SEQ ID NO: 5.

In another embodiment, a variant of SEQ ID NO: 5 is a polypeptide wherein 1, 2, 3, 4, or 5 amino acids from the sequence of SEQ ID NO: 5 is/are absent, or substituted by any amino acid, or wherein 1, 2, 3, 4 or 5 amino acids (either contiguous or not) is/are added.

In one embodiment, a variant of SEQ ID NO: 5 comprises amino acid residues D2, K16, K31, K44, K48, K58, K60, E72, D76, D79, K80, K89, K97, E108, D112, D113, K118, K135, K143 or K150 of SEQ ID NO: 5.

In one embodiment, a variant of SEQ ID NO: 5 comprises amino acid residues D2, K16, K31, K44, K48, K58, K60, E72, D76, D79, K80, K89, K97, E108, D112, D113, K118, K135, K143 and K150 of SEQ ID NO: 5.

In one embodiment, a variant of SEQ ID NO: 5 comprises at least one (e.g., 1, 2, 3, 4, 5, 6, 7, 8, 9, 10, 11, 12, 13, 14, 15, 16, 17, 18, 19 or 20) amino acid residues selected from the group consisting of D2, K16, K31, K44, K48, K58, K60, E72, D76, D79, K80, K89, K97, E108, D112, D113, K118, K135, K143 and K150 of SEQ ID NO: 5.

In one embodiment, a variant of SEQ ID NO: 5 comprises amino acid residue D2 of SEQ ID NO: 5. In one embodiment, a variant of SEQ ID NO: 5 comprises amino acid residue K16 of SEQ ID NO: 5. In one embodiment, a variant of SEQ ID NO: 5 comprises amino acid residue K31 of SEQ ID NO: 5. In one embodiment, a variant of SEQ ID NO: 5 comprises amino acid residue K44 of SEQ ID NO: 5. In one embodiment, a variant of SEQ ID NO: 5 comprises amino acid residue K48 of SEQ ID NO: 5. In one embodiment, a variant of SEQ ID NO: 5 comprises amino acid residue K58 of SEQ ID NO: 5. In one embodiment, a variant of SEQ ID NO: 5 comprises amino acid residue K60 of SEQ ID NO: 5. In one embodiment, a variant of SEQ ID NO: 5 comprises amino acid residue E72 of SEQ ID NO: 5. In one embodiment, a variant of SEQ ID NO: 5 comprises amino acid residue D76 of SEQ ID NO: 5. In one embodiment, a variant of SEQ ID NO: 5 comprises amino acid residue D79 of SEQ ID NO: 5. In one embodiment, a variant of SEQ ID NO: 5 comprises amino acid residue K80 of SEQ ID NO: 5. In one embodiment, a variant of SEQ ID NO: 5 comprises amino acid residue K89 of SEQ ID NO: 5. In one embodiment, a variant of SEQ ID NO: 5 comprises amino acid residue K97 of SEQ ID NO: 5. In one embodiment, a variant of SEQ ID NO: 5 comprises amino acid residue E108 of SEQ ID NO: 5. In one embodiment, a variant of SEQ ID NO: 5 comprises amino acid residue D112 of SEQ ID NO: 5. In one embodiment, a variant of SEQ ID NO: 5 comprises amino acid residue D113 of SEQ ID NO: 5. In one embodiment, a variant of SEQ ID NO: 5 comprises amino acid residue K118 of SEQ ID NO: 5. In one embodiment, a variant of SEQ ID NO: 5 comprises amino acid residue K135 of SEQ ID NO: 5. In one embodiment, a variant of SEQ ID NO: 5 comprises amino acid residue K143 of SEQ ID NO: 5. In one embodiment, a variant of SEQ ID NO: 5 comprises amino acid residue K150 of SEQ ID NO: 5.

The polypeptides described herein can be produced synthetically by chemical synthesis or enzymatic synthesis as it is well known in the art. Alternatively, nucleotide sequences encoding the polypeptides of the invention can be introduced into a protein expression vector and produced in a suitable host organism (e.g., bacteria, insect cells, etc.), then purified. An additional polypeptide ("tag") can be added on for the purpose of purifying or identifying or purifying the polypeptides. Protein tags make it possible, for example, for the polypeptides to be adsorbed, with high affinity, to a matrix, and for the matrix then to be washed stringently with suitable buffers without the complex being eluted to any significant extent, and for the adsorbed complex subsequently to be eluted selectively. Examples of protein tags which are known to the skilled person are a $(His)_6$ tag, a Myc tag, a FLAG tag, a hemagglutinin tag, a glutathione transferase (GST) tag, intein having an affinity chitin-binding tag or maltose-binding protein (MBP) tag. These protein tags can be located N-terminally, C-terminally and/or internally.

In one embodiment of the invention, the polypeptides as described here above are modified by means well-known in the art, for instance by the addition of one or more functional group such as a phosphate, acetate, lipid or carbohydrate group, and/or by the addition of one or more protecting group.

For example, the polypeptides can be modified by the addition of one or more functional groups such as phosphate, acetate, or various lipids and carbohydrates. The polypeptides of the invention can also exist as polypeptide derivatives. The term "polypeptide derivative" refers to compound having an amino group (—NH—), and more particularly, a peptide bond. Polypeptides may be regarded as substituted amides. Like the amide group, the peptide bond shows a high degree of resonance stabilization. The C—N single bond in the peptide linkage has typically about 40 percent double-bond character and the C=O double bond about 40 percent single-bond character. "Protecting groups" are those groups that prevent undesirable reactions (such as proteolysis) involving unprotected functional groups. Specific examples of amino protecting groups include formyl; trifluoroacetyl; benzyloxycarbonyl; substituted benzyloxycarbonyl such as (ortho- or para-) chlorobenzyloxycarbonyl and (ortho- or para-) bromobenzyloxycarbonyl; and aliphatic oxycarbonyl such as t-butoxycarbonyl and t-amiloxycarbonyl. The carboxyl groups of amino acids can be protected through conversion into ester groups. The ester groups include benzyl esters, substituted benzyl esters such as methoxybenzyl ester; alkyl esters such as cyclohexyl ester, cycloheptyl ester or t-butyl ester. The guanidino moiety may be protected by nitro; or arylsulfonyl such as tosyl, methoxybenzensulfonyl or mesitylenesulfonyl, even though it does not need a protecting group. The protecting groups of imidazole include tosyl, benzyl and dinitrophenyl. The indole group of tryptophan may be protected by formyl or may not be protected.

The modification of the polypeptides aims in particular to improve their life time in vivo. One type of modification is the addition to the N or C termini of the polypeptides of polyethylene glycol (PEG). PEG is known by the person skilled in the art to have many properties that make it an ideal carrier for polypeptides such as high water solubility, high mobility in solution and low immunogenicity. This modification also protects the polypeptides from exopeptidases and therefore increases their overall stability in vivo.

The other modifications used to prevent degradation of the polypeptides by endopeptidases or exopeptidases include N-terminal modifications such as acetylation or glycosylation, C-terminal modifications such as amidation and use of unnatural amino acids (β-amino and α-trifluoromethyl amino acids) at particular sites within the polypeptides.

Another alternative to increase polypeptide molecular size is the genetic fusion of the polypeptides to the Fc domain of human gamma immunoglobulin or the fusion of the polypeptides to albumin.

In one embodiment, the polypeptide of the invention binds to vinculin.

Vinculin (SEQ ID NO: 31) is composed by three repetitions (D1-D3 (SEQ ID NO: 11-13)) of a conserved domain consisting of two bundles of four helices, and a fourth D4 domain (SEQ ID NO: 14) containing only one helical bundle connected to a proline-rich unstructured region and the carboxyterminal F-actin binding domain. Under its inactive folded state, intramolecular interactions between the D1 (SEQ ID NO: 11) and D4 (SEQ ID NO: 14) domains prevent the access of VBSs to vinculin.

In one embodiment, the polypeptide of the invention binds to vinculin with an estimated $K_D$ in the femtoM range. The affinity between a polypeptide of the invention and vinculin may be characterized by any conventional technique known by the skilled artisan. Binding properties of a polypeptide to another polypeptide or to cells or tissues may generally be determined and assessed using immunodetection methods including, for example, ELISA, immunofluorescence-based assays, such as immuno-histochemistry (IHC) and/or fluorescence-activated cell sorting (FACS) or by surface plasmon resonance (SPR, BIAcore) or by isothermal titration calorimetry.

In one embodiment, the interaction of the polypeptide of the invention with vinculin induces the activation of vinculin, i.e., induces a shift from a resting or inactive state to an active state.

The term "resting state" or "inactive state" refers to the folded conformation of vinculin wherein the D1 aminoterminal α-helical bundle domain interacts with the carboxy-terminal tail domain, hindering ligand binding sites.

The term "activation" of vinculin refers to the disruption of the interaction between the head and tail of vinculin. As a consequence, vinculin conformation evolves in an open "active" state able to bind to F-actin in order to reinforce the anchorage of the actin cytoskeleton to membrane receptors and cell adhesion.

In one embodiment, the interaction of the polypeptide of the invention with vinculin induces the supra-activation of vinculin.

The term "supra-activation" of vinculin as used herein refers to the unraveling of additional sites of binding to D2 domain and possibly other domains of vinculin. As a consequence, vinculin promotes the scaffolding of large talin-vinculin complexes significantly reinforcing the association of the cytoskeleton to membrane receptors in the absence of mechanosensing.

For IpaA VBS1, as for all VBSs described to date, vinculin activation occurs through binding to the first helical bundle of the D1 domain, promoting major conformational changes that disrupt the D1-D4 intramolecular interactions and frees the vinculin F-actin binding region. The IpaA VBS2, on the other hand, interacts with the second helical bundle of D1 and its association with IpaA VBS1 results in a very high affinity and stable binding to D1 with an estimated $K_D$ in the femtoM range. Functional evidence seems to indicate that IpaA VBS3 cooperates with IpaA VBS 1-2 to stimulate bacterial internalization by host cells, but that intriguingly, it may act as IpaA VBS1 in promoting vinculin activation through interaction with the vinculin D1 first helical bundle.

In another embodiment, the polypeptide of the invention binds to talin.

In one embodiment, the polypeptide of the invention binds to vinculin and talin.

In one embodiment, the polypeptide of the invention binds to talin with an estimated $K_D$ in the nM range. The affinity between a polypeptide of the invention and talin may be characterized by any conventional technique known by the skilled artisan. Binding properties of a polypeptide to another polypeptide or to cells or tissues may generally be determined and assessed using immunodetection methods including, for example, ELISA, immunofluorescence-based assays, such as immuno-histochemistry (IHC) and/or fluorescence-activated cell sorting (FACS) or by surface plasmon resonance (SPR, BIAcore) or by isothermal titration calorimetry.

Another object of the invention is a nucleic acid encoding a polypeptide as described herein above.

In one embodiment, the nucleic acid of the invention comprises at least one, preferably at least 2, and more preferably the three VBS encoding sequences SEQ ID NO: 8-10:

VBS1:
(SEQ ID NO: 8)
ATATATAAAGCAGCAAAAGATGTAACCACTTCCCTATCAAAAGTATT

AAAGAATATC;

VBS2:
(SEQ ID NO: 9)
ATCTATGAAAAGGCAAAAGAAGTATCTAGCGCCCTCAGCAAGGTATT

GTCAAAAATT;

VBS3:
(SEQ ID NO: 10)
ATATTTGAAGCTTCAAAAAAAGTAACAAACTCCCTAAGTAATCTTAT

ATCTCTCATT;

or any nucleic acid sequence having at least 60; 65; 70; 75; 80; 85; 90; 95; 96; 97; 98; 99% identity with SEQ ID NO: 8; 9 and 10.

In one embodiment, the nucleic acid of the invention comprises at least one, preferably at least 2, and more preferably the three VBS encoding sequences SEQ ID NO: 69-71:

VBS1:
(SEQ ID NO: 69)
ATATATAAAGCAGCAAAAGATGTAACCACTTCCCTATCAAAAGTATT

AAAGAATATCAATAAGGAT;

VBS2:
(SEQ ID NO: 70)
ATCTATGAAAAGGCAAAAGAAGTATCTAGCGCCCTCAGCAAGGTATT

GTCAAAAATTGACGAT;

VBS3:
(SEQ ID NO: 71)
ACACGGGAAACGATATTTGAAGCTTCAAAAAAAGTAACAAACTCCCT

AAGTAATCTTATATCTCTCATTGGAACT;

or any nucleic acid sequence having at least 60; 65; 70; 75; 80; 85; 90; 95; 96; 97; 98; 99% identity with SEQ ID NO: 69; 70 and 71.

In one embodiment, the nucleic acid of the invention is SEQ ID NO: 6.

In another embodiment, the nucleic acid of the invention does not comprise or consist of full-length IpaA nucleic acid sequence (SEQ ID NO: 7).

In another embodiment, the nucleic acid of the invention does not comprise or consist of nucleic acid residues 3109 to 5010 of pINV_F6_M1382, referenced under NCBI accession number AY206439.1 (SEQ ID NO: 46).

In one embodiment, the nucleic acid of the invention comprises or consists in 171 to 1500 nucleotides, preferably from 210 to about 1200 nucleotides, more preferably from about 270 to about 900 nucleotides, even more preferably from about 330 to about 600 nucleotides and still even more preferably from about 420 to about 480 nucleotides.

In one embodiment, the nucleic acid sequence according to the invention has a length of at least 171, 180, 190, 200, 300, 400 or 450 nucleotides. In one embodiment, the nucleic acid sequence of the invention has a length of at least 453 nucleotides.

Another object of the invention is an expression vector comprising a nucleic acid sequence encoding the polypeptide as described here above. In one embodiment, said nucleic acid sequence is a nucleic acid as described here above. Examples of vector include, but are not limited to, a plasmid, a bacteriophage, a virus, a cationic vesicle or any other type of vector.

Another object of the invention is a composition comprising or consisting of at least one polypeptide, nucleic acid and/or vector of the invention.

Another object of the invention is a pharmaceutical composition comprising or consisting of or consisting essentially of at least one polypeptide, nucleic acid and/or vector of the invention and at least one pharmaceutically acceptable excipient.

Another object of the invention is a medicament comprising or consisting of or consisting essentially of at least one polypeptide, nucleic acid and/or vector of the invention.

As used herein, the term "consisting essentially of", with reference to a pharmaceutical composition or medicament, means that the at least one polypeptide, nucleic acid and/or vector of the invention is the only one therapeutic agent or agent with a biologic activity within said pharmaceutical composition or medicament.

Pharmaceutically acceptable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, for example, BHA, BHT, citric acid, ascorbic acid, tetracycline, and the like.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In addition, pharmaceutically acceptable excipients may comprise some excipients, such as, for example, surfactants (e.g. hydroxypropylcellulose); suitable carriers, such as, for example, solvents and dispersion media containing, for example, water, ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextrose, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose; and the like.

Another object of the invention is a polypeptide, a nucleic acid or a vector as described here above for treating or for use in the treatment of a proliferation and/or adhesion related disease.

Another object of the invention is a composition, a pharmaceutical composition or a medicament as described here above for treating or for use in the treatment of a proliferation and/or adhesion related disease.

Another object of the invention is a method for treating a proliferation and/or adhesion related disease, wherein the method comprises administering to the subject the composition, the pharmaceutical composition or the medicament of the invention.

Indeed, the Applicant herein demonstrated that the expression of a peptide of the invention by a cell induces the rapid anchoring of said cell to the support, independently of the stiffness of the substrate. Moreover, said expression slows down the division time and the velocity of migration of said cell. These results thus strongly support the therapeutic use of a peptide of the invention for treating a proliferation and/or adhesion related disease.

Without willing to be bound to a theory, the Applicant suggests that the expression of a peptide of the invention may lead to the anchoring of diseased cells to the substrate, and thereby (i) avoid dissemination of these cells (such as, for example, metastatic cells), and (ii) facilitate access to these cells by therapeutic agents or methods.

As used herein, the term "proliferation and/or adhesion related disease" refers to pathologies wherein abnormal cell proliferation and/or dysfunction in cell adhesion are observed. Abnormal cell proliferation and dysfunction in cell adhesion are mechanisms well known in the state of the art.

Proliferation and/or adhesion related diseases include but are not limited to, cancer, tumor, metastasis, inflammatory diseases and/or auto-immune disease.

Examples of cancers include but are not limited to, tumors, metastasis, carcinoma, melanoma, lymphoma, glioma, myeloma, neoplasm, leukemia, soft tissue cancer (such as, for example, soft tissue sarcoma), anal cancer, bladder cancer, bone cancer, breast cancer, cervical cancer, endometrial cancer, esophageal cancer, extrahepatic bile duct cancer, eye cancer, gall bladder cancer, gastric cancer, head and neck cancer, hypopharyngeal cancer, kidney cancer, laryngeal cancer, lip and oral cavity cancer, liver cancer, lung cancer, mesothelioma, metastatic squamous head and neck cancer, nasopharyngeal cancer, neuroblastoma, oral cancer, oropharyngeal cancer, ovarian cancer, pancreatic cancer, sinus and nasal cancer, parathyroid cancer, penile cancer, pheochromocytoma cancer, pituitary cancer, plasma cell neoplasm, prostate cancer, rectal cancer, salivary gland cancer, skin cancer, stomach cancer, testicular cancer, thymoma, thyroid cancer, urethral cancer, uterine cancer, vaginal cancer, vulvar cancer.

Examples of tumors include but are not limited to, malignant tumors, epithelial tumor, connective tissue neoplasm, sarcomas, fibroma, fibrosarcoma, dermatofibrosarcoma protuberans, desmoplastic fibroma, aggressive infantile fibromatosis, aponeurotic fibroma, collagenous fibroma, diffuse infantile fibromatosis, familial myxovascular fibromas, fibroma of tendon sheath, fibromatosis colli, infantile digital fibromatosis, juvenile hyaline fibromatosis, plantar fibromatosis, pleomorphic fibroma, oral submucous fibrosis, malignant fibrous histiocytoma, atypical fibroxanthoma, solitary fibrous tumor, myxoma/myxosarcoma, Brenner tumor, fibroadenoma, phyllodes tumor, synovial sarcoma, clear-cell sarcoma, lipoma/liposarcoma, chondroid lipoma, intradermal spindle cell lipoma, pleomorphic lipoma, lipoblastomatosis, spindle cell lipoma, hibernoma, myoma/myosarcoma, brain tumor, endocrine tumor, myeloma, extracranial germ cell tumor, Ewing's tumor, germ cell tumor, gestational trophoblastic tumor, carcinoid tumor, Wilm's tumor, Krukenberg tumor, bone tumor, cartilage tumor, osteoid osteoma, osteoblastoma, osteoma/osteosarcoma, chondroblastoma, giant cell tumor bone, Mullerian tumor, rhabdomyoma/rhabdomyosarcoma: embryonal rhabdomyosarcoma, sarcoma botryoides, alveolar rhabdomyosarcoma, leiomyoma/leiomyosarcoma, Askin's tumor, malignant hemangioendothelioma, soft tissue sarcomas.

Examples of carcinomas include, but are not limited to, basal cell carcinoma, adenocarcinoma, adrenocortical carcinoma, breast carcinoma, colon carcinoma, Merkel cell carcinoma, rhabdomyosarcoma, renal cell carcinoma, islet cell carcinoma, basal cell carcinoma, squamous cell carcinoma, ductal carcinoma in situ (DCIS), invasive ductal carcinoma.

Examples of sarcomas include, but are not limited to, soft tissue sarcoma, Kaposi's sarcoma, osteosarcoma, liposarcoma, sarcoma botryoides, Askin's tumor, chondrosarcoma, Ewing's tumor, malignant hemangioendothelioma, osteosarcoma, soft tissue sarcomas, alveolar soft part sarcoma, angiosarcoma, cystosarcoma phyllodes, dermatofibrosarcoma, desmoid Tumor, desmoplastic small round cell tumor, epithelioid sarcoma, extraskeletal chondrosarcoma, extraskeletal osteosarcoma, fibrosarcoma, gastrointestinal stromal tumor, hemangiopericytoma, hemangiosarcoma, leiomyosarcoma, liposarcoma, lymphangiosarcoma, lymphosarcoma, malignant fibrous histiocytoma, malignant peripheral nerve sheath tumor, neurofibrosarcoma, rhabdomyosarcoma, synovial sarcoma.

Examples of lymphomas include, but are not limited to, T-cell lymphoma, Hodgkin lymphomas, non-Hodgkin lymphomas, Burkitt lymphoma.

In one embodiment, the polypeptide, nucleic acid or vector of the invention is used for preventing or treating metastasis.

Examples of inflammatory diseases include, but are not limited to, acne vulgaris, asthma, inflammatory autoimmune diseases, autoinflammatory diseases, celiac disease, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, interstitial cystitis, atherosclerosis, allergies, myopathies, leukocyte defects and cancers.

Examples of autoimmune diseases include, but are not limited to, myocarditis, postmyocardial infarction syndrome, postpericardiotomy syndrome, subacute bacterial endocarditis, anti-glomerular basement membrane nephritis, interstitial cystitis, lupus nephritis comorbidity, autoimmune hepatitis, primary biliary cirrhosis, primary sclerosing cholangitis, antisynthetase syndrome, alopecia areata, autoimmune angioedema, autoimmune progesterone dermatitis, autoimmune urticarial, bullous pemphigoid, cicatricial pemphigoid, dermatitis herpetiformis, discoid lupus erythematosus, epidermolysis bullosa acquisita, erythema nodosum, gestational pemphigoid, hidradenitis suppurativa, lichen sclerosus, pemphigus vulgaris, pityriasis lichenoides and varioliformis acuta, Mucha-Habermann disease, psoriasis, systemic scleroderma, vitiligo, Addison's disease, autoimmune polyendocrine syndrome, autoimmune polyendocrine syndrome type 2, autoimmune polyendocrine syndrome type 3, autoimmune pancreatitis, diabetes mellitus type 1, autoimmune thyroiditis, Ord's thyroiditis, Graves' disease, autoimmune oophoritis, endometriosis, autoimmune orchitis, Sjogren's syndrome, autoimmune enteropathy, celiac disease, Crohn's disease, microscopic colitis, ulcerative colitis, antiphospholipid syndrome, aplastic anemia, autoimmune hemolytic anemia, autoimmune lymphoproliferative syndrome, autoimmune neutropenia, autoimmune thrombocytopenic purpura, cold agglutinin disease, essential mixed cryoglobulinemia, evans syndrome, IgG4-related systemic disease, paroxysmal nocturnal hemoglobinuria, pernicious anemia, pure red cell aplasia, thrombocytopenia, adiposis dolorosa, adult-onset Still's disease, ankylosing spondylitis, CREST syndrome, drug-induced lupus, enthesitis-related arthritis, eosinophilic fasciitis, Felty syndrome, juvenile arthritis, Lyme disease (chronic), mixed connective tissue disease, palindromic rheumatism, Parry Romberg syndrome, Parsonage-Turner syndrome, psoriatic arthritis, reactive arthritis, relapsing polychondritis, retroperitoneal fibrosis, rheumatic fever, rheumatoid arthritis, sarcoidosis, Schnitzler syndrome, systemic lupus erythematosus, undifferentiated connective tissue disease, dermatomyositis, fibromyalgia, inclusion body myositis, myositis, myasthenia gravis, neuromyotonia, paraneoplastic cerebellar degeneration, polymyositis, acute disseminated encephalomyelitis, acute motor axonal neuropathy, anti-N-Methyl-D-Aspartate receptor encephalitis, Balo concentric sclerosis, Bickerstaffs encephalitis, chronic inflammatory demyelinating polyneuropathy, Guillain-Barré syndrome, idiopathic inflammatory demyelinating diseases, Lambert-Eaton myasthenic syndrome, multiple sclerosis, narcolepsy, pediatric autoimmune neuropsychiatric disorder associated with *Streptococcus*, progressive inflammatory neuropathy, restless leg syndrome, stiff person syndrome, Sydenham chorea, transverse myelitis, autoimmune retinopathy, autoimmune uveitis, Cogan syndrome, Graves ophthalmopathy, intermediate uveitis, ligneous conjunctivitis, Mooren's ulcer, neuromyelitis optica, opsoclonus myoclonus syndrome, optic neuritis, scleritis, Susac's syndrome, sympathetic ophthalmia, Tolosa-Hunt syndrome, autoimmune inner ear disease, Ménière's disease, anti-neutrophil cytoplasmic antibody-associated vasculitis, Behçet's disease, Churg-Strauss syndrome, giant cell arteritis, Henoch-Schonlein purpura, Kawasaki's disease, leukocytoclastic vasculitis, lupus vasculitis, rheumatoid vasculitis, microscopic polyangiitis, polyarteritis nodosa, polymyalgia rheumatic, urticarial vasculitisa and vasculitis.

Examples of inflammatory autoimmune diseases include, but are not limited to, intestinal inflammatory condition such as Crohn's disease and ulcerative colitis; arthritis condition such as rheumatoid arthritis, psoriatic arthritis, ankylosing spondylitis and juvenile idiopathic arthritis; multiple sclerosis; uveitis; Wegener's disease; primary biliary cirrhosis; primary sclerosing cholangitis; asthma, transplant rejection (host versus graft disease); diabetes or graft versus host disease.

In one embodiment, the composition, the pharmaceutical composition or the medicament of the invention is to be administered orally, by injection, topically, nasally, buccally, rectally, vaginaly, intratracheally, by endoscopy, transmucosally, or by percutaneous administration.

The disclosed polypeptides or nucleic acids or vectors can be delivered to the target cells in a variety of ways. The delivery mechanism chosen will depend in part on the type of cell targeted and whether the delivery is occurring for example in vivo or in vitro. The skilled artisan will be able to adapt the delivery of the polypeptides or nucleic acid sequences of the invention.

In one embodiment, the composition, the pharmaceutical composition or the medicament of the invention is to be orally administered. Examples of formulations adapted to oral administration include, but are not limited to: solid forms, liquid forms and gels. Examples of solid forms adapted to oral administration include, but are not limited to, pill, tablet, capsule, soft gelatine capsule, hard gelatine capsule, caplet, compressed tablet, cachet, wafer, sugar-coated pill, sugar coated tablet, or dispersing/or disintegrating tablet, powder, solid forms suitable for solution in, or suspension in, liquid prior to oral administration and effervescent tablet. Examples of liquid form adapted to oral administration include, but are not limited to, solutions, suspensions, drinkable solutions, elixirs, sealed phial, potion, drench, syrup and liquor.

In one embodiment, the composition, the pharmaceutical composition or the medicament of the invention is to be administered by injection, preferably systemically injected. Examples of formulations adapted to systemic injections include, but are not limited to: liquid solutions or suspensions, solid forms suitable for solution in, or suspension in, liquid prior to injection. Examples of systemic injections include, but are not limited to, intravenous, subcutaneous, intramuscular, intradermal, intravitreal, and intraperitoneal injection, or perfusion. In another embodiment, when injected, the composition, the pharmaceutical composition or the medicament of the invention is sterile. Methods for obtaining a sterile pharmaceutical composition include, but are not limited to, GMP synthesis (GMP stands for "Good manufacturing practice").

In another embodiment, the composition, the pharmaceutical composition or the medicament of the invention is to be topically administered. Examples of formulations adapted to topical administration include, but are not limited to, sticks, waxes, creams, lotions, ointments, balms, gels, masks, leave-on washes and/or the like.

In one embodiment of the invention, the ointment is an oleaginous ointment; an emulsified ointment such as, for example, oil-in-water or a water-in-oil ointment; or a water-soluble ointment, preferably is an oleaginous ointment.

In one embodiment of the invention, the oleaginous ointment uses bases such as, for example, plant and animal oils; plant and animal fats; waxes; vaseline, such as, for example, white vaseline or vaseline oil; and paraffin such as, for example, liquid paraffin or paraffin oil.

In another embodiment, the composition of the invention can also be applied topically using a transdermal system, such as one of an acrylic-based polymer adhesive with a resinous crosslinking agent impregnated with the composition and laminated to an impermeable backing. Examples of formulations adapted to transdermal administration include, but are not limited to, ointment, paste, cream, film, balm, patch, such as, for example, transdermal patch, gel, liposomal forms and the like.

In one embodiment, the composition of the present invention can be administered topically as a transdermal patch, more particularly as a sustained-release transdermal patch. The transdermal patches can include any conventional form such as, for example, adhesive matrix, polymeric matrix, reservoir patch, matrix or monolithic-type laminated structure, and are generally comprised of one or more backing layers, adhesives, penetration enhancers, an optional rate controlling membrane and a release liner which is removed to expose the adhesives prior to application. Polymeric matrix patches also comprise a polymeric-matrix forming material. Suitable transdermal patches are described in more detail in, for example, U.S. Pat. Nos. 5,262,165; 5,948,433; 6,010,715 and 6,071,531, the disclosure of which are incorporated herein in their entirety.

In one embodiment, the composition, pharmaceutical composition or medicament of the invention may be used in conjunction with delivery systems that facilitate delivery of the agents to targeted organs or cells affected by a pathologic condition. For example, the composition, pharmaceutical composition or medicament of the invention may be PEGylated.

In one embodiment, the composition, the pharmaceutical composition or the medicament is administered in a sustained-release form. In another embodiment, the composition, the pharmaceutical composition or the medicament comprises a delivery system that controls the release of the agent.

Depending on the cell targeted, the skilled artisan can determine the technology needed for the introduction of the delivered nucleic acid sequences of the present application in the targeted cells.

The "targeted cells" or "targeted organ" as used herein refer to cells or organs affected by the diseases described below. In particular, targeted cells may include cells with abnormal proliferation or dysregulated adhesive properties.

For example, the polypeptides or the nucleic acids of the invention can be delivered through a number of direct delivery systems such as: electroporation, sonoporation, lipofection, calcium phosphate, plasmids, viral vectors, viral nucleic acids, phage nucleic acids, phages, cosmids, or via transfer of genetic material in cells or carriers such as cationic liposomes. Appropriate means for transfection include viral vectors, chemical transfectants, or physicomechanical methods such as electroporation and direct diffusion of nucleic acid sequences. Technics for delivering nucleic acids to cells as used in the present application are well known by the person skilled in the art. These technics are described in Guide to Molecular Cloning Technics (Berger S. L. and Kimmel A. R., 1987. *Methods in Enzymology.* 152:359-371). In particular cases, the methods will be modified and adapted to large nucleic acid molecules. Further, these methods can be used to target cells and in particular cell populations by using the targeting characteristics of the carrier.

There are a number of compositions and methods that can be used to deliver nucleic acids to cells, either in vitro or in vivo. These methods and compositions can largely be classified into two classes: viral based delivery systems and non-viral based delivery systems.

Viral based delivery systems for introducing nucleic acid molecules into cells involve the use of viral vectors. Since viral growth depends on the ability to get the viral genome into cells, viruses have devised clever and efficient methods for doing it. One such virus widely used for protein production is an insect virus, baculovirus. Baculovirus attracted the attention of researchers because during infection, it produces one of its structural proteins (the coat protein) to spectacular levels. If a foreign gene were to be substituted for this viral gene, it too ought to be produced at high level. Baculovirus, like vaccinia, is very large, and therefore foreign genes must be placed in the viral genome by recombination. To express a foreign gene in baculovirus, the gene of interest is cloned in place of the viral coat protein gene in a plasmid carrying a small portion of the viral genome. The recombinant plasmid is cotransfected into insect cells with wild-type baculovirus DNA. At a low frequency, the plasmid and viral DNAs recombine through homologous sequences, resulting in the insertion of the foreign gene into the viral genome. Virus plaques develop, and the plaques containing recombinant virus look different because they lack the coat protein. The plaques with recombinant virus are picked and expanded. This virus stock is then used to infect a fresh culture of insect cells, resulting in high expression of the foreign protein. Various viral vectors have also been used to transfect cells, such as bacteriophage, vaccinia virus, adenovirus, and retrovirus.

Non-viral based delivery systems are also known in the art for introducing nucleic acid molecules into targeted cells. One of these methods is microinjection, in which nucleic acid sequences is injected directly into the nucleus of cells through fine glass needles. Alternatively, nucleic acid sequences can be incubated with an inert carbohydrate polymer (dextran) to which a positively charged chemical group (DEAE, for diethylaminoethyl) has been coupled. The nucleic acid sequence sticks to the DEAE-dextran via its negatively charged phosphate groups. These large nucleic acid-containing particles stick in turn to the surfaces of cells, which are thought to take them in by a process known as endocytosis. Some of the nucleic acid evades destruction in the cytoplasm of the cell and escapes to the nucleus, where it can be transcribed into RNA like any other gene in the cell. In another method, cells efficiently take in nucleic acid sequence in the form of a precipitate with calcium phosphate. In electroporation, cells are placed in a solution containing nucleic acid and subjected to a brief electrical pulse that causes holes to open transiently in their membranes. Nucleic acid sequence enters through the holes directly into the cytoplasm, bypassing the endocytotic vesicles through which they pass in the DEAE-dextran and calcium phosphate procedures (passage through these vesicles may sometimes destroy or damage the nucleic acid sequence). The nucleic acid sequence can also be incorporated into artificial lipid vesicles, liposomes, which fuse with the cell membrane, delivering their contents directly into the cytoplasm. In an even more direct approach, used primarily with plant cells and tissues, the nucleic acid sequence is absorbed to the surface of tungsten micro projectiles and fired into cells with a device resembling a shotgun.

Another object of the invention is a capsule or a liposome that targets specifically a cell, an organ, a tissue or a site affected by a proliferation and/or adhesion related disease.

In one embodiment, the capsule or the liposome of the invention comprises at least one polypeptide, nucleic acid or vector as described here above.

Thus, the polypeptides or nucleic acid sequences can be encapsulated or vectorized for example, lipids such as liposomes, such as cationic liposomes (e. g., DOTMA, DOPE, DC-cholesterol) or anionic liposomes. Liposomes can further comprise proteins to facilitate targeting a particular cell, if desired. The polypeptide or the nucleic acid sequences of the invention and a cationic liposome can be administered to the blood afferent to a target organ or target cells affected by the diseases described above.

In one embodiment, the capsule or the liposome of the invention comprises a polypeptide, a nucleic acid, a vector, a composition, a pharmaceutical composition or a medicament of the invention.

In one embodiment, the composition, the pharmaceutical composition or the medicament of the invention is to be administered at a dose determined by the skilled artisan and personally adapted to each subject.

In one embodiment, a therapeutically effective amount of the polypeptide, nucleic acid or vector of the invention is administered to a subject in need thereof.

It will be understood that the total daily usage of the composition, pharmaceutical composition or medicament of the present invention will be decided by the attending physician within the scope of sound medical judgment. The specific therapeutically effective amount for any particular patient will depend upon a variety of factors including the disorder being treated and the severity of the disorder; the specific composition employed, the age, body weight, general health, sex and diet of the subject; the time of administration, route of administration, the duration of the treatment; drugs used in combination or coincidental with the polypeptide or nucleic acid sequence employed; and like factors well known in the medical arts. For example, it is well within the skill of the art to start doses of a therapeutic compound at levels lower than those required to achieve the desired therapeutic effect and to gradually increase the dosage until the desired effect is achieved.

In one embodiment, a therapeutically effective amount of the composition, pharmaceutical composition or medicament of the invention is administered at least once a day, twice a day, or at least three times a day.

In another embodiment, a therapeutically effective amount of the composition, pharmaceutical composition or medicament of the invention is administered every two, three, four, five, or six days.

In another embodiment, a therapeutically effective amount of the composition, pharmaceutical composition or medicament of the invention is administered every week, twice a week, every two weeks, or once a month.

In another embodiment, a therapeutically effective amount of the composition, pharmaceutical composition or medicament of the invention is administered every month for a period at least 2; 3; 4; 5; or 6 months.

In another embodiment, a therapeutically effective amount of the polypeptide, nucleic acid or vector of the invention ranges from about 1 µg to 5 g.

In another embodiment, a therapeutically effective amount of the polypeptide, nucleic acid or vector of the invention to be administered ranges from about 0.1 µg/kg to 1 g/kg.

In one embodiment, the method of the invention is for a chronic treatment, i.e., the composition, pharmaceutical composition or medicament of the invention, is administered for a prolonged period of time, such as, for example, for at least about 1 week, 1 month, 1 year or more.

In another embodiment, the method of the invention is for an acute treatment, such as, for example, a treatment with only 1, 2 or 3 administrations of the composition, pharmaceutical composition or medicament of the invention.

In another embodiment, the composition, pharmaceutical composition or medicament as described here above is to be administered in combination with another treatment for proliferation and/or dysfunction in cell adhesion, preferably another anti-cancer or an anti-tumoral agent.

Examples of anti-tumoral agent comprise but are not limited to: chemotherapy, radiation, surgery, protein kinases inhibitors, microtubules inhibitors, anti-metabolite agents a tumor vaccine or an immunostimulatory antibody.

In one embodiment of the invention, the method for treating cancer in a subject in need thereof, comprises administering to the subject the composition, the pharmaceutical composition or the medicament prior to, concurrent to and/or posterior to another anti-tumoral agent or cancer treatment.

In another embodiment, the subject is affected, preferably is diagnosed with a proliferation and/or adhesion related disease. In another embodiment, the subject of the invention is at risk of developing a proliferation and/or adhesion related disease. Examples of risk factor include, but are not limited to, genetic predisposition, familial history of proliferation and/or adhesion related disease or environmental factors.

In another embodiment, the subject of the invention is affected, preferably is diagnosed with a cancer. In another embodiment, the subject of the invention is at risk of developing a cancer. In another embodiment, the subject of the invention is in a remission stage following a cancer.

In another embodiment, the subject of the invention is affected, preferably is diagnosed with a tumor. In another embodiment, the subject of the invention is at risk of developing a tumor. In another embodiment, the subject of the invention is in a remission stage following a tumor.

In another embodiment, the subject of the invention is affected, preferably is diagnosed with metastasis. In another embodiment, the subject of the invention is at risk of developing metastasis. In another embodiment, the subject of the invention is in a remission stage following metastasis.

In another embodiment, the subject of the invention is affected, preferably is diagnosed with an inflammatory disease.

In another embodiment, the subject of the invention is affected, preferably is diagnosed with an auto-immune disease.

Another object of the invention is a method for inducing supra-activation of vinculin in a subject in need thereof, comprising administering to the subject a therapeutically effective amount of the polypeptide, nucleic acid or vector of the invention.

Another object of the invention is a method for inhibiting proliferation and/or migration of cells, preferably of cancer cells and/or tumor cells in a subject in need thereof, comprising administering to the subject a therapeutically effective amount of the polypeptide, nucleic acid or vector of the invention. In one embodiment, the method of the invention is for inhibiting migration of cells. In another embodiment, the method of the invention is for inhibiting the migration rate of cells. In another embodiment, the method of the invention is for inhibiting proliferation of cells.

Another object of the invention is a method for modulating (i.e., for inhibiting or activating) cell adhesion in a subject in need thereof, comprising administering to the subject a therapeutically effective amount of the polypeptide, nucleic acid or vector of the invention. In one embodiment, the method of the invention is a method for modulating cell adhesion independently of mechanosensing. Consequently, in one embodiment, the method of the invention is a method for modulating cell adhesion independently of the stiffness of the substrate, i.e., soft or hard substrate. In one embodiment, the method of the invention is a method for modulating cell adhesion whilst by-passing mechanosensing normally associated with the initial steps of cell adhesion.

Another object of the invention is a method for modulating, preferably for slowing down, the division time of cells, comprising administering a therapeutically effective amount of the polypeptide, nucleic acid or vector of the invention.

Another object of the invention is a method for modulating, preferably for slowing down, the velocity of migration of cells, comprising administering a therapeutically effective amount of the polypeptide, nucleic acid or vector of the invention.

Another object of the invention is a method for reinforcing cell adhesion, preferably for accelerating the dynamics of cell adhesion, comprising administering a therapeutically effective amount of the polypeptide, nucleic acid or vector of the invention. In one embodiment, the method of the invention is a method for reinforcing cell adhesion independently of the stiffness of the substrate, i.e., soft or hard substrate. In one embodiment, the method of the invention is a method for reinforcing cell adhesion whilst by-passing mechanosensing normally associated with the initial steps of cell adhesion.

The Applicant has demonstrated (see Examples) that the polypeptide of the invention allows rapid anchoring of a cell expressing said polypeptide to a support comprising a receptor for beta-1 integrin, such as, for example, fibronectin. Indeed, anchoring is detected about 1 minute or less after insertion of the polypeptide within a cell.

Therefore, the present invention further relates to non-therapeutic applications of the polypeptide of the invention, resulting from this rapid effect on cell adhesion.

For example, the polypeptide of the invention may be used for forming a coating of cells on a support coated with a receptor for beta-1 integrin, such as, for example, fibronectin. It may also be used in the field of bioprinting, wherein cells are anchored on a support in order to generate spatially-controlled cell patterns. Such applications may apply to, without limitation, the development of tissue-on-a-chip and organ-on-a-chip in tissue engineering, coating of prosthesis with cells, etc.

BRIEF DESCRIPTION OF THE DRAWINGS

FIG. 3 is a set of schemes representing IpaA that binds to the first helical bundle (D2a) of the vinculin D2 domain (HVD2). Proteolytic map from mass spectrometry analysis of HVD1D2 and A483 alone, or following cross-linking of the HVD1D2-A483 1:2 complex (arrows). Note that first bundle of D2 domain (D2a) is protected from trypsin proteolysis in the HVD1D2-A483 complex compared to proteins alone. HVD1D2 (vinculin D1-D2 alone), A483 (A483 alone), HVD1D2*Comp (complex 1:2 HVD1D2 and A483) and A483*Comp (complex 1:2 HVD1D2 and A483). Empty boxes: domains protected from proteolysis; grey boxes: domains sensitive to proteolysis; brackets: A483-HVD1D2 interactive domains that are protected upon complex formation but not in proteins alone.

FIG. 4 is a set of images and graphs showing vinculin-mediated cell adhesion enhanced by IpaA. A and G, Immunofluorescence analysis of C2.7 cells (CTRL) and GFP-A483 transfectants (A483). GFP fluorescence (IpaA); vinculin; actin. A, cells plated for 16 hours. Arrowheads: large peripheral focal adhesions (FAs). Arrows: ventral FAs. B, The percentage of cells showing FAs with a small (S), medium (M) and large (L) FAs was scored (Exp. Procedures). The results are representative of n(control)=37 and n(GFP-A483)=27 cells in 3 independent experiments. Distributions were compared using a Pearson's Chi-squared test ($p=5.41 \times 10^{-9}$). C, Box-plot of the median time between two divisions for GFP (93 cells, N=4) and GFP-A483 transfectants (40 cells, N=4). : p=0.002. D, Box-plot of the mean velocity of GFP (268 cells, N=4) and GFP-A483 transfectants (199 cells, N=4). *p=0.0007. E, Root of Median Square of displacement over time for GFP-(SlopeC-TRL=355998 µm·hr, $R^2$=0.97) and GFP-A483 transfectants (SlopeA483=300097 µm·hr, $R^2$=0.98). The slopes were analyzed using a covariance test (ANCOVA, $p<2\times10^{-16}$). F, Box-plot of the median cell surface for GFP control (444 cells, N=4) and GFP-A483 transfectants (300 cells, N=4), ****: $p<2\times10^{-16}$. G, cells plated for 15 min on Fn-coated. Arrowheads: large peripheral vinculin-rich structures. H, Cells were plated for 7 minutes prior to washing and processing for DAPI staining. Left, representative micrographs of indicated cells. Right, box plot of the median number of adherent cells per sample for control (4586 cells, n=6) and GFP-A483 transfectants (6383 cells, n=6). *: p=0.015. I, cells were perfused in a microfluidic chamber and allowed to adhere for 1 minute prior to shear stress application. Boxplot of the median resistance to shear stress for control (34 cells, N=2) and GFP-A483 (15 cells, N=1). ***: p=0.00039.

FIG. 5 is a graph showing the result of binding assays of A483 and A525 to vinculin. Solid phase binding assays between vinculin and IpaA derivatives showing that A483 have similar immunoreactivity to the αIpaA antibody. Coating: A483 (solid square) and A525 (empty circle); ligand: HV.

FIG. 7 is a set of photographs and graphs showing the effect of A483 on the cell adhesion properties A, and B, Comparison between the total cell surface of GFP control and GFP-A483 cells. A, Measure of the total cell surface at three time points (25%/50%/75%) per recorded cell track for GFP control (Left panel) and GFP-A483 (Right panel) expressing cells. B, Kernel density (Gaussian) estimation function (Frequency) of the mean cell surface area ($\mu m^2$) between GFP control (Black lane—GFP) and GFP-A483 (pointed lane—IpaA_483) expressing cells. C, and D, Comparison between the time of division of GFP control and GFP-A483 cells showing that GFP-A483 cells are divided in two groups with different median times of division. C, Kernel density (Gaussian) estimation function (Frequency) of the time of division between GFP control (Black lane —GFP) and GFP-A483 (dotted lane—IpaA_483) cells. D, Box-plot comparing the time between two divisions for both GFP control (GFP), Group I GFP-A483 (GFP-A483 I) and Group II GFP-A483 (GFP-A483 II) expressing cells. Kruskal-Wallis Chi-squared test (p-value=$1.81 \times 10^{-06}$). E, Immunofluorescence analysis of C2.7 cells (CTRL) and GFP-A483 transfectants (A483). GFP fluorescence (IpaA); vinculin (vinculin); vinculin with enhanced contrast (vinculin X) and actin (actin) plated for 7 and 30 minutes on Fn-coated coverslips. F, Cells were plated for 15 min prior to washing and processing for DAPI staining. Box plot of the median number of adherent cells per sample for GFP control (4822 cells, n=6) and GFP-A483 transfectants (6745 cells, n=6). n.s.: p=0.132.

FIG. 8 is a set of photographs showing the interaction between IpaA VBS3 and talin (H1-H4). A, IpaA constructs used in this study. The VBSs are depicted as boxes in IpaA full length (IpaA-FL), with the residue number corresponding to the first residue of the corresponding VBS. The first and last IpaA residues are annotated for the IpaA truncated derivatives. V5: V5 epitope. B, HeLa cells were transfected with IpaA derivatives, fixed and processed for immunofluorescence staining of the V5 epitope and talin. Representative fluorescence images are shown, with a larger magnification of the inset boxed in the left panels. Scale bar=5 µm. C, Native PAGE analysis of IpaA VBSs and talin H1-H4 interaction. 1. Purified talin H1-H4 was incubated with the indicated IpaA VBS peptides and analyzed using 6-18% gradient native PAGE. The talin H1-H4: IpaA VBS molar ratio is indicated, with 1 corresponding to a final concentration of 25 µM. The migration of talin H1-H4 and of the talin H1-H4:IpaA VBS3 complex are indicated.

FIG. 11 is a set of photographs and graphs showing Talin's requirement for IpaA-dependent Shigella anchoring to actin foci and invasion. HeLa cells were challenged with the indicated bacterial strain. Samples were fixed and processed for immunofluorescent staining of bacterial LPS (bacteria), talin and actin. The left panel corresponds to a lower magnification with the inset boxed. A, Representative micrographs of cells challenged with WT Shigella for the time indicated in minutes on the left, with a larger magnification of the inset boxed in the left panel. The arrows point to talin "cups" at bacterial cell contacts. Scale bar=5 µm. B, The average intensity of talin staining at actin foci was quantified and the recruitment expressed as a ratio relative to a corresponding cell control area. C, D, and E, Cells were treated with anti-talin siRNA prior to bacterial challenge. C, Relative intensity of actin foci. D, Representative micrographs of cells infected for 15 minutes with WT Shigella. Scale bar=5 µm. E, Percentage of internalized bacteria. F, G, and H, Cells were challenged for 15 minutes with the indicated bacterial strain. IpaA/FL-A: Shigella ipaA mutant complemented with full length IpaA; IpaA/DTBS: Shigella ipaA mutant complemented with IpaA ΔVBS3 (deleted for residues IpaA 489-511); IpaA/DCT: Shigella ipaA complemented with IpaA ΔVBS1-2 (deleted for residues IpaA 550-633); IpaA/DTBS-DCT: Shigella ipaA complemented with IpaA ΔVBS1-2-3 (deleted for residues IpaA 489-511 and 550-633). F, Representative micrographs for WT and ipaA infected cells. The arrows point to talin "cups" at bacterial cell contacts. Scale bar=5 µm. G, Average intensity of talin recruitment±SD. H, Average percentage of actin foci forming talin "cups"±SD. Wilcoxon rank sum test (p-value=$1.319 \times 10^{-5}$). Pearson's Chi-squared test (p-value=0.0006048).

EXAMPLES

Figure 1:
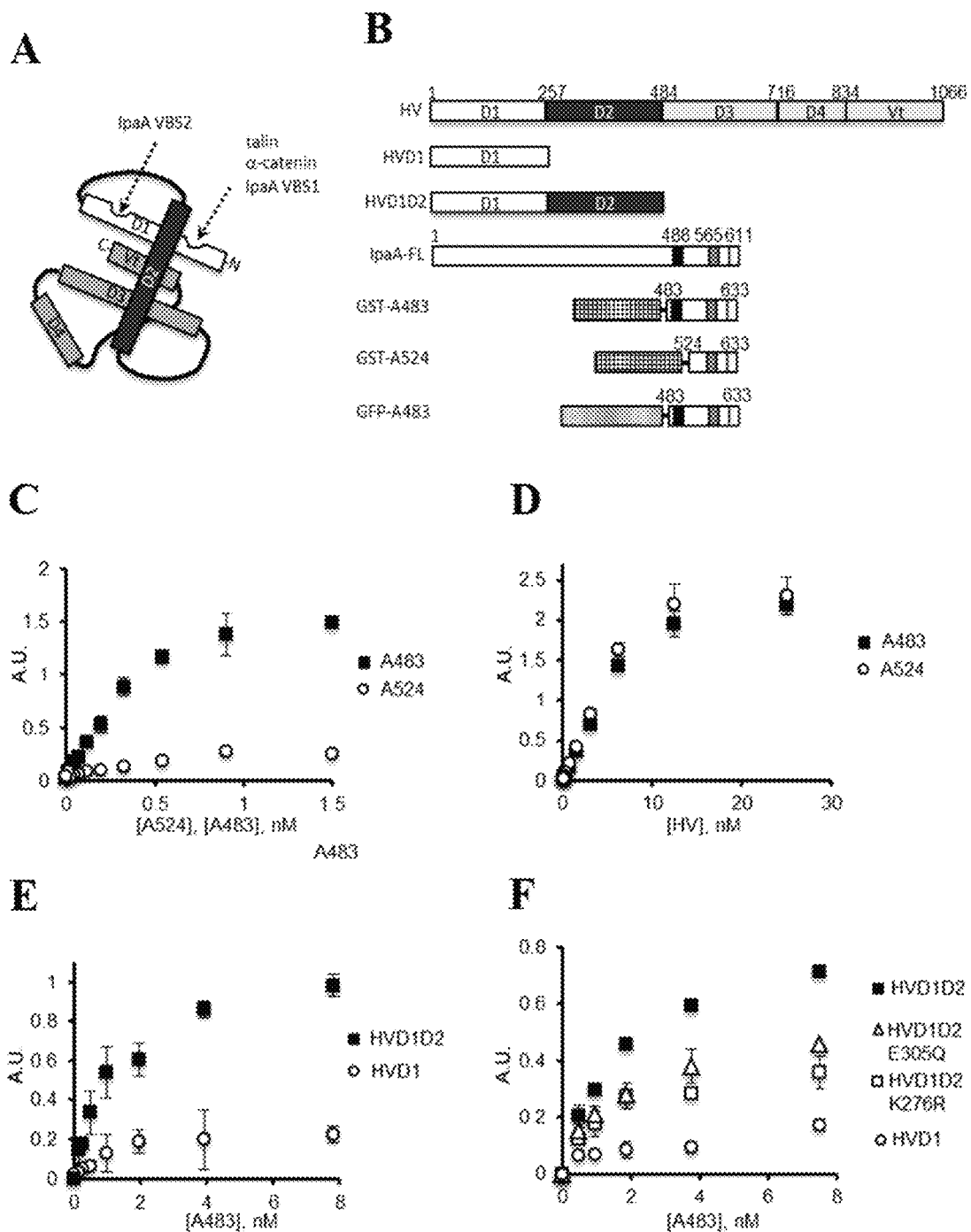
FIG. 1 is a set of schemes and graphs showing the interaction of A483 (SEQ ID NO: 5) and A524 (SEQ ID NO: 15) with full-length vinculin (HV). A, Scheme of folded vinculin. The binding sites and corresponding ligands in HVD1 (SEQ ID NO: 11) first and second helical bundles are indicated. B, Scheme of constructions with corresponding domains full-length vinculin or IpaA (IpaA-FL). Empty box: HVD1 domain; dark grey box: HVD2 (SEQ ID NO: 12) domain. IpaA VBS1 (grey); IpaA VBS2 (dark grey); IpaA VBS3 (solid). The numbers indicate the start residue of each domain. C-F, Solid phase binding assays between vinculin and IpaA derivatives. C, coating: HV; ligands: A483 (solid squares); A524 (empty circles). D, coating: A483 (solid squares) or A524 (empty circles); ligand: HV as ligand. E, coating: HVD1 (solid squares, SEQ ID NO: 11) or HVD1D2 (SEQ ID NO: 35) (empty circles); ligand: A483. F, coating: HVD1 (empty circles), HVD1D2 (solid squares), HVD1D2 K276R (SEQ ID NO: 36) (empty squares) or HVD1D2 E305Q (SEQ ID NO: 37) (empty triangles); ligand: A483.

The present invention is further illustrated by the following examples.
Materials and Methods
Generation of Expression Constructs (FIG. 1B)

Human vinculin constructs were generated by polymerase chain reaction using an upstream 5' GCG-CATATGCCAGTGTTTCATACG-3' (SEQ ID NO: 17) and two downstream 5'-CGTCGACTCACCAGGCATCTT-CATC-3' (SEQ ID NO: 18)/5'-CGTCGACTCAGTGTA-CAGCTGCTTTG-3' (SEQ ID NO: 19) primers for HVD1 (residues 1-258) and HVD1D2 (residues 1492) respectively, using a plasmid containing full-length human vinculin as template. The amplified sequences were digested with NdeI/SalI (New England Biolabs) restriction enzymes and ligated (T4 ligase, New England Biolabs) into a pET15b (Novagen) plasmid following manufacturer's recommendations. The HVD1D2 K276R and E305Q point mutations were obtained using the QuickChange II (Stratagene) method with 5'-GCATTGGCCTCCATAGACTCCCGTCT-GAACCAGGCCAAAGG-3' (SEQ ID NO: 20)/5'-CCTTTGGCCTGGTTCAGACGGGAGTCTATGGAGGC-CAATGC-3' (SEQ ID NO: 21) and 5'-GGCCATCAGACAGATCTTAGATCAAGCTG-GAAAAGTTGGTG-3' (SEQ ID NO: 22)/5'-CAC-CAACTTTTCCAGCTTGATCTAAGATCTGTCT-GATGGCC-3' (SEQ ID NO: 23) primers for HVD1D2 K276R and HVD1D2 E305Q respectively.

IpaA 483-633 (A483) constructs were generated by polymerase chain reaction using 5'-GCGATAT-CATGGCCAGCAAAGG-3' (SEQ ID NO: 24)/5'-GCGCGGCCGCTTAATCCTTATTGATATTC-3' (SEQ ID NO: 25) and 5' GGCGAATTCCCGGAGACACATATT-TAACACG-3' (SEQ ID NO: 26)/5'-GCCGTCGACT-TAATCCTTATTGATATTCT-3' (SEQ ID NO: 27) primers for GFP-A483 (SEQ ID NO: 28) and GST-A483 (SEQ ID NO: 29) respectively. GFP-A483 amplicon was cloned into a pcDNA3.1 NT-GFP Topo (Invitrogen) following manufacturer's recommendations. GST-A483 amplicon was digested with EcoRI/SalI restriction enzymes (Invitrogen and New England Biolabs) and ligated (T4 ligase, New England Biolabs) into a pGEX-4T-2 (GE Lifesciences) T7 expression plasmid. GST-A524 expression plasmids used in this work were previously described by Romarao et al. (*FEBS Lett.* 2007 Mar. 6; 581(5):853-7).
Yeast Double Hybrid Analysis The yeast two-hybrid analysis was performed using IpaA or IpaA1-482 as baits to screen a human placental RP1 library, according to standard procedures and the Y2H protocole (Hybrigenics services).
Protein Purification BL21 (DE3) chemically competent *E. coli* (Life Technologies) were transformed with pGEX 4T2-A483 (A483 is encoded by SEQ ID NO: 6), pGEX 4T2-A524 (A524 is encoded by SEQ ID NO: 32), pET15b-HVD1 (HVD1 is encoded by SEQ ID NO: 33) or pET15b-HVD1D2 (HVD1D2 is encoded by SEQ ID NO: 34) plasmids. The HVD1 and HVD1D2 were purified essentially as described (Izard et al., 2006; Papagrigoriou et al., 2004. *EMBO J.* 23(15):2942-51). For the IpaA derivatives, bacteria were grown until $OD_{600\ nm}$=1.0 and further grown in the presence of 0.5 mM IPTG for another 3 hours. Bacteria were pelleted and washed in binding buffer 25 mM Tris pH 7.4, 100 mM NaCl and 1 mM β-Mercaptoethanol, containing Complete™ protease inhibitor. Bacterial pellets were resuspended in $\frac{1}{50}^{th}$ of the original culture volume and lyzed using a cell disruptor (One shot model, Constant System Inc.). Proteins were purified by affinity chromatography using a GSTrap HP affinity column (GE Healthcare) followed by size exclusion chromatography (HiLoad S200, GE Healthcare). Protein concentration was determined using the BCA assay (Thermoscientific). Samples were dialyzed in binding buffer and stored aliquoted at −80° C. concentrations ranging from 1 to 10 mg/ml.
Native-PAGE Analysis Talin H1-H4 and IpaA peptides/proteins were incubated in binding buffer for 1 hour at 4° C. After incubation, the protein/peptides were mixed in a 2× Native loading buffer (62.5 mM Tris pH 6.8, Glycerol 25%) and separated by Tris-Glycine Native-PAGE electrophoresis. Gels were stained using standard colloidal Coomassie stain.
SEC-MALS The purified proteins IpaA 483-633 (A483), IpaA 524-633 (A524) and Talin H1-H4 (TlnH1-H4) were used at 20 μM equimolar concentrations and incubated at 4° C. for one hour in binding buffer (25 mM Tris-HCL pH 7.0, 100 mM NaCl and 1 mM β-Mercaptoethanol). The protein mixtures (200 μL) were analyzed by size-exclusion chromatography (SEC) on a Superdex 200 10/300 GL (GE Healthcare) using a Shimadzu Prominence HPLC. Multi-angle laser light scattering (MALS) was measured with a MiniDAWN TREOS (Wyatt Technology). Refractometry was monitored using an Optilab T-rEX (Wyatt Technology).
Crystallization, Structure Determination, and Crystallographic Refinement The IpaA/talin complex was screened against commercial crystallization solutions using the TTP LabTech Mosquito crystallization robot. Multiple crystallization conditions were identified. Reproducible plate shape crystals were grown in 0.1 mM Li sulfate, 0.1 mM Tris/HCl (pH 8.5), 30% PEG4000 at room temperature. The crystals were harvested and frozen after briefly soaking them into the reservoir solution supplemented with 20% ethylene glycol. A complete X-ray diffraction data set to 2.3 Å Bragg spacings was collected at 100 K using a wavelength of 1 Å on the SER-CAT beamline 221D at the Advanced Photon Source at Argonne National Laboratory (Argonne, Ill.). The dataset was merged and scaled using AutoProc and phased using Phaser. The refinement of the model structure was conducted with BUSTER. Manual rebuilding and model adjustment during the refinement was conducted with COOT. The final structure was validated with MolProbity.
ELISA Interaction Assay 96-well Maxisorp (Nunc) ELISA plates were coated with 30 nM full-length vinculin, vinculin constructs or IpaA proteins in binding buffer (25 mM Tris pH 7.4, 100 mM NaCl and 1 mM β-Mercaptoethanol). The wells were blocked with PBS-BSA 2%, washed and incubated with half series dilutions of IpaA or vinculin proteins in binding buffer+0.2% BSA at room temperature for one hour. After incubation the plates were washed and incubated with an anti-IpaA (dilution: 1/2000) polyclonal primary antibody (Tran Van Nhieu et al., 1997. EMBO J. 16(10):2717-29) or anti-vinculin (dilution: 1/2000) m11.5 monoclonal primary antibody (ref. V4505, Sigma-Aldrich) in binding buffer+ 0.2% BSA for one hour at room temperature. Plates were washed and incubated with an HRP-coupled secondary anti-rabbit or anti mouse Ig antibodies (dilution: 1/32000, Jackson ImmunoResearch) for one hour. The reaction was revealed by adding 100 µL of Tetramethylbenzidine (TMB) Liquid Substrate (ref. T0440, Sigma-Aldrich) for 15 minutes, stopped by adding 50 µL of 0.66 N $H_2SO_4$ (VWR), and the plates were read at 450 nm wavelength (Dynatech MR400).

Blue Native (BN)-Polyacrylamide Gel Electrophoresis (PAGE) Protein Native Gel analysis and complex crosslinking 25 µM of vinculin constructs were incubated with different molar ratios of IpaA proteins in a 1×BN-PAGE buffer (250 mM aminocaprionic acid, 25 mM Bis-Tris pH 7.0) at 4° C. for one hour. The protein mixtures were separated in a one-dimension native BN-PAGE electrophoresis. For vinculin-IpaA protein ratio assay, vinculin-IpaA bands containing the complexes separated by BN-PAGE were cut, sliced and boiled in a denaturant 2× Laemmli SDS buffer, then separated by standard SDS-PAGE electrophoresis. The second dimension SDS-PAGE gels were stained (colloidal Coomassie staining) and the density of the bands corresponding to vinculin and IpaA proteins (Image J) compared. The normalized vinculin:IpaA ratio of the complexes was compared using a non-parametric Kruskal-Wallis rank sum test (R statistical software).

For vinculin-IpaA complex crosslinking, the bands containing the complexes were cut, sliced and electroeluted in native conditions (15 mM Bis-Tris pH 7.0, 50 mM Tricine) inside a closed dialysis membrane (SpectraPor). The soluble complexes were recovered and their buffer exchanged twice into an amine-free crosslink buffer (25 mM Hepes, 100 mM NaCl) using 10MWCO ZEBA desalting columns (Thermo Scientific). The fractions containing the complexes were incubated for 1 hour at 4° C. with 10 mM sulfo-NHS and 5 mM EDC (Sigma-Aldrich) following manufacturer's recommendations. The crosslink reaction was stopped by adding 50 mM Tris pH 7.4, incubated for 20 minutes and denaturated in 2×SDS Laemmli buffer for 5 minutes at 95° C.

Talin H1-H4 and IpaA peptides/proteins at different molar ratios were incubated in binding buffer (25 mM Tris pH 7.4, 100 mM NaCl and 1 mM β-Mercaptoethanol) for 1 hour at 4° C. After incubation, the protein/peptides were mixed in a 2× Native loading buffer (62.5 mM Tris pH 6.8, Glycerol 25%) and separated by Tris-Glycine Native-PAGE electrophoresis. The Native PAGE electrophoresis gels were stained using standard colloidal Coomassie stain.

Immunostaining and Cell Adhesion Kinetics

C2.7 mice myoblasts cells were seeded at 2.5×10$^4$ cells in 5 mm rounded cell culture coverslips. Cells were transfected with 3 µg of pcDNA3.1 NT GFP-A483 plasmid, with 6 µL JetPEI transfection reagent (Polyplus) overnight following manufacturer's recommendations. Control and GFP-A483 transfected cells were fixed (3.7% PFA-PBS), permeabilized (0.1% Triton X-100, Sigma-Aldrich) and incubated with a 1/200 monoclonal m11.5 anti-vinculin antibody (ref. V4505, Sigma-Aldrich). Coverslips were washed and incubated with a 1/200 anti-mouse secondary antibody coupled to Alexa 546 (Jackson Research) and 1/200 Phalloidin A633 (Invitrogen), washed and mounted on slides using Dako mounting medium (Invitrogen). Samples were observed using a confocal microscopy with rotary disc (Roper Scientific®). Peripheral and ventral focal adhesion sizes (vinculin) were separated in three different categories (Small/ None, Medium and Large) and the size of their focal adherences scored from three independent experiments. The focal adhesion size's distributions between the control and GFP-A483 transfected cells were compared using a Pearson's Chi-squared test.

C2.7 mice myoblasts cells were seeded at 2.5×10$^5$ cells in a 10 cm cell culture petri dish (TPP). Cells were transfected with 15 µg of pcDNA3.1 NT GFP-A483 plasmid, with 45 µL JetPEI transfection reagent (Polyplus) overnight following manufacturer's recommendations. Control and transfected cells were detached and washed in a large volume of DMEM/Hepes (ref. 21063-045, Life Technologies) with 0.2% BSA and 50 ng/mL LPA (ref. L7260, Sigma-Aldrich) without FCS. Some 15,000 control/IpaA cells per well were seeded (DMEM/BSA/LPA, no FCS) in 24-well plates added with 5 mm rounded coverslips coated with 25 µg/mL fibronectin and blocked with 2% BSA-PBS 1×. Plates containing cells were centrifuged at 1000 g for 2 minutes, incubated at 37° C. and fixed (3.7% PFA-PBS) at different time points. Coverslips were stained with an anti-vinculin antibody+Phalloidin as described before (Immunostaining) or with a solution containing 1/200 DAPI (1 mg/mL) for number-of-cells adhesion tests. All coverslips were washed and mounted on slides using Dako mounting medium (Invitrogen) and observed using a confocal microscopy with rotary discs (Roper Scientific®).

FACS Sorting

C2.7 mice myoblasts cells were seeded at 2.5-5×105 cells in a 10 cm cell culture petri dish (TPP). Cells were transfected with 15 µg of pcDNA3.1-GFP or pcDNA3.1-NTGFP A483 plasmids, with 45 µL JetPEI transfection reagent (Polyplus) overnight following manufacturer's recommendations. Control and transfected (GFP or GFP-A483) cells were detached and washed in a large volume of DMEM+ Hepes (ref. 21063-045, Life Technologies) with 0.2% BSA without FCS, centrifuged and ~1×10$^6$ cells recovered in 2.5 mL DMEM 0.2% BSA medium for sorting. Flow cytometer FACSARIA II (BD Biosciences) was washed and the lasers and sorting system calibrated following manufacturer's recommendations. GFP and GFP-A483 transfected populations were sorted (Mode: Purity) and recovered in DMEM+10% FCS with 1×Penicillin/Streptomycin (Invitrogen). Around 15000 control GFP and GFP-A483 sorted cells were seeded per well in 24-well cell culture plates and left overnight for recovery.

Live Cell Videomicroscopy and Tracking

GFP and GFP-A483 sorted-cells were washed and added with 600 µL of sterile mineral oil (Ibidi). The plates were installed in a 37° C. 5%—$CO_2$ chamber of a Leica DRMB microscope and cell-containing fields were selected at random using a 20× objective in phase contrast. One acquisition was made each 3 minutes over 24 hours for control GFP and GFP-A483. Division, migration and cell surface parameters were obtained from four independent experiments. All statistical analysis was done in R statistical software. The mean velocity of migration was measured as the whole distance traveled by the cell divided by the time of migration for both GFP control (n(GFP)=268) and GFP-A483 (n(A483)=199) for all tracks followed for at least 5 hours. Medians were compared using a Wilcoxon rank sum test and dispersion by Median absolute dispersion (MAD) parameter. The measure of the two-dimensional (x and y) distance traveled by these cells was obtained from a function that quantifies the Median Square of displacement:

$$\text{MdSD} = f(t) = ([(x-xo)t]^2 + [(y-yo)t]^2)_{t,i}$$

MdSD: Median Square of displacement (μm/hr).
Md: Median of the cell square of displacement population i at t time point.
x: X coordinate of the nucleus of the cell at t time point.
xo: X coordinate of the nucleus of the cell at zero time point.
y: Y coordinate of the nucleus of the cell at t time point.
yo: Y coordinate of the nucleus of the cell at zero time point.

The root square of MdSD over time for GFP control and GFP-A483 was plotted over time and both fitted by linear regression. The slopes of the linear fit were compared using an ANCOVA test (linear model). The median cell surface was quantified as the mean of the surface for three time points (25%, 50% and 75%) of the whole cell track for control GFP and GFP-A483 cells, and dispersion measured by the Median absolute dispersion (MAD).

Microfluidics Cell Adhesion Assay

A microfluidic system similar previously was installed in a 37° C. temperature controlled Leica DRMB microscope and the microfluidic channels observed with a 20× phase contrast objective. The microfluidics chips were washed extensively with a sterile PBS 1× solution, coated with 25 μg/mL fibronectin (Calbiochem) and blocked with PBS 1×, 2% BSA (Sigma-Aldrich). Cell containing solution was applied to the chip system driven by hydrostatic pressure, and the flow verified. Hydrostatic pressure equal zero point was determined (zero flow) and the difference of pressure applied on the circuit was then equivalent to the difference of height between the zero point (h=0) and the final height using a calibrated stand.

Size Exclusion Chromatography

The purified proteins HVD1, A483, A524 and Talin H1-H4 were used at an equimolar concentration of 20 μM and incubated at 4° C. for one hour in binding buffer. The protein mixtures (200 μL) were injected in a FPLC chromatography system (FPLC Pharmacia) at 16° C. in a Superdex 75 HR 10/30 column (GE Healthcare) previously equilibrated with 10 volumes of binding buffer. The SEC system was calibrated with a Low Molecular Weight Gel Filtration Kit (ref. 17-0442-01, GE Healthcare) and the hydrodynamic radius (Angstroms) of the reference proteins (BSA, OVA, ChyA and RibA) correlated with the elution volume ($V_e$) using an Euler exponential equation: Hydrodynamic radius (Ang)=210.46 $e^{-0.189}$ $V_e$ (mL), with a correlation squared coefficient of $R^2$=0.9973. Fractions corresponding to elution volume 8-10 mLs were recovered, and analyzed by SDS-PAGE using 15% polyacrylamide gels.

Isothermal Titration Calorimetry

Vinculin, IpaA proteins and peptides were extensively dialyzed in binding buffer (25 mM Tris pH 7.4, 100 mM NaCl and 1 mM β-Mercaptoethanol). The final concentration of all proteins/peptides was measured using a BCA test (Thermo Scientific). Talin-IpaA binding was measured by microcalorimetry using an ITC200 calorimeter (MicroCal) at 25° C. 200 μL of 20-100 μM of talin H1-H4 protein was added to the cell and binding in the presence of different concentrations of IpaA VBS1, VBS2 or VBS3 peptides was measured. In other experiments, 200 μL of a 16 μM equimolar mix of A483:HVD1 was incubated for one hour at room temperature prior to addition to the cell. Binding to talin H1-H4 (100 μM) was measured. Typically, 20-40 injections of 2 μL of ligand were made with intervals of 320 seconds between each addition, with a reference power of 12 μcal/sec. Data were analyzed using the MicroCal software provided by manufacturer.

Cell Culture and *Shigella* Bacterial Strains

All *Shigella* lexneri strains used in this work were previously described. *Shigella* WT (Tran Van Nhieu et al., 1997), the ipaA/IpaA mutants complemented with a recombinant plasmid encoding full length IpaA, ipaA/pcr2.1 containing an empty pCR2.1 plasmid, ipaA/IpaAΔCter with IpaA deleted for the carboxy terminal region A550-633 were described in Izard et al., 2006. ipaA/IpaAΔVBS3 with IpaA deleted for residues Δ489-511 and ipaA/IpaAΔΔ with IpaA deleted for residues Δ489-511 and Δ550-633 were described in Park et al., 2011. *J. Biol. Chem.* 286(26):23214-21. Bacterial strains were cultured in trypticase soy broth (TCS) medium at 37° C., when specified; antibiotics were added at the following concentrations: carbenicilin 100 μg/mL, kanamycin 20 μg/mL. HeLa cells were from ATCC. HeLa cells were incubated in RPMI (Roswell Park Memorial Institute) medium containing 5% FCS (fetal calf serum, Gibco®) in an incubator with 5% $CO_2$.

siRNA Transfection

HeLa cells were seeded at a density of 105 cells in wells containing a 22×22 mm coverslip, in a 6-well plates. The following day, cells were transfected with of anti-talin 1 siRNA (Stealth Select RNAi, catalog no. 1299003, Invitrogen, oligo 804; sequence: 5-CCAAGAACGGAAAC-CUGCCAGAGUU-3' (SEQ ID NO: 30)) duplex at the indicated concentrations and time periods. The efficiency of talin expression inhibition was tested using cell crude lysates and anti-talin Western-blot analysis.

Cell Challenge with *Shigella* Strains

HeLa cells were seeded at 1×10$^5$ cells in 33 mm-diameter wells in diameter containing a sterile coverslip. One day after and immediately before infection, cells were washed three times with EM medium at 22° C. Different *Shigella* bacterial strains were grown in TCS medium to exponential phase, washed in EM medium and diluted to $OD_{600\,nm}$=0.1. The IpaA *Shigella* strains were incubated for 10 minutes in the presence of 10 μg/mL polylysine, washed and used to infect HeLa cell line prepared as described before. Infected cell cultures were incubated for 15 minutes at 22° C. to allow adhesion of the bacteria, and then transferred at 37° C. for 5, 10, 12, 15 and 30 minutes. After incubation, the different infected cell lines were fixed (3.7% PFA-PBS), permeabilized (0.1% Triton X-100, Sigma-Aldrich) and incubated with 1/400 monoclonal 8d4 anti-talin antibody (ref. T3287 Sigma-Aldrich). Coverslips were washed and incubated with a 1/200 anti-mouse secondary antibody coupled to Alexa 546 (Jackson ImmunoResearch) and 1/200 Phalloidin A633 (Invitrogen), washed and mounted on slides using Dako mounting medium (Dako, Agilent Technologies). Samples were observed using a confocal microscopy with rotary disc (Roper Scientific®) using a 63× objective.

Samples were also observed in an epifluorescence microscope DMRIBe (Leica) equipped with a 63× objective and an EM-CCD Cascade 512B camera (Roper Scientific). For each sample, more than thirty stack fields were acquired for each condition in two independent experiments. The results are expressed as the fluorescence intensity ratio of talin between the foci and the cytoplasm (R) using the following formula:

$$R = (I_F - I_o)/(I_C - I_o)$$

$I_F$: Medium intensity of talin at the entry foci.
$I_C$: Average intensity of talin in the cytoplasm of the infected cell.

$I_O$: Medium intensity of background in a region containing neither cells nor bacteria.

Bacterial-Induced Foci Formation and Invasion

Control and siRNA talin transfected cells were infected with WT *Shigella* strain for 30 minutes, fixed, permeabilized and incubated with 1/500 polyclonal anti-LPS antibody (Flex V). Coverslips were washed and incubated with a 1/200 anti-rabbit secondary antibody coupled to Alexa 546 (Jackson ImmunoResearch) and 1/200 Phalloidin A647 (Invitrogen), washed and mounted on slides in Dako mounting medium (Dako, Agilent Technologies). Samples were analyzed using an Eclipse Ti microscope (Nikon) equipped with a 63× objective, a CSU-X1 spinning disk confocal head (Yokogawa), and a Coolsnap HQ2 camera (Roper Scientific Instruments), controlled by the Metamorph 7.7 software. The percent of internalized bacteria was scored as the ratio between the number of internalized bacteria per foci and the number of total bacteria in found in the foci (n(control)=27, n(siRNA$^{Tln}$)=23) in two independent experiments. The percent of bacteria showing an actin intimate recruitment was scored as the ratio between the number of bacteria with actin intimate recruitment per foci and the number of total bacteria in the foci in two independent experiments. For control and anti-talin siRNA transfected cells, the percent of internalized bacteria and the percent of bacteria showing an actin intimate recruitment was compared using a non-parametric Wilcoxon rank sum test.

To quantify the size distribution of *Shigella* actin foci, we divided the foci in three classes: Small, Medium and Large. The size of control (n(control)=27) and siRNA talin (n(siRNA$^{Tln}$)=23) *Shigella*-induced foci were classified into this three categories, arranged in a contingency table and its distributions compared using a Pearson's Chi-squared test.

Example 1: Vinculin Supra-Activation by the *Shigella* Type III Invasion Effector IpaA The *Shigella* Type III Effector IpaA Induces a Novel Conformation of Vinculin Unveiling Additional Binding Sites.

We first measured the interaction of A483 (SEQ ID NO: 5) or A524 (SEQ ID NO: 15), containing IpaA VBS1/3 or IpaA VBS1/2, respectively, with full-length vinculin (HV) in solid phase assays. Classical hyperbolic saturation binding curves were obtained for A483 and A524. Strikingly, a large difference was observed in the plateau between the two proteins, indicating that human vinculin construct (HV) (SEQ ID NO: 16) harbored more binding sites for A483 (SEQ ID NO: 5) compared to A524 (SEQ ID NO: 15).

These results were unexpected, since vinculin activating ligands have been described to bind to a single site on the D1 domain of vinculin. When reverse binding assays were performed, whereby IpaA constructs were immobilized on the solid phase and HV used as a soluble ligand, similar saturation curves were observed for A483 and A524, plateauing at similar ligand concentrations (25 nM) (FIGS. 1 C and D). These results suggested that, despite the presence of the IpaA VBS3 in A483, the stoichiometry of A483:HV and A524:HV was similar at saturating concentrations of HV, probably due to steric hindrance. The difference in the A483:HV stoichiometry observed for A483 depending on its immobilized or soluble state was consistent with more binding of soluble A483 molecules per immobilized HV molecule. This suggested that while A524 bound to the HVD1 domain (SEQ ID NO: 11), the presence of IpaA VBS3 revealed novel sites on other HV domains. The immunoreactivity of the anti-IpaA antibodies was found to be similar for A482 and A524 (FIG. 5). To test this, we assayed the binding of A483 to vinculin derivatives containing only amino acid residues 1 to 257 of HV (HVD1) (SEQ ID NO: 11) or amino acid residues 1 to 484 of HV (HVD1D2) (SEQ ID NO: 35) As shown in FIG. 1E, A483 bound to HVD1 and HVD1D2, but as for HV, a higher binding plateau was observed for HVD1D2 relative to HVD1, consistent with novel binding sites on the vinculin D2 domain (HVD2).

Similar to HVD1 (SEQ ID NO: 11), HVD2 (SEQ ID NO: 12) contains two four-helical-bundles, with the amino-terminal bundle (D2a) sharing most similarities with the first bundle to HVD1 (D1a) (FIG. 3). The IpaA VBS3 peptide alone was proposed to interact with the HVD1 first bundle (FIG. 1A). However, in the context of A483, this interaction is unlikely to occur because of the very high affinity of IpaA VBS1 associated with IpaA VBS2 for the first and second helical bundles of HVD1, respectively (FIG. 1A). We reasoned that when constrained during the A483:HVD1D2 interaction, IpaA VBS3 could interact with the HVD2 first helical bundle. We thus designed mutations predicted from the structural alignment of the HVD1 and HVD2 first bundles, based on the previous identification of contact residues between IpaA VBS1 and the first bundle of HVD1. An HVD1D2 derivative containing the conservative mutations K276R and E305Q in the D2 domain was generated and tested for binding to A483. As shown in FIG. 1F, A483 bound to HVD1D2-K276R and HVD1D2-E305Q with a similar affinity as HVD1D2, but saturation occurred at a lower plateau indicating a decreased number of binding sites.

Together, the results are consistent with the IpaA VBS3 unveiling new sites on the vinculin D2 domain.

Figure 2:
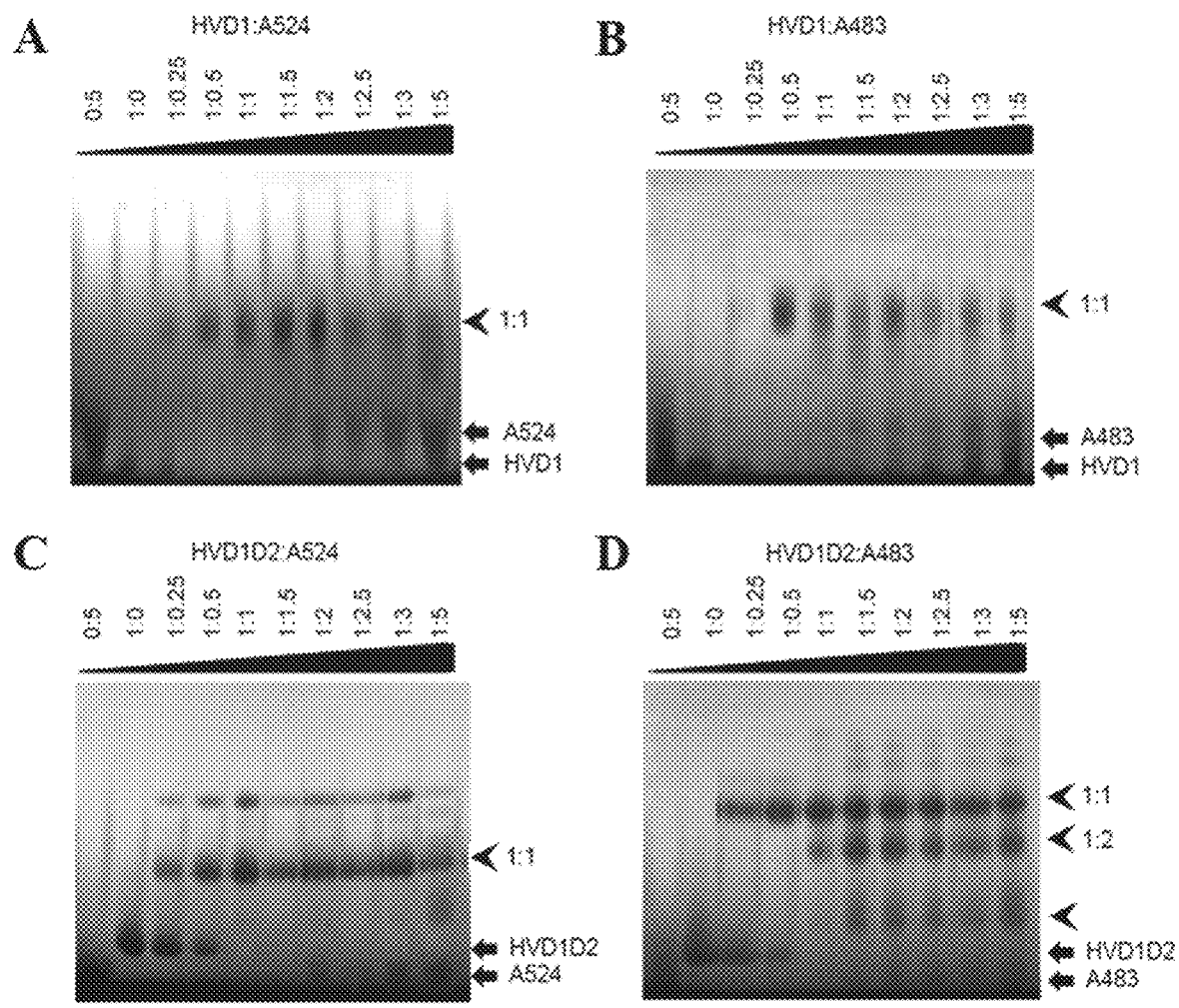
FIG. 2 is a set of photographs showing the formation of vinculin and IpaA derivatives complexes analyzed by BN-PAGE and Coomassie staining analysis of. Lanes: 1-10, protein mixture at the molar ratio indicated above each lane. A, HVD1 and A524; B, HVD1 and A483; C, HVD1-D2 and A524; D, HVD1-D2 and A483. A, and B, 6-18% polyacrylamide gradient gels; C, and D, 4.5-16% polyacrylamide gradient gels. Arrowheads indicate protein alone, or complex migration at the indicated molar ratio.
Figure 6:
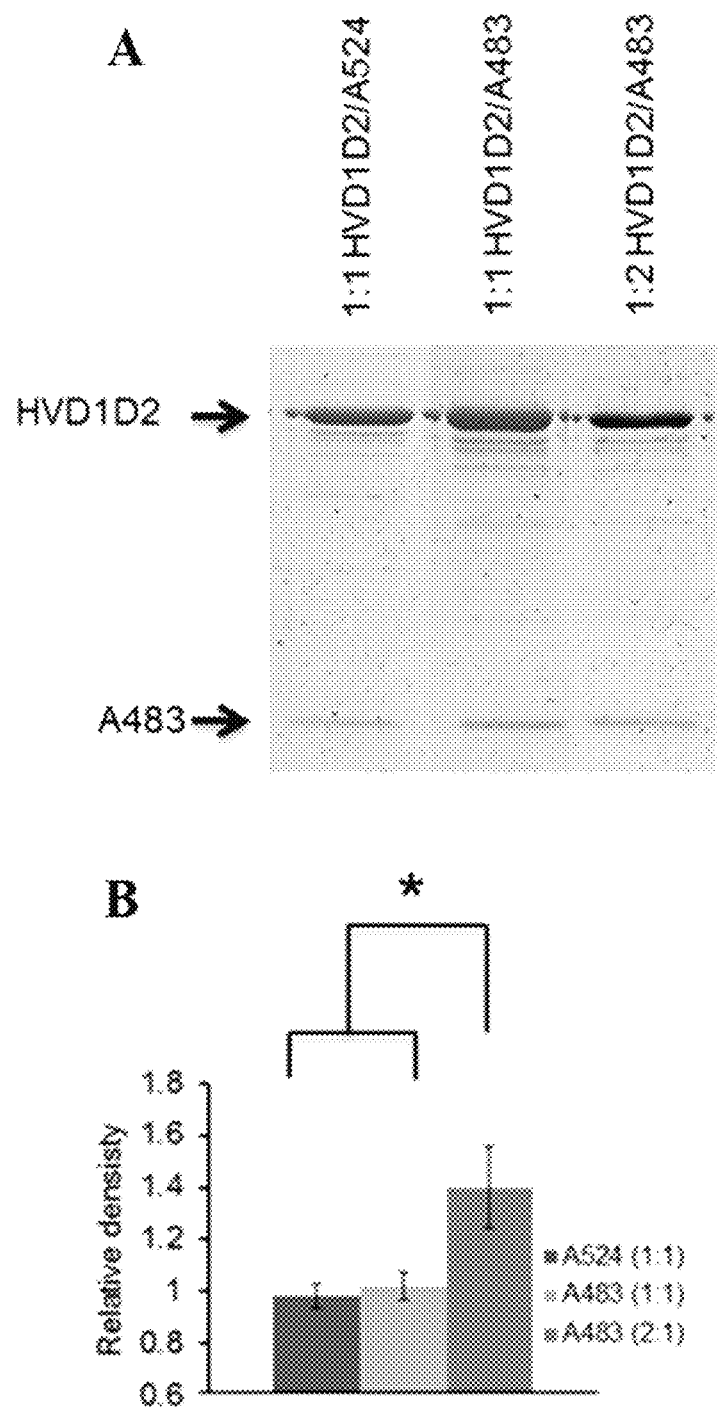
FIG. 6 is a set of photographs and graphs showing stoichiometry analysis of the A483-HVD1D2 complexes. A, SDS-PAGE (15%) second dimension electrophoresis showing the amount of HVD1D2 (upper band) and A483 (lower band) recovered from BN-PAGE sliced complexes. Left: complex 1:1 of HVD1D2 and A524; center: complex 1:1 of HVD1D2 and A483; right: complex 2:1 of A483 and HVD1D2. B, Amount of IpaA and HVD1D2 in 1:1 and 1:2 complexes measured by densitometry. IpaA524-633:HVD1D2 ratio for the 1:1 complex (Dark, left), IpaA483-633:HVD1D2 for 1:1 complex (Light grey, center) and for 2:1 complex (Dark grey, right). Kruskal-Wallis Chi-squared test (p-value=0.01458).

We next studied the formation of different IpaA-vinculin complexes in solution using BN-PAGE native gels. One complex was observed when HVD1 was incubated with A483, or when HVD1 or HVD1D2 was incubated with A524 at the lowest molar ratio of 1:0.025 (FIG. 2A-C, arrowhead 1:1). When HVD1D2 was incubated with A483, however, additional complexes could be observed at molar ratio of 1:1 and above (FIG. 2D, arrowheads). The analysis of these complexes following protein band excision from the BN gel, by further analysis by SDS-PAGE and Coomassie staining revealed a stoichiometry consistent with 1:1 for complexes observed in all samples at a 1:0.25 molar ratio (FIG. 6A-B). In contrast, the additional HVD1D2:A483 complex showed a 1:2 stoichiometry (FIG. 2D, arrowhead; FIG. 6B). These results were consistent with the solid-phase assays indicating that A483 binds to additional sites on HVD2. The sequential formation of 1:1 and 1:2 HVD1D2:A483 complexes with increasing molar ratio suggested allosteric changes, whereby binding of A483 to HVD1 occurred first, revealing an additional binding site on HVD2.

To map interactions between A483 and HVD1D2, protein complexes eluted from native gels were cross-linked, subjected to proteolysis and analyzed using LC-mass spectrometry. The proteolytic digestion profiles of individual proteins compared to the HVD1D2:A483 1:2 complex shown in FIG. 3, were clearly indicative of protection consistent with interaction between A483 and HVD1D2. Protection was observed for the all IpaA VBS (1, 2 and 3) when in complex with HVD1D2, which was not observed for A483 alone (FIG. 3). Protection was observed in the first four-helix-bundle of HVD1 (D1a), as expected from previous structural characterization of the IpaA VBS1:HVD1 complex. In contrast to what could be expected from the structural characterization of IpaA VBS2 in complex with HVD1, however, little difference in protection could be detected in the second HVD1 bundle between the proteins alone and the cross-linked complex, which may be explained by the low density of reactive groups exposed to the cross-linking agent in this particular bundle. Interestingly, protection was observed for IpaA VBS3 and the first four-helix-bundle of HVD2 (D2a) in the HVD1D2:A483 1:2 complex (FIG. 3). These results suggest an interaction between IpaA VBS3 and the first bundle of HVD2, consistent with the solid phase and native gel assays' results.

Figure 23:
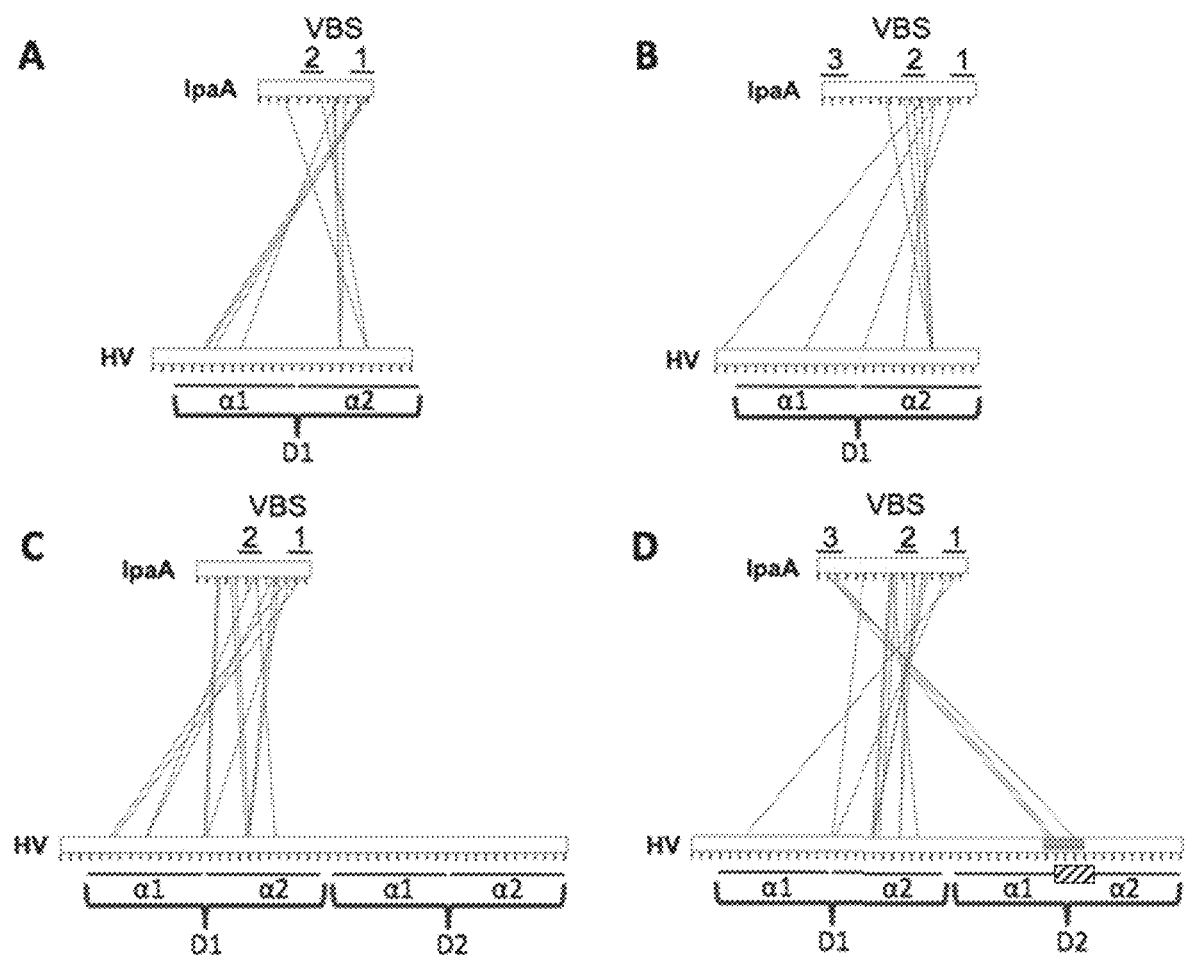
FIG. 23 is a set of EDC crosslink maps from mass spectrometry analysis (LC-ESI/TOF) of vinculin domains D1 (A and B) and D1D2 (C and D) with A524 (A and C) and A483 (B and D) following the extraction of HVD1D2:IpaA 1:1 complexes separated by SDS-PAGE electrophoresis. Black dashed box: interaction of the IpaA VBS3 with the first bundle of the vinculin D2 domain (HVD2).

Analysis of the cross-linked peptides enhanced intermolecular links between A524 or A483 and HVD1 or HVD2 (Table 1 and FIG. 23). For the A524:HVD1 complex, peptide links were detected consistent with the "canonical" conformer expected from previous structural studies indicating interactions between IpaA VBS1 and VBS2 with the HVD1 first and second four-helix-bundles, respectively. Links confirming this canonical interaction were observed for all complexes. Isolated links could be detected, suggestive of a conformer with an opposite interaction between A524 and HVD1, with IpaA VBS1 interaction and IpaA VBS2 with the second bundle and first bundle of D1, respectively. For the A524:HVD1D2 complex, two additional links were also between IpaA VBS11 and the D2 second bundle. For A483, an important number of links indicated the existence of the opposite-interaction conformer with IpaA VBS3 interacting with the D1 first bundle and IpaA VBS1 interacting with the second bundle of D2. This conformer is consistent with the similar mode of interaction between IpaA VBS1 or VBS3 and HVD1 (Park et al., 2011), and further suggests that A483 can engage HVD1D2 in two opposite orientations. Importantly, in the canonical interaction where IpaA VBS1 and VBS2 interact with the HVD1 first and second bundle, respectively, IpaA VBS3 was found to interact with the first bundle of D2. These results are consistent with the solid phase and native gel assays' results, indicating the unveiling of binding sites on the HVD2 domain.

TABLE 1

Cross-linked residues of the interactions between vinculin and IpaA domains.

| HVD1D2 with IpaA A483/A524 | | | | HVD1 with IpaA A483/A524 | | | |
|---|---|---|---|---|---|---|---|
| HVD1D2:A483 | | HVD1D2:A524 | | HVD1:A483 | | HVD1:A524 | |
| HVD1D2 | A483 | HVD1D2 | A524 | HVD1 | A483 | HVD1 | A524 |
| E31 | K150 | E200 | K109 | E60 | G-5 | E200 | K17 |
| E200 | K143 | E31 | K109 | D67 | G-5 | E60 | K18 |
| E128 | K135 | E200 | K102 | E128 | G-5 | E200 | K56 |
| K464 | D112 | E128 | K94 | E200 | G-5 | K170 | K71 |
| K170 | D112 | K170 | D81 | E240 | K16 | K170 | D72 |
| K352 | E108 | E66 | K77 | E66 | K31 | D67 | K77 |
| K170 | E108 | K366 | D75 | D67 | K31 | K170 | D81 |
| E100 | K97 | K173 | D75 | E235 | K31 | K173 | D81 |
| E66 | K97 | K464 | E67 | E240 | K31 | E200 | K94 |
| E200 | K89 | E66 | K60 | E66 | K58 | E240 | K102 |
| E66 | K80 | E200 | K56 | E31 | K60 | E200 | K105 |
| E60 | K80 | E66 | K56 | E200 | K60 | D39 | K109 |
| K59 | D79 | E60 | K39 | E200 | K80 | E31 | K109 |
| K170 | D76 | K173 | D35 | E200 | K89 | E28 | K109 |
| K219 | E72 | K170 | E31 | E200 | K97 | | |
| K170 | E72 | E128 | K19 | G1 | E108 | | |
| E66 | K60 | E128 | K17 | K170 | D112 | | |
| E66 | K58 | E66 | K7 | K170 | D113 | | |
| E66 | K48 | | | D67 | K118 | | |
| E128 | K44 | | | E128 | K135 | | |
| E66 | K44 | | | E200 | K143 | | |
| E66 | K31 | | | | | | |
| E66 | K16 | | | | | | |

TABLE 1-continued

Cross-linked residues of the interactions between vinculin and IpaA domains.

| HVD1D2 with IpaA A483/A524 | | | | HVD1 with IpaA A483/A524 | | | |
|---|---|---|---|---|---|---|---|
| HVD1D2:A483 | | HVD1D2:A524 | | HVD1:A483 | | HVD1:A524 | |
| HVD1D2 | A483 | HVD1D2 | A524 | HVD1 | A483 | HVD1 | A524 |
| K366 | D2 | | | | | | |
| D389 | G-5 | | | | | | |
| D361 | G-5 | | | | | | |
| E181 | G-5 | | | | | | |
| D176 | G-5 | | | | | | |
| D121 | G-5 | | | | | | |
| D67 | G-5 | | | | | | |
| E60 | G-5 | | | | | | |

Vinculin is involved in cell proliferation, migration, as well as in adhesive processes with the extracellular matrix and at cell-cell junctions. The A483-mediated unveiling of sites on the vinculin D2 domain is expected to promote strong effects on these vinculin-dependent processes. Consistently, when cells were transfected with GFP-A483, large vinculin-rich peripheral and ventral focal adhesions (FA) could be detected, that were not present in control cells (FIG. 4A-B). An increase in the cell surface was also observed in GFP-A483 transfected cells, which showed a median surface of 1846.9 655 $\mu m^2$ as opposed to 1156.2±767 $\mu m^2$ for GFP control cells, indicative of the higher adhesive properties of GFP-A483 transfectants (FIG. 4F, FIG. 7A-B).

To test the effects of GFP-A483 on dynamic processes, cells were FACS-sorted following transfection and analyzed by time-lapse videomicroscopy and the time between two division events was determined. The density profile of division times for GFP-transfected cells showed a gamma distribution, with a median time of 10.2 1.45 hours (FIG. 4C and FIG. 7D; 93 cells, N=4). In contrast, the density profile of the GFP-A483 population showed two distinct groups, one with a median time of not statistically different than that of control cells (30 cells, N=4), and another considerably longer of 17.1±1.6 hours (10 cells, N=4) (FIG. 7C-D).

The median velocity of migration was also decreased in GFP-A483 transfected cells compared to GFP-transfected controls, with median values corresponding to 30.7±6.48 $\mu m$/hour (199 cells, N=4) compared to 35.1±7.51 $\mu m$/hour (268 cells, N=4), respectively (FIG. 4D). The decreased median velocity was also associated with a decrease in the total explored area, with a rate of the root square of the Median Square of Displacement of 300097 2668 $\mu m \cdot hr$ ($R^2$=0.98) for GFP-A483 transfected cells, and 355998+ 3447 $\mu m \cdot hr$ ($R^2$=0.97) for GFP transfected controls (FIG. 4E).

Figure 22:
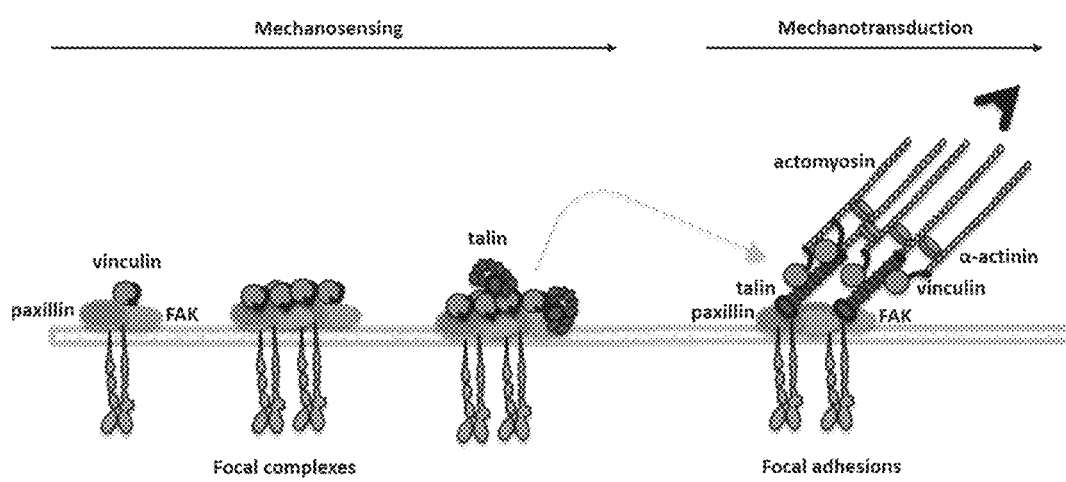
FIG. 22 is a set of schemes depicting a model for the roles of talin and vinculin in mechanosensing and mechanotransduction during integrin-mediated cell adhesion. In a first step of mechanosensing (left panel), myosin II-mediated cytoskeletal tension promotes the FAK-mediated phosphorylation of paxillin, and subsequent association of phosphorylated paxillin with vinculin. Signaling linked to this complex in response to mechanosensing leads to the recruitment of talin, under its folded form. In a second step of mechanotransduction (right panel), each vinculin molecule contributes to tethering a talin VBS with F-actin, strengthening cytoskeletal linkage therefore enabling higher traction forces.

Cell adhesion is subjected to mechanosensing, acto-myosin dependent stretching of talin exposing its VBSs being a key step in vinculin scaffolding (del Rio et al., 2009. Science. 323:638-41; Yao et al., 2014. Sci. Rep. 4:4610) (FIG. 22). We wanted to test whether A483-mediated vinculin supra-activation favored the kinetics of cell adhesion, because of the "wider opening" of vinculin. For this, transfected cells were resuspended by trypsinization and plated for defined periods on fibronectin-coated surfaces. Strikingly, the formation of large adhesion structures could be detected in GFP-A483 transfected cells as early as 7 minutes following plating, at a time where no adhesion structures was observed for GFP-transfected cells (FIG. 7E). When cell adhesion was quantified as a function of time following plating, a considerable difference was evidenced in GFP- A483 transfected cells, which show significant levels of adhesion as early as 7 minutes following plating (FIG. 4G-H and FIG. 7F). These results suggested that GFP-A483 transfected could perform strong adhesion in the absence of mechanosensing. To further confirm this, the cell resistance to shear stress was measured as a function of plating time, using a microfluidic chamber device. Consistent with dynamic adhesion assays and as opposed to control cells, most of GFP-A483 transected cells resisted a shear stress up to 2.5 dynes/cm$^2$, when allowed to spread onto the fibronectin coated surfaces for as little as 1 minute compared to control GFP transfected cells (FIG. 4I).

Figure 12:
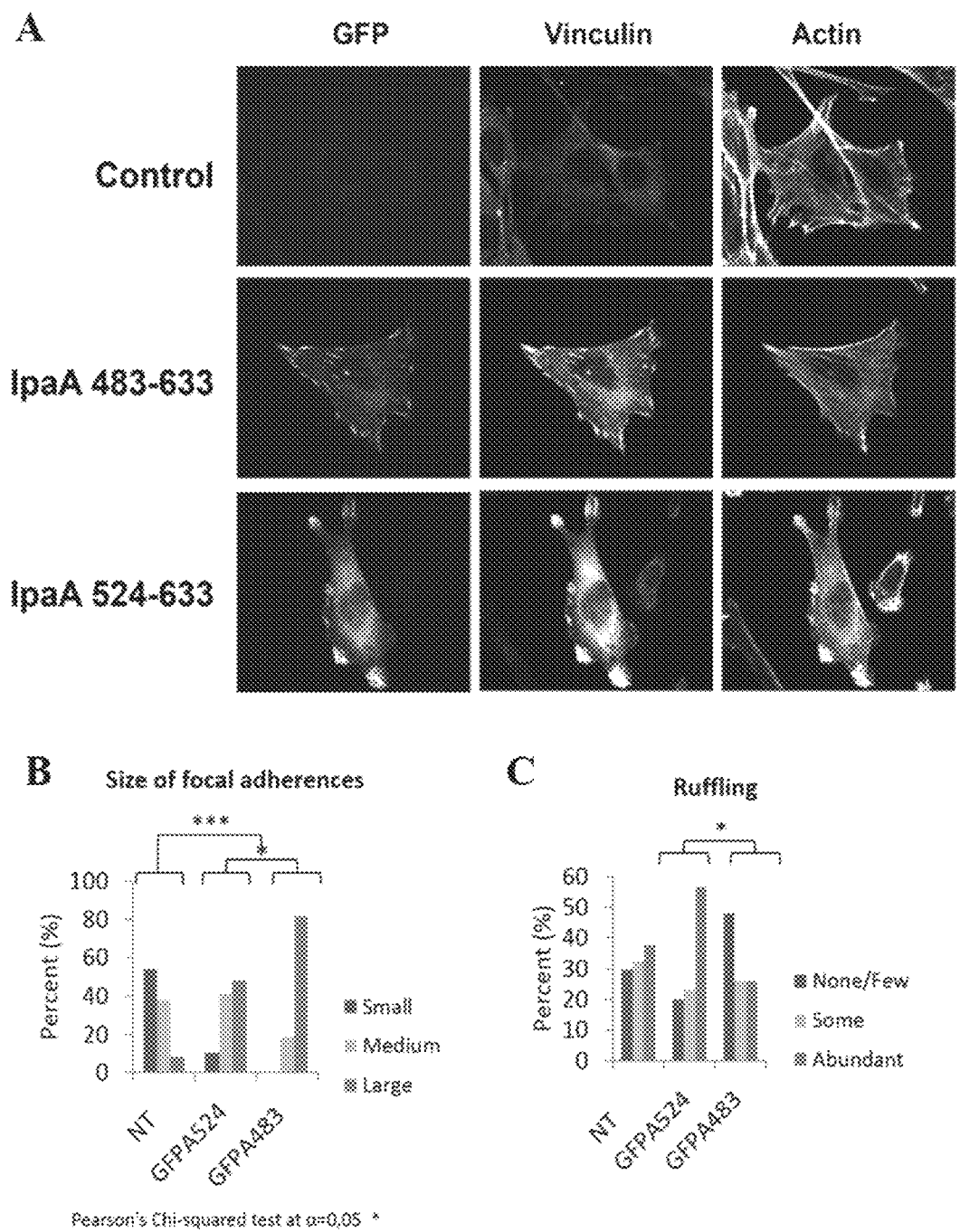
FIG. 12 is a set of photographs and graphs showing that IpaA A483 enhances vinculin-mediated cell adhesion compared A524 without inducing membrane ruffling. A, B, and C, Immunofluorescence analysis of C2.7 cells (Control), GFP-A483 transfectants (IpaA 483-633) and GFP-A524 transfectants (IpaA 524-633). GFP fluorescence as indicated (IpaA); vinculin as indicated; actin as indicated. B, and C, cells plated for 16 hours. B, The percentage of cells showing FAs with a small (Small), medium (Medium) and large (Large) FAs was scored. The results are representative of ncontrol=37, nGFP-A483=27 cells and nGFP-A524=29 in 3 independent experiments. Distributions were compared using a Pearson's Chi-squared test. C, The percentage of cells showing few (None/Few), some (Some) and abundant (Abundant) membrane ruffling was scored. The results are representative of n(control)=37, n(GFP-A483)=27 cells and n(GFP-A524)=30 in 3 independent experiments. Distributions were compared using a Pearson's Chi-squared test.

Together, these results indicate that the supra-activation of vinculin by A483 requires the presence of the three VBS (VBS1, VBS2 and VBS3), since it is not observed with A524 (containing only VBS1 and VBS2, FIG. 12). A483-mediated supra-activation results in the formation of large and highly stable focal adhesions that are not observed with A524, and not only reinforces, but also accelerates the dynamics cell adhesion.

Example 2: The *Shigella* Type III Effector IpaA Promotes Vinculin-Talin Scaffolds Through a Unique Hybrid Binding Site The *Shigella* Type III Effector IpaA Interacts with the Focal Adhesion Protein Talin Via its VBS3.

We used a yeast two-hybrid approach to identify molecular partners of the *Shigella* effector IpaA. The screen used an established human placental cDNA library totaling 82.02 million prey clones and a construct containing amino acid residues 1 to 565 of IpaA (SEQ ID NO: 1), devoid of the VBS1 and 2 sites (559-633) as bait. This screen identified 150 clones representing 16 different genes. Among these genes, 2 were with very high confidence in the interaction, which include "talin" identified in 95 prey clones corresponding to different in-frame regions of talin VBS1 (482-636) (SEQ ID NO: 38) and VBS3 (1944-1969) (SEQ ID NO: 39) previously identified as bona fide VBSs. As expected, because of the presence of IpaA VBS3 in the IpaA(1-565) bait, vinculin was also identified albeit with a lesser confidence than talin.

To confirm and extend these results, IpaA derivatives tagged with the V5 epitope were constructed and tested for their ability to associate with talin following their transfection and cellular expression (FIG. 8A). As shown in FIG. 8B, IpaA 7-522 localized to focal adhesions and other talin-containing structures. In contrast, IpaA 7-422, in which the IpaA VBS3 was deleted, showed a diffuse staining and did not co-localize with talin, indicating that the IpaA VBS3 was required for talin association (FIG. 8B).

To directly show that IpaA VBS3 acted as a Talin Binding Site (TBS), we performed native protein gel shift assays using purified synthetic IpaA VBSs. IpaA VBS3 promoted the dose-dependent formation of talin H1-H4:IpaA VBS3/TBS complexes that could be detected at an IpaA VBS3 concentration of 25 µM. In contrast, even at high concentrations, IpaA VBS1 and IpaA VBS2 did not induce the formation of such talin H1-H4 complexes (FIG. 8C).

Together, these results indicate that IpaA VBS3 also act as a TBS, a property that is not shared by the IpaA VBS 1 and IpaA VBS2.

IpaA VBS3/TBS Binds to Talin H1-H4 in the Presence of paA VBS1-2.

The three IpaA VBSs are closely spaced within the carboxy-terminal 145 residues of IpaA, A483 (FIG. 8A). To test whether IpaA VBS3/TBS binding to talin H1-H4 could still occur in the presence of IpaA VBS1/2, we performed native gel shift assays with A483. As shown in FIG. 9C, a clear migration shift could be detected with A483 at concentrations as low as 5 µM, when mixed with talin H1-H4 (FIG. 9C, arrow), that was accompanied by a depletion of the species corresponding to talin H1-H4 alone consistent with the formation of an A483:talin H1-H4 complex (FIG. 9C, left). When A524, containing only IpaA VBS1/2 but not IpaA VBS3/TBS was incubated with talin H1-H4, no migration shift could be detected (FIG. 9C, right).

Then, we further characterized the interaction of IpaA VBSs with talin H1-H4 by isothermal titration calorimetry (ITC).

Figure 9A:
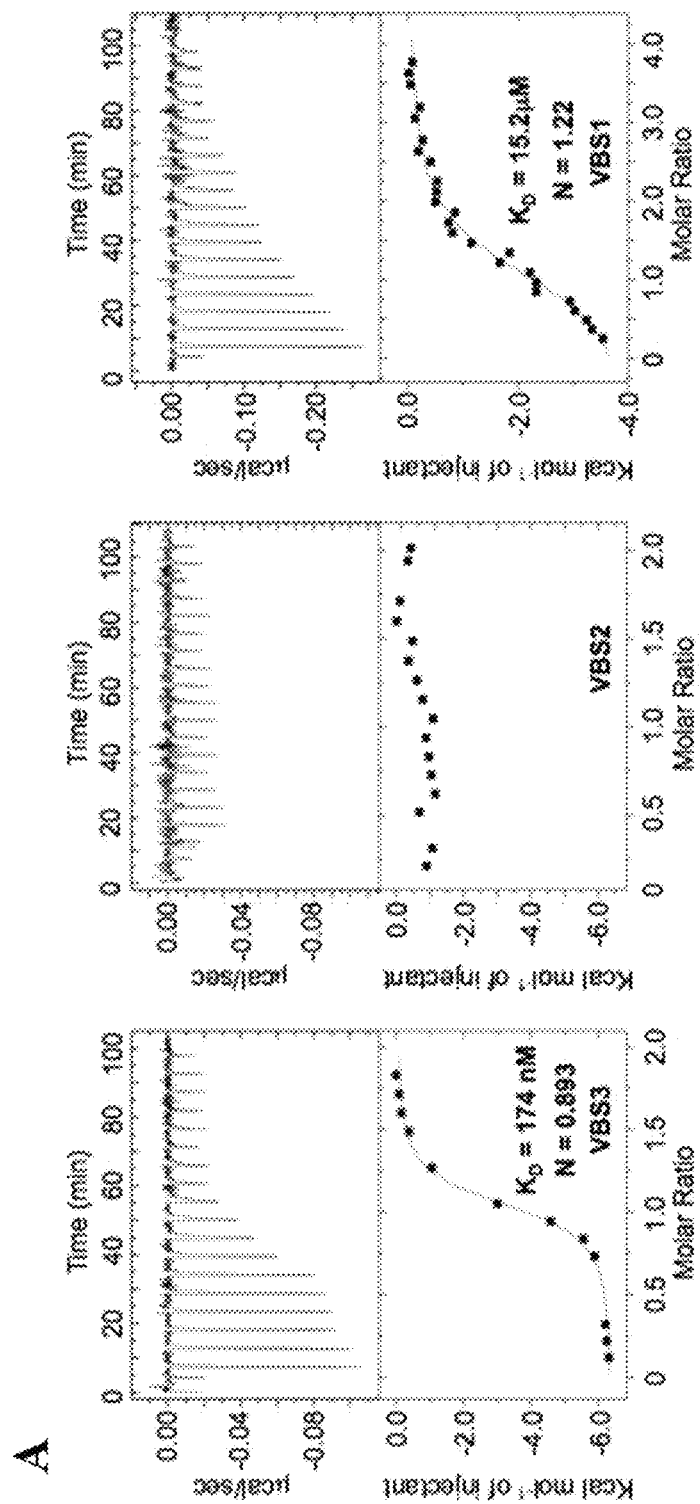
FIG. 9 is a set of photographs and graphs showing the binding of IpaA VBS3 to talin with high affinity. A, Isothermal titration calorimetry (ITC) analysis of the interaction between talin H1-H4 and the indicated IpaA VBSs. The estimated Kr are 15.17 µM and 174 nM for IpaA VBS1 and IpaA VBS3, respectively. B, ITC analysis of the interaction between the A483:HVD1 complex and talin H1-H4, $K_D$=2.94 µM. C, Native PAGE analysis of A483 and A524 interaction with talin H1-H4. Purified talin H1-H4 was incubated with A483 or A524 at the indicated talin H1-H4: IpaA derivative molar ratio, with 1 corresponding to a final concentration of 25 µM.

Consistent with native gel shift assays, ITC measurements indicated that IpaA VBS3/TBS bound to talin H1-H4 with a high affinity ($K_D$=174±19 nM), whereas IpaA VBS2 did not show any interaction with talin H1-H4 (FIG. 9A). IpaA VBS3/TBS interaction with talin H1-H4 was exothermic, with a predominant enthalpic contribution ($\Delta H_{VBS3}$=−6393 cal/mol) and a significant entropic contribution (−T$\Delta S_{VBS3}$=−2826 cal/mol) (Table 2). However, in contrast to native gel assays, IpaA VBS1 was found to interact with talin H1-H4, although with much lower affinity than IpaA VBS3/TBS ($K_D$=15.2±1.1 µM). When binding of A483 to talin H1-H4 was studied, A483:talin H1-H4 complex formation could also be detected, with an estimated affinity ($K_D$=24.9 6.8 nM), that was even higher than that of IpaA VBS3/TBS alone (Table 2, A483 (VBS3)).

TABLE 2

Non-linear fit values for ITC measurements.

| | Cell | | | | |
|---|---|---|---|---|---|
| | Talin H1-H4 | Talin H1-H4 | HVD1:A483 Titrant | A483 (VBS3) | A524 |
| | IpaA VBS1 | IpaA VBS3 | Talin H1-H4 | Talin H1-H4 | Talin H1-H4 |
| N | 1.22 | 0.893 | 0.459 | 1 | 1.5 |
| $K_D$ | 15.17 µM (±1.14) | 174.52 nM (±18.9) | 2.94 µM (±0.89) | 24.93 nM (±6.84) | 2.03 µM (±0.50) |
| ΔH (cal/mol) | −4104 | −6393 | −9047 (±1386) | −6229 (±103) | −3979 |
| −TΔS (cal/mol) | −2471 | −2826 | −1368.4815 | −3796 | −3469 |
| ΔG (cal/mol) | −6575 | −9219 | −7678.5185 | −10025 | −7448 |

N (stoichiometry),
$K_D$ (affinity constant),
ΔH (cal/mol) enthalpy,
−TΔS (cal/mol) entropic contribution and
ΔG (cal/mol) free enthalpy.
IpaA binding to talin H1-H4 is exothermic (ΔG < 0) and mainly driven by enthalpy (ΔH < 0 and ΔH < −TΔS).
Talin H1-H4 binding to IpaA peptides VBS1 and VBS2 shows an important enthalpic and minor entropic contribution.
Binding of talin H1-H4 to the A483:HVD1 1:1 complex is exclusively enthalpically-driven, with an entropic penalty (−TΔS > 0).

These results confirm that IpaA VBS3 can act as a bona fide TBS, and that IpaA VBS1 may cooperate with IpaA VBS3/TBS to promote binding to talin H1-H4.

IpaA VBS3/TBS Forms a New α-Helix Bundle with Talin H1-H4.

The crystal structure of talin H1-H4 domain in complex with IpaA VBS3/TBS peptide was determined to a 2.3 Å resolution (Table 3). The structure of the complex revealed a drastic conformational restructuration of talin H1-H4 when bound to IpaA VBS3/TBS, where the four α-helices of talin H1-H4 fold around IpaA VBS3/TBS. IpaA VBS3/TBS thus represent an entirely novel mode of interaction with talin H1-H4. Indeed, previous structural works reported that the binding of HVD1 (SEQ ID NO: 11) occurred on a loosely folded conformation of talin H1-H4, in which only the fourth α-helix (H4) of talin VBS1 interacts with the amino-terminal four α-helix bundle of HVD1 (SEQ ID NO: 11) (Papagrigoriou et al., 2004).

TABLE 3

X-ray data collection and crystallographic refinement statistics

X-ray data reduction

| | |
|---|---|
| Space group | P 2$_1$2$_1$2 |
| Unit cell dimensions | |
| a, b, c (Å) | 90.24, 53.12, 69.58 |
| α, β, γ (°) | 90, 90, 90 |
| Resolution (Å) | 90.26-2.31 (2.47-2.31)$^a$ |
| Total measured reflections | 55,338 |
| Unique reflections | 7,995 |
| R$_{merge}$ [%] | 4.5 (53.5)$^a$ |
| I/σ (I) | 35.7 (1.4)$^a$ |
| Completeness (%) | 99.3 (99.8)$^a$ |
| Redundancy | 7.0 (3.1)$^a$ |

Crystallographic refinement

| | |
|---|---|
| Resolution (Å) | 20.7-2.31 (2.47-2.31)$^a$ |
| Number of reflections | 15,199 (2,697) |
| R$_{work}$/R$_{free}$$^b$ | 26.0/31.0 (27.7/30.1)$^a$ |
| Number of atoms | |
| Protein | 2,338 |
| Solvent | 71 |
| R.m.s. deviations from ideal geometry | |
| Bond lengths (Å) | 0.01 |
| Bond angles (°) | 1.24 |

$^a$Values in parentheses are for the highest resolution shell.
$^b$R$_{free}$ was calculated as R$_{work}$ using 4.9% of reflections that were selected randomly and omitted from refinement.

The compact folding of the complex formed by talin H1-H4 and IpaA VBS3/TBS was reminiscent of the inactive talin VBS1 t(H1-H5), whereby the hydrophobic H4 α-helix is buried in the presence of the H5 α-helix. When structurally aligned, an important homology between the talin H1-H4:IpaA VBS3/TBS complex and t(H1-H5) could be observed.

This structural similarity occurred in spite of the absence of obvious conservation between the residues of IpaA VBS3/TBS and the talin VBS1 H5 helix, suggesting that IpaA VBS3/TBS and talin H5 share punctual key stabilizing contacts with the talin H1-H4 helixes.

These findings indicate that IpaA VBS3/TBS acts as a TBS which folds talin H1-H4 into a compact structure, homologous to inactive tVBS1.

The asymmetric unit comprised two talin H1-H4:IpaA VBS3/TBS complexes and the electron density was well resolved overall, except for the loop regions (amino acid residues from 518 to 526) connecting the α-helices H1 and H2 in both molecules, indicating that these regions were dynamic. The two talin H1-H4:IpaA VBS3/TBS complexes in the asymmetric unit form a dimer via a disulfide bridge provided by talin Cys575 from each talin subunit. IpaA VBS3/TBS is nested in a groove between α-helices H2 and H4 of talin H1-H4 via hydrophobic and hydrogen bonding interactions. Specifically, the side chains of residues Val499, Leu506 and Leu509 of IpaA VBS3/TBS pack against Thr554, Val558, Leu622, Val547, Ile550. Leu615, Met587, Val591, Leu608, and Ala612 of talin H1-H4. Furthermore, the side chains of Ser502 and Asn505 engage in hydrogen bonding interactions with the side chain of Thr554 and the backbone carbonyl of Gly614, respectively.

Superposition of IpaA VBS3/TBS in its talin bound state onto its vinculin bound state reveals that the interaction of IpaA with talin α-helix H4 is unique to IpaA binding to talin and not engaged in interactions in its vinculin bound state, while the interaction of IpaA with vinculin α-helix a1 is unique to IpaA binding to vinculin and not interacting in its talin bound state. However, superposition of talin H1-H4 in its IpaA bound state onto talin H1-H5 revealed a remarkable molecular mimicry although there is no obvious conservation between IpaA VB3/TBS and the talin H5 helix.

IpaA483 Mediates the Folding of Talin H1-H4 Through IpaA VBS3.

The compact folding of IpaA VBS3/TBS:talin H1-H4 represents a novel mode of TBS-talin interaction that limits steric hindrance, and would be potentially compatible with the establishment of other interactions with IpaA VBS1/2. To test if talin H1-H4 folding could be triggered by A483, we performed size-exclusion chromatography (SEC, FIG. 10). The formation of the protein complexes was observed by comparing the elution profiles of protein mixtures versus the proteins alone.

The hydrodynamic radius (R$_H$) of A483 and talin H1-H4 were measured and normalized to R$_G$, the estimated hydrodynamic radius of globular proteins with the same MW (Table 4). The R$_H$/R$_G$ ratio showed that A483 and A524 alone are both loosely folded, with values of 1.83, 1.88, respectively.

TABLE 4

The formation of a tripartite A483:talin H1-H4:HVD1 complex is associated with an important conformational refolding. The estimated hydrodynamic radius Radius$_m$ and the ratio (Radius$_m$/Radius$_g$) between this measured value and the hydrodynamic radius of a globular protein with the same MW (Radius$_g$) are indicated.

| Stoichiometry | Protein | MW (Da) | Radius$_m$ (Ang) | Radius$_g$ (Ang) | Radius$_m$/Radius$_g$ |
|---|---|---|---|---|---|
| | A483 | 17304 | 32.86 | 17.99 | 1.83 |
| | A524 | 12762 | 28.93 | 15.36 | 1.88 |
| | HVD1 | 31069 | 28.25 | 24.36 | 1.16 |
| 1:1 | TlnH1-H4 | 18344 | 33.33 | 18.54 | 1.80 |
| 1:1 | TlnH4:A483 | 35648 | 35.78 | 26.15 | 1.37 |
| 1:1 | TlnH4:A524 | 31106 | 33.33 | 24.37 | 1.37 |
| 1:1 | TlnH4:HVD1 | 49413 | 35.78 | 30.97 | 1.16 |
| 1:1 | HVD1:A483 | 48373 | 40.27 | 30.63 | 1.31 |
| 1:1 | HVD1:A524 | 43831 | 38.41 | 29.11 | 1.32 |
| 1:1:1 | HVD1:A483:TlnH4 | 66717 | 40.27 | 36.18 | 1.11 |
| 1:1:1 | HVD1:A524:TlnH4 | 62175 | 36.64 | 34.88 | NC |

Figure 10:
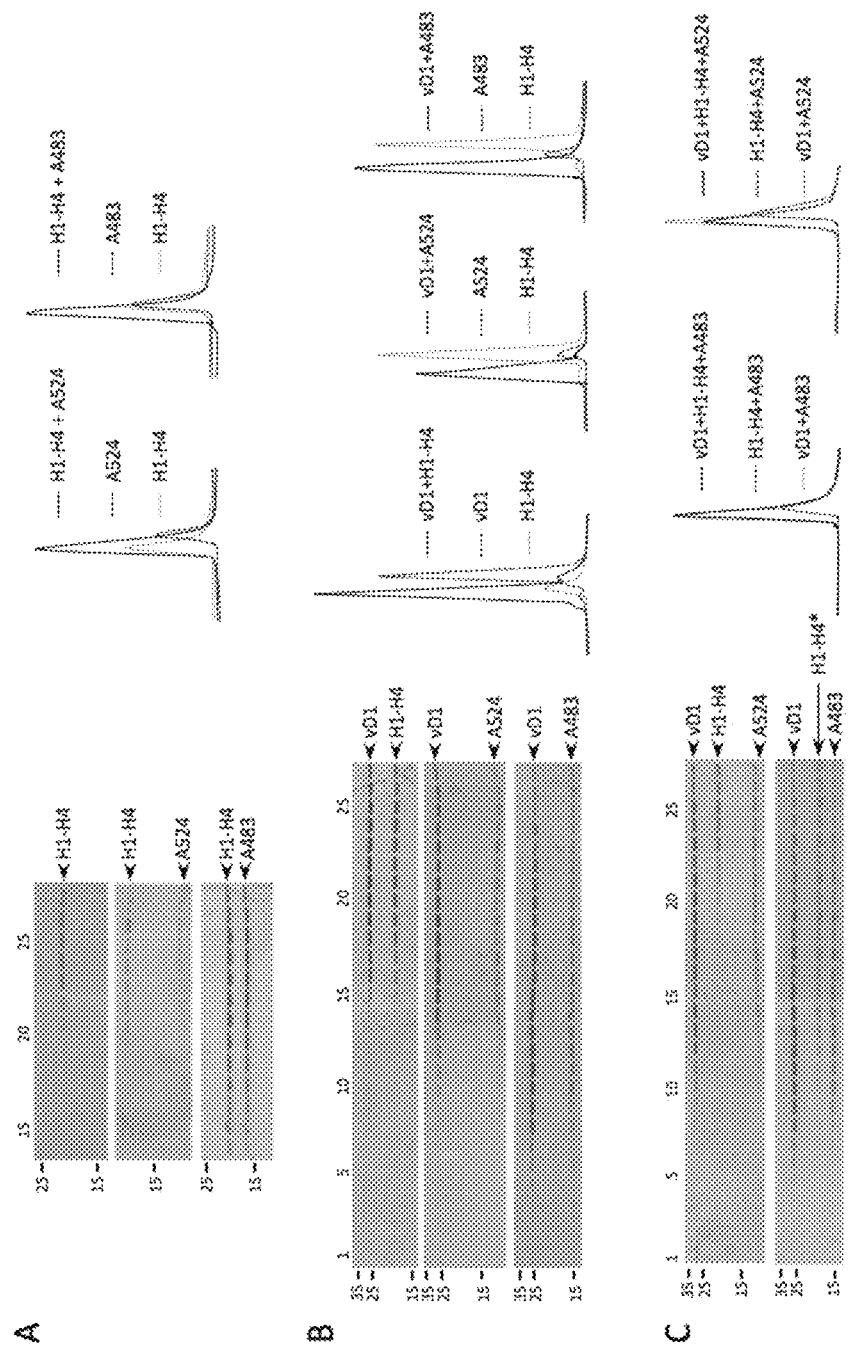
FIG. 10 is a set of photographs and graphs showing A483 ternary complex with HVD1 and talin H1-H4. Size exclusion chromatography (SEC) analysis of interaction between IpaA derivatives, talin H1-H4 and HVD1. Proteins indicated on the left were incubated for 60 minutes in column buffer prior to SEC analysis using a Superdex 75 column. Eluted fractions annotated above each lane were analyzed by SDS-PAGE using a 12.5% polyacrylamide gel and Coomassie blue staining. SEC analysis of A, Talin H1-H4 (top panel), talin H1-H4 and A524 (middle panel), talin H1-H4 and A483 (bottom panel); B, HVD1 and talin H1-H4 (top panel), HVD1 and A524 (middle panel), HVD1 and A483 (bottom panel); C, HVD1 and talin H1-H4 and A524 (top panel), HVD1 and talin H1-H4 and A483 (bottom panel). The traces represent the densitometry analysis of the indicated protein/protein complex species.

Consistent with previous reports, talin H1-H4 was also loosely folded with a R$_H$/R$_G$ ratio equal to 1.80 (Table 4; Papagrigoriou et al. 2004). In contrast, and as expected from previous reports, the R$_H$/R$_G$ ratio of the D1 domain of vinculin (HVD1) (SEQ ID NO: 11) corresponds to a tightly folded globular protein (Borgon et al., 2004). When incubated with talin H1-H4, however, the formation of 1:1 A483:talin H1-H4 as well as A524:talin H1-H4 could be detected. The formation of these complexes led to a substantial refolding of both proteins, since the R$_H$/R$_G$ ratio switched from 1.80 and 1.83 for A483 and talin H1-H4 alone, respectively, to 1.37 for the A483:talin H1-H4 complex (FIG. 10 and Table 4).

Binding of Talin to IpaA VBS3/TBS.

Further investigation regarding the interaction between talin and IpaA were performed.

Figure 13:
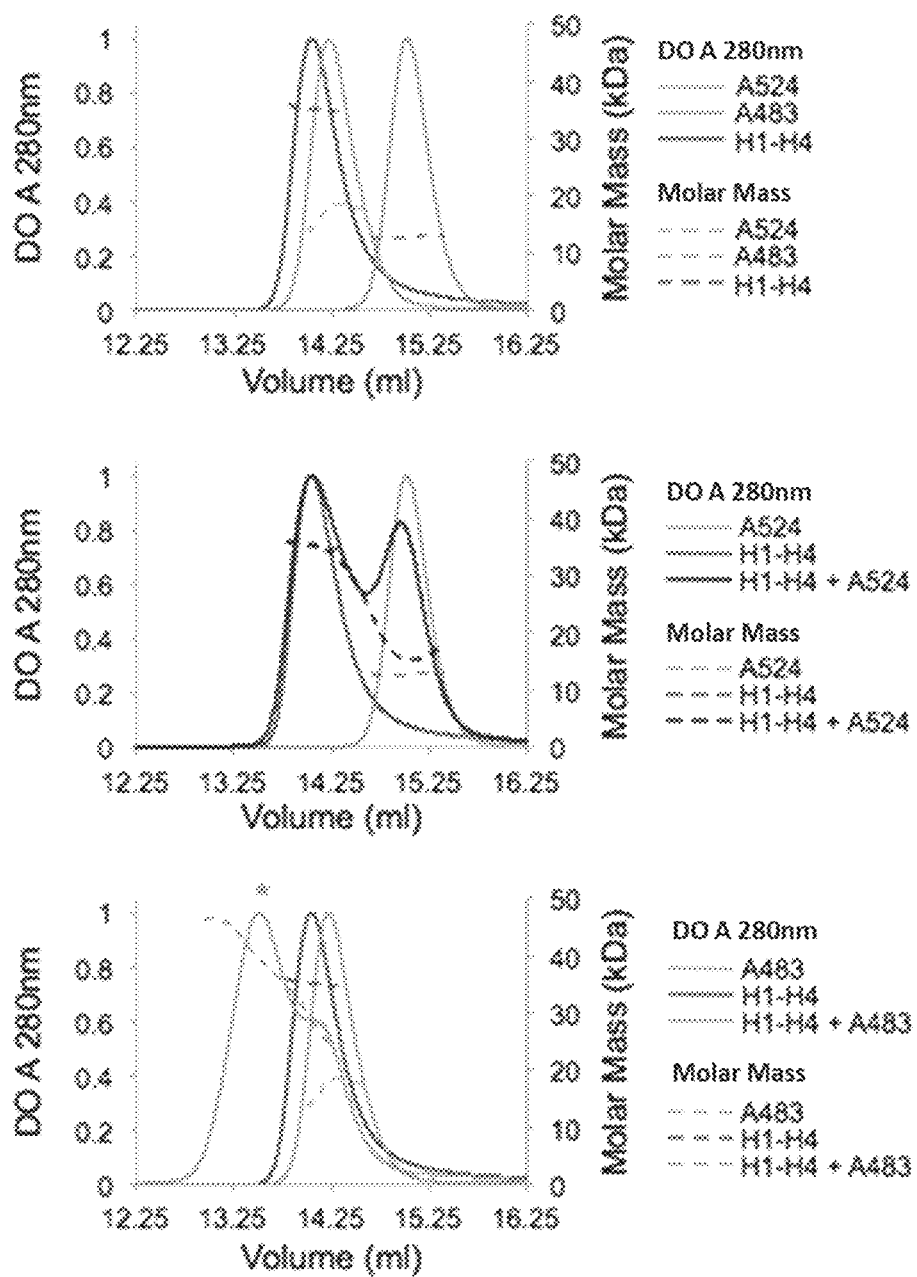
FIG. 13 is a set of graphs showing that IpaA VBS3 promotes binding of the IpaA carboxyterminal domain to talin H1-H4. Size exclusion chromatography-multi angle light scattering (SEC-MALS) analysis of interaction between IpaA derivatives and talin H1-H4. Indicated proteins were incubated for 60 minutes in column buffer prior to SEC analysis using a Superdex 200 10/300 GL Increase column. Traces: absorbance at 280 nm of the indicated proteins or complex species. Dotted lines: molecular mass of the indicated proteins or complexes determined by MALS.
Figure 14:
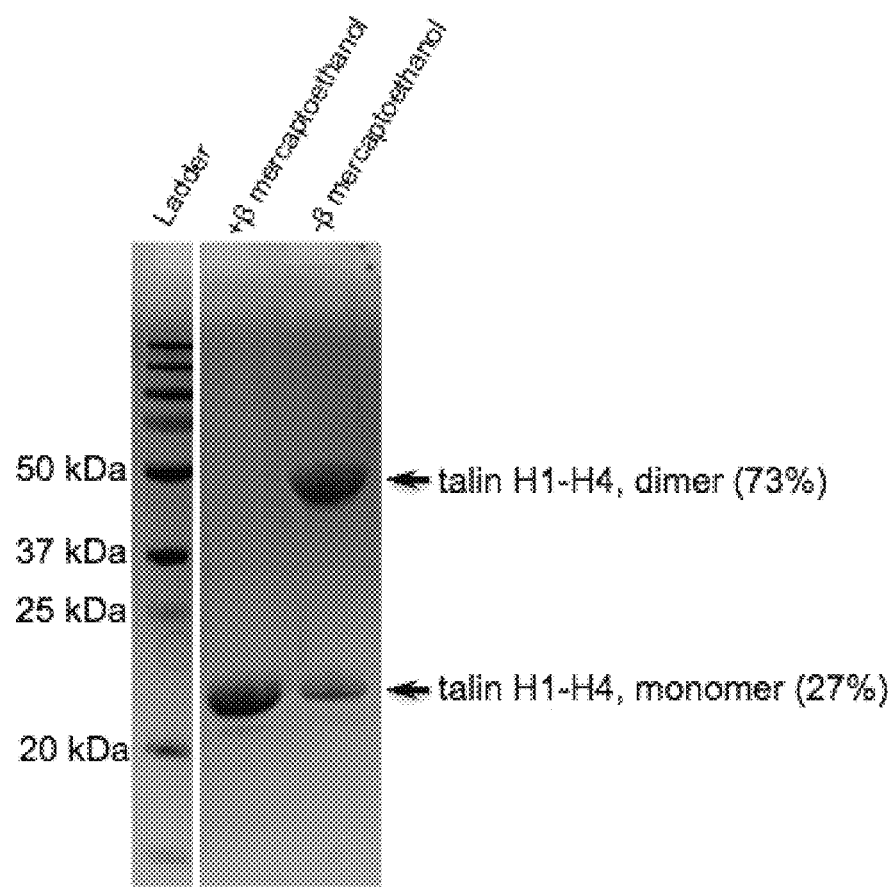
FIG. 14 is an image representing talin H1-H4 forms a covalent dimer in solution. SDS-PAGE (12.5%) electrophoresis analysis of a solution containing 20 μm of purified talin H1-H4 protein denatured in the presence (left) or in the absence (right) of a reducing agent (1 mM ß-Mercaptoethanol). The percentages of talin H1-H4 dimer and monomer were quantified by densitometry.

To study the interaction of talin H1-H4 with IpaA A483 and A524 in solution, samples were analyzed by size-exclusion chromatography coupled with multi-angle static light scattering system (SEC-MALS, FIG. 13). Both IpaA derivatives A483 and A524 were monomers in solution, as indicated by the molecular mass determination by MALS (FIG. 13 and Table 5). Consistent with the structure resolution, SEC-MALS analysis indicated that talin H1-H4 formed a globular dimer in solution (FIG. 13 and Table 5), resulting from the covalent linking of two talin H1-H4 molecules by disulfide bridging (FIG. 14). When mixed, single species corresponding to the talin H1-H4 dimer and A524 monomers were still recovered in the SEC-MALS analysis, consistent with the absence of complex formation (FIG. 13). In contrast, a compact globular complex corresponding to one talin H1-H4 dimer bound to one A483 molecule was observed (FIG. 13 [H1-H4+A483] and Table 5). These results are in agreement with IpaA VBS3/TBS binding to talin H1-H4 (FIG. 9 and Table 4).

TABLE 5

SEC-MALS analysis of the interaction between talin H1-H4 and IpaA proteins. The molecular mass predicted by the primary sequence (Predicted MM) of talin H1-H4 and IpaA proteins and complex was compared and the measured molecular mass (Measured MM) of these proteins and complexes by SEC-MALS in the indicated stoichiometries. The hydrodynamic radius ($R_g$) of the complex was determined by refractometry.

|  | Stoichiometry | Predicted MM (kDa) | Measured MM (kDa) | $R_g$ (nm) |
| --- | --- | --- | --- | --- |
| A483 | 1 | 17.3 | 17.9 | n.d. |
| A524 | 1 | 12.8 | 12.5 ± 0.7 | n.d. |
| Talin H1-H4 | 2 | 36.4 | 35.2 ± 0.2 | 3.3 ± 0.3 |
| Talin H1-H4 + A483 | 2:1 | 53.7 | 46.8 ± 0.2 | 3.7 ± 0.3 |

Figure 15:
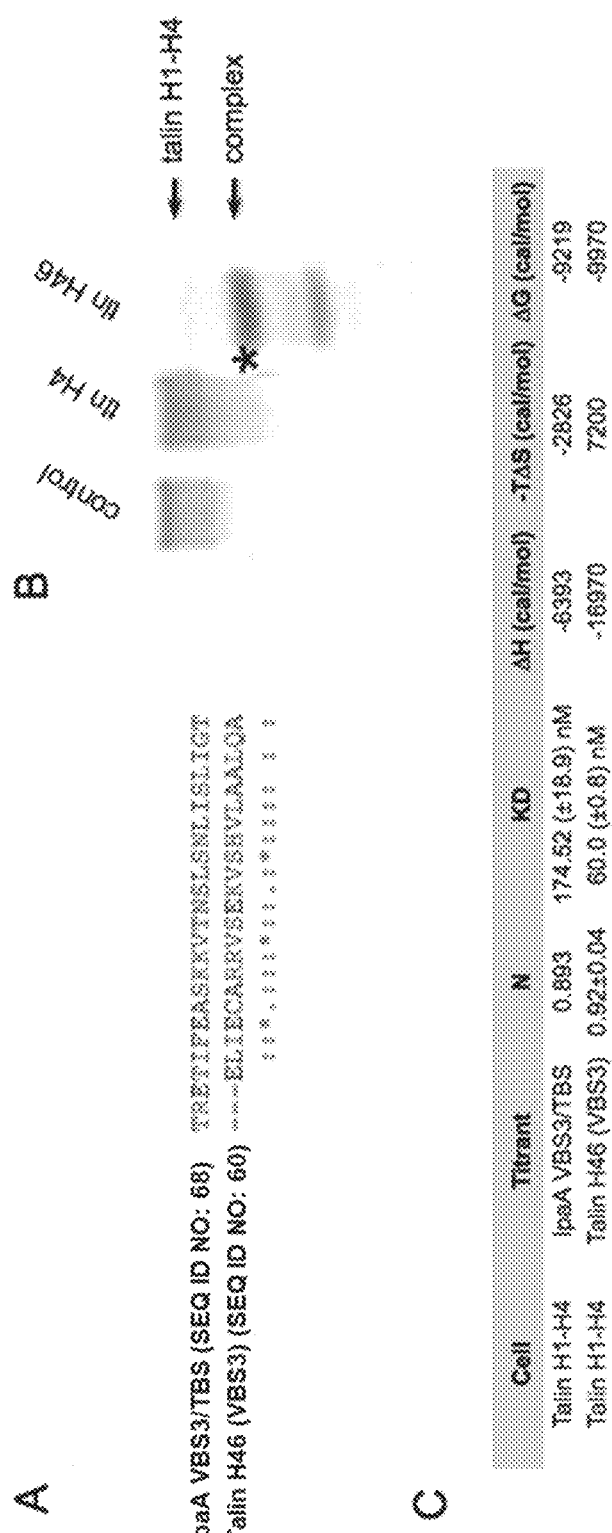
FIG. 15 is a set of scheme, image and table showing that talin H46 (VBS3) α-helix (SEQ ID NO: 60) is an hybrid VBS/TBS in vitro. A, Sequence alignment of IpaA VBS3/TBS and endogenous talin H46 (VBS3) α-helix by Clustal W (1.83) multiple sequence alignment. B, Talin-VBSs binding to the 4-helix bundle of talin. Native gel analysis showing binding of talin VBS3 to the talin 4-helix bundle H1-H4. Control: talin H1-H4 alone; tln H4: talin H1-H4: talin H4; tln H46: talin H1-H4:talin H46. The asterisks indicate complex formation. C, Isothermal titration calorimetry (ITC) analysis of the interaction between talin H1-H4 and talin H46 (VBS3) or IpaA VBS3 α-helixes. The estimated $K_D$ are 60 and 174.2 nM for talin H46 (VBS3) and IpaA VBS3/TBS, respectively.

We then tested whether the property of IpaA VBS3/TBS to bind vinculin and talin was unique, or if it was shared by "physiological" VBSs. By comparing the sequence of IpaA VBS3/TBS with the talin VBSs, we found a remarkable homology between IpaA VBS3/TBS and the 46th α-helix of the talin rod domain corresponding to talin VBS3 (H46, FIG. 15A). To test the capacity of talin H46 to interact with talin H1-H4, we performed native gel assays. As shown in FIG. 15B, talin H46, but not talin H4, formed a complex with talin H1-H4 (FIG. 15B, tln H46). These results were confirmed by ITC measurements, showing a high affinity interaction between talin H46 and talin H1-H4 with an estimated $K_D$=60+0.8 nM. Binding of talin H46 to talin H1-H4 was exothermic with a predominant enthalpic contribution (ΔH=−16970 cal/mol) and an unfavorable (−TΔS=+7200 cal/mol) entropic contribution (FIG. 15C). Interestingly, the affinity of talin H46 and IpaA VBS3/TBS for talin H1-H4 were comparable ($K_D$=60±0.8 nM and 174.52±18.9 nM, respectively; FIG. 9), further suggesting that these talin H46 could also act as a TBS.

These results indicate that a subclass of VBSs including IpaA VBS3/TBS and talin H46, but not talin VBS1 or IpaA VBS2, act as hybrid VBS/TBSs.

To test the capacity of IpaA VBS3/TBS to act as a TBS and a VBS in vivo, we analyzed the localization of a GFP-IpaA VB3/TBS fusion respective to that of talin and vinculin. GFP-IpaA VBS3/TBS predominantly labeled peripheral focal adhesion (FA) structures as indicated by its strict co-localization with talin and vinculin. Consistent with its binding to active configurations of talin, GFP-VBS3/TBS preferentially labeled FA structures, even in cells showing a large fraction of cytosolic talin.

Figure 16:
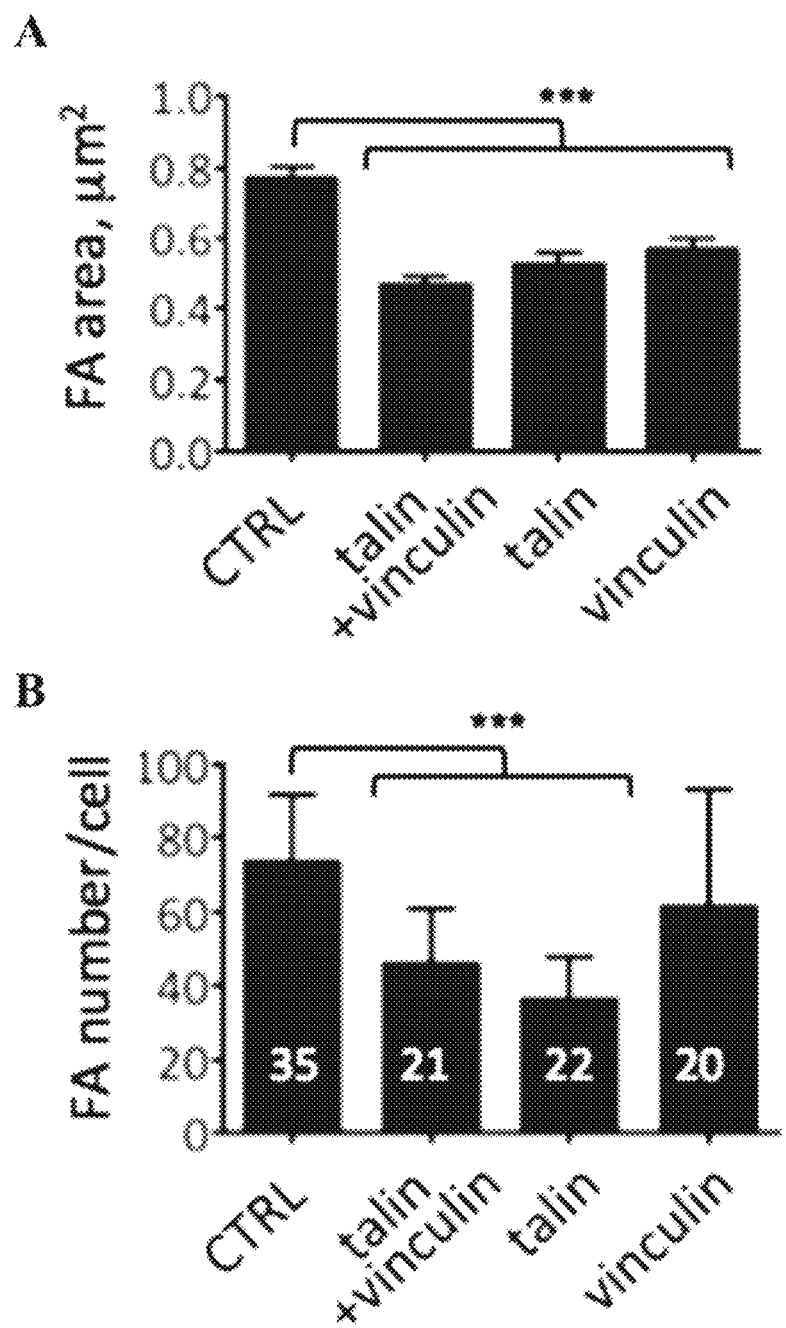
FIG. 16 is a set of graphs showing that IpaA VBS3/TBS targets vinculin- and talin-adhesion structures. HeLa cells were transfected with GFP-IpaA VBS3 and vinculin talin. Cells were fixed and processed for fluorescence staining of actin. Cells were treated with anti-vinculin or anti-talin siRNA prior to transfection with GFP-IpaA VBS3. Representative micrographs corresponding to a basal confocal plane are shown. Scale bar=5 μm. The area of focal adhesions (A, n>1000, N=2) and the number of focal adhesions per cell (B, n as indicated, N=2) were quantified using a semi-automated protocol in ICY. Geometric mean±95% confidence intervals of measurements are shown. One-way Anova test (p-value<0.001, ***).

We then tested the respective roles of vinculin and talin in the localization of GFP-IpaA VBS3/TBS. Cells were depleted for against talin and vinculin using siRNAs, and the recruitment of GFP-IpaA VBS3/TBS at adhesion structures was analyzed. Western blot analysis showed that in these experiments, the expression of vinculin and talin was depressed by at least 80%. Vinculin depletion led to a reduction in the median size of talin-labeled FAs by 28% relative to control cells. In these vinculin-depleted cells, IpaA VBS3/TBS co-localized with these talin-labeled structures confirming that it could act as a TBS. As expected, adhesion structures were more altered in talin-depleted cells, with a median size and numbers of adhesion structures reduced by 32% and 51%, respectively, relative to control cells (FIG. 16B). IpaA VBS3/TBS still co-localized in the vinculin-labeled structures in the talin-depleted cells, confirming its VBS function. A similar decrease was observed for cells depleted for vinculin and talin suggesting that IpaA VB3/TBS preferentially revealed talin-containing focal adhesions in these assays (FIG. 16A). Together, these results are consistent with IpaA VBS3/TBS acting as a hybrid site that binds to talin and vinculin.

A483 Form a Ternary Complex with Talin and Vinculin.

We next verified whether the compact folding of talin H1-H4 promoted by IpaA VBS3/TBS was compatible with binding of IpaA VBS1/2 to the vinculin D1 domain (HVD1) (SEQ ID NO: 11). As shown in FIG. 10C, following incubation of the three proteins prior to SEC analysis, the formation of a A483:HVD1:talin H1-H4 ternary complex could readily be detected from the co-elution of the proteins in early fractions compared to proteins alone or binary A483:HVD1 or A483:talin H1-H4 complexes (FIGS. 10B and 11A). Interestingly, this ternary complex eluted in the same volume as the A483:HVD1 binary complex alone (FIG. 10C, grey and black peaks) suggesting an additional folding upon A483 simultaneous binding to HVD1 (SEQ ID NO: 11) and talin H1-H4. The estimated $R_H/R_G$ ratio further decreased from 1.3 for the A483:HVD1 1:1 complex to 1.1 for the A483:HVD1:talin H1-H4 1:1:1 ternary complex.

The A483:HVD1:talin H1-H4 ternary complex formation was also analyzed by ITC. As shown in FIG. 9B and Table 2, the affinity of A483:HVD1 for talin H1-H4 was lower than that of the IpaA VBS3/TBS peptide alone, with an estimated Kr of 2.94 0.89 μM compared to 150 nM, respectively. This decreased affinity could be explained by decreased in exothermic free enthalpy for talin H1-H4 in the ternary complex from $\Delta G_{VBS3/TBS}$=−9070±103 cal/mol to $\Delta G_{ternary}$=−7678±1386 cal/mol, mostly due to a substantial decrease in the entropic contribution (−TΔS) from −1529 cal/mol for IpaA VBS3/TBS alone to +1368 cal/mol for A483:HVD1 (Table 2, HVD1:A483). This entropic penalty suggested a restrained motion of the ternary complex partially compensated by an increase in the ΔH enthalpy of talin H1-H4 binding (ΔH=−9047±1386 cal/mol). Such restrained motion could account for the two-fold decrease in the number of binding sites (N) observed for the ternary complex to 0.459+0.05. Alternatively, this decreased in N may result from competitive inhibition of HVD1 and talin H1-H4 binding to IpaA VBS3/TBS in A483.

These results confirm the unique property of IpaA VBS3 to act as a TBS, and show that its binding to talin H1-H4 is constraint but not impeded by the binding of the adjacent IpaA VBS1/2 to HVD1. Importantly, the formation of an A483:HVD1:talin H1-H4 tertiary complex, and the absence of stoichiometry other than 1:1 for the A483:HVD1 binary complex argue that in the context of IpaA, when IpaA VBS1/2 associate with vinculin, IpaA VBS3 acts as a TBS.

Talin is Needed for Efficient *Shigella* Invasion of Epithelial Cells.

In previous works, we established the role of vinculin and IpaA in *Shigella* invasion (Izard et al., 2006; Tran Van Nhieu et al., 2007; Park et al., 2011). Our results suggest that talin is also a major target of IpaA, in association with vinculin. To test the role of talin during *Shigella* invasion, we first analyzed its recruitment at sites of bacterial entry. As shown in FIGS. 11A and 11B, talin could be detected at bacterial sites in ruffles surrounding the bacteria, as early as 5 minutes following challenge. As bacterial internalization proceeded, talin was enriched at actin-rich membrane extensions extending at the bacterial vicinity. Rapidly, however, talin recruitment was detected at the intimate bacterial-cell contact site to form coat-like structures around internalized bacteria (FIG. 11A, arrowhead). The formation of these coat-like structures, referred to in previous works as focal-adhesion like structures (Tran Van Nhieu et al., 2007), occurred concomitantly with actin depolymerization in membrane ruffles upon completion of the bacterial internalization process and was virtually detected in all foci at 30 minutes post-challenge.

To evaluate the importance of talin in *Shigella* invasion, cells were transfected with anti-talin siRNA prior to bacterial challenge. Upon talin inhibition, the frequency of actin foci formation per cell was not significantly different from control cells, but the dynamics of bacterial induced actin polymerization at invasion sites were drastically altered. While in control cells, completion of bacterial invasion was associated with actin depolymerization and formation of coat structures, such structures did not form in anti-talin siRNA treated cells and actin foci still expanded after 20 minutes of bacterial challenge (FIGS. 11C and 11F). Strikingly, upon talin inhibition, actin polymerization did not appear proficient for bacterial invasion, with bacteria remaining associated at the periphery of actin foci (FIGS. 11C and 11D). As shown in FIGS. 11D and 11E, the percentage of internalized bacteria was reduced by ca. 10-fold in anti-talin siRNA treated cells compared to control cells. When cells were challenged with a *Shigella* IpaA mutant, as previously reported, a ca. 10-fold decrease in bacterial internalization was observed in control cells (Izard T. et al., 2006).

To investigate the role of IpaA domains in talin recruitment, cells were challenged with ipaA mutant strains, complemented with IpaA construct derivatives. Consistent with the role of IpaA and IpaA VBS1/3 in talin recruitment, coat structures were not detected for the ipaA mutant strain, or the ipaA mutant strain complemented with IpaA N terminal domain deleted for its C-terminal VBS1/3, as opposed to WT *Shigella* (FIGS. 11G and 11H). Complementation of the ipaA mutant strain with IpaAΔ550-633, containing only VBS3, or IpaAΔ489-511 containing only VBS1/2, partially trigger talin recruitment at the site of intimate bacterial-cell contact and coat-structure formation but less frequently compared to full length IpaA (FIGS. 11G and 11H). These results are consistent with a redundant role for IpaA VBS1/2 and IpaA VBS3/TBS and underline the importance of vinculin-talin scaffolds during *Shigella* invasion.

Figure 17:
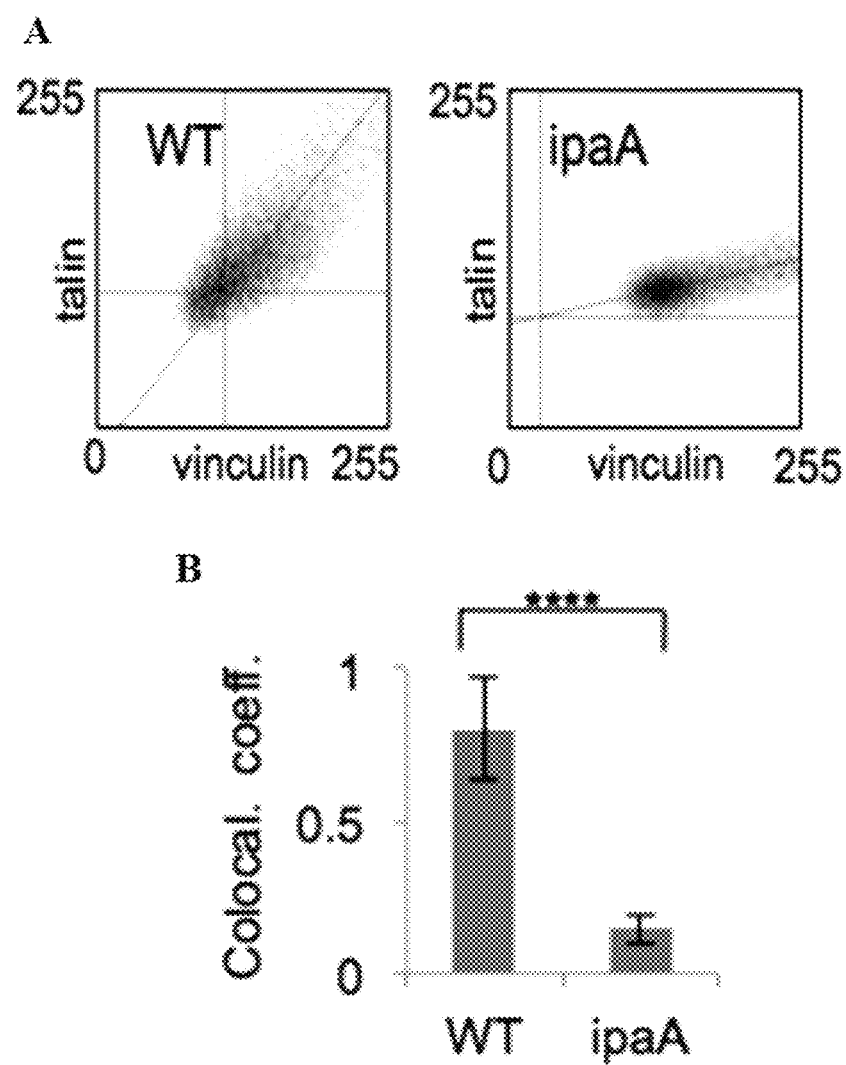
FIG. 17 is a set of graphs showing that talin is required for IpaA-dependent *Shigella* anchoring to actin foci and invasion. A, Talin-GFP and vinculin-mCherry transfected cells challenged with *Shigella* strains. Representative scatter plots are showing the intensity correlation of pixels with vinculin and talin co-localization at bacterial coats for WT and IpaA mutant strains. B, The median of the regression coefficient of the intensity of talin and vinculin at bacterial entry foci (n(WT)=33 and n(IpaA)=18) were measured as 0.80±0.16 and 0.14±0.04 respectively, and compared using a Wilcoxon rank sum test (p-value=5×10$^{-9}$, ****).

A strong correlation in recruitment of talin and vinculin was observed at actin structures coating WT *Shigella*. The correlation in the intensity of talin-vinculin co-localization was observed throughout the coat structures for WT *Shigella*, but not the IpaA mutant (FIGS. 17A and 17B).

Figure 18:
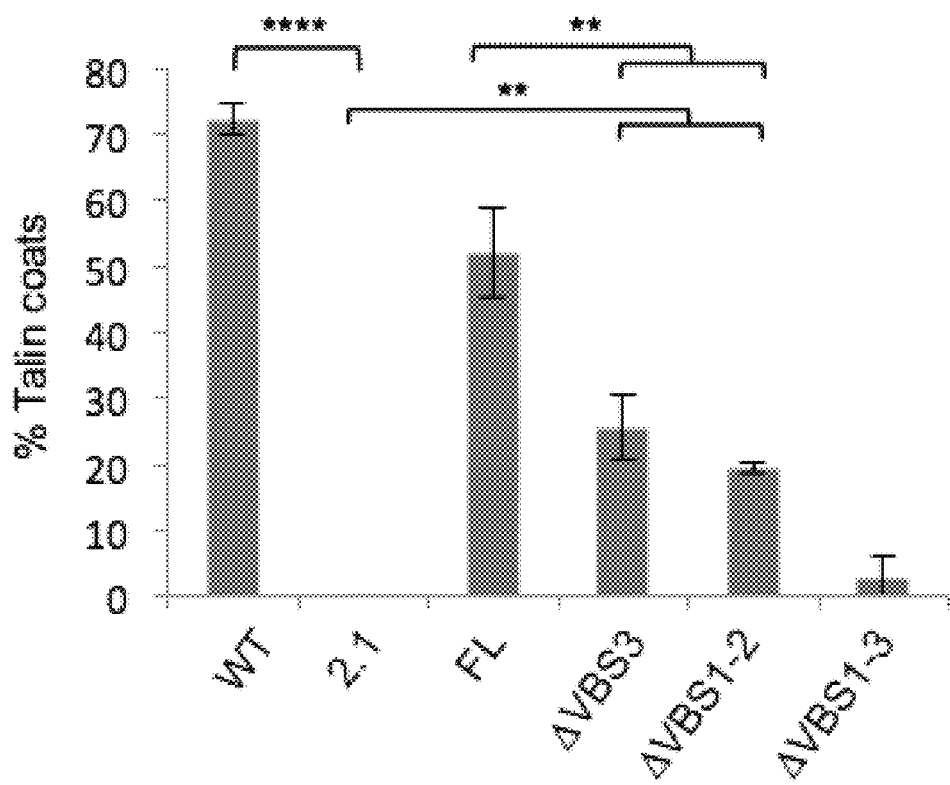
FIG. 18 is a graph showing the role of IpaA VBSs in talin and vinculin recruitment during *Shigella* invasion. HeLa cells were transfected with talin-GFP and challenged with *Shigella* strains for 30 minutes at 37° C. Cells challenged with the IpaA mutant strain complemented with full length IpaA (FL), vector alone (2.1), IpaAΔVBS3 and IpaAΔVBS1-2. The arrows point at talin coat structures surrounding invading bacteria. Scale bar=5 μm. Average percentage of actin foci forming talin-coat structures induced by the indicated bacterial strain±SD (Exp. Procedures). For each samples, n>35 foci in at least three independent experiments. Chi-squared test with post-hoc comparison (FDR correction for p-value).

To investigate the role of IpaA domains in the formation of talin coat structures forming at the intimate bacterial-cell contact, cells were challenged with ipaA mutant strains complemented with different IpaA derivatives. Talin "coat" structures were detected for WT *Shigella* or the ipaA mutant strain complemented with gene encoding full length IpaA, but not for ipaA mutant strains complemented with vector alone (2.1) or with gene encoding IpaA deleted for its VBS1/3 (ΔVBS1-3) (FIG. 18). Complementation of the ipaA mutant strain with genes encoding full length IpaA, IpaAΔVBS1/2 or IpaAΔVBS3, restored the formation of foci with talin coat structures. However, a significant decrease in the percentage of foci forming talin coat structures was observed for ipaA mutant strains expressing IpaAΔVBS1/2 or IpaAΔVBS3 compared to full length IpaA, with 19±0.7% and 25±5% relative to 52±6.7%, respectively (FIG. 18).

These results are consistent with a joint role for IpaA VBS1/2 and IpaA VBS3/TBS in talin/vinculin recruitment and underline the importance of multiple interactions with cytoskeletal linkers during *Shigella* invasion.

Example 3: A483 Induces Vinculin Supra-Activation and Cell Adhesion in the Absence of Mechanosension A483 Increases the Rate of Force Generation and Cell Adhesion Strength.

To quantify the effects of vinculin supra-activation on the strength of traction forces and cell adhesion, we used a parallel-plates technique (FIG. 19A) allowing one to measure the traction forces generated by single cells, while simultaneously monitoring focal adhesions (FAs)' growth, as previously described (Fouchard et al., 2014. *PNAS*). It can also be used to apply traction forces to the cell in order to measure the adhesion strength.

Figure 19:
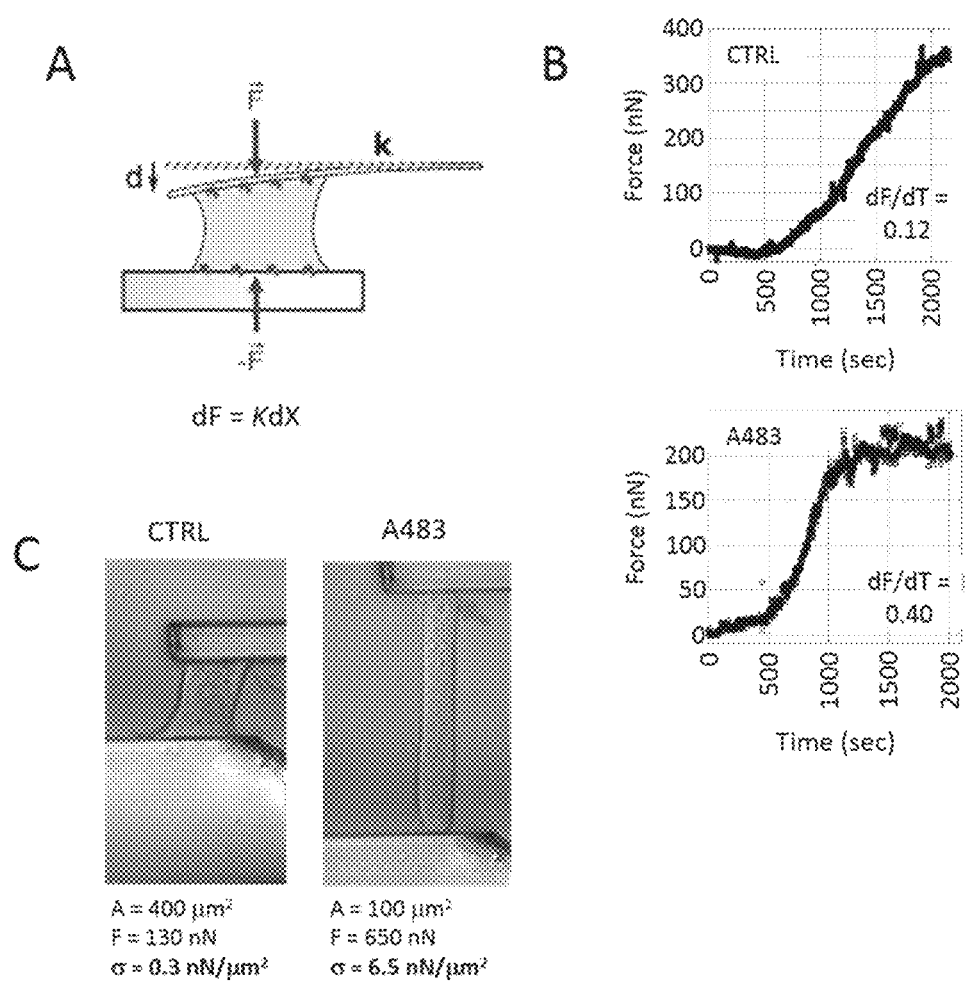
FIG. 19 is a set of graphs and schemes showing that A483 increases the rate of force generation and cell adhesion strength. A, The parallel plates setup: the traction force (F) generated by a single cell is monitored by the deflection (d) of the flexible microplate of calibrated stiffness (k). The flexible microplate can also be used to pull on the cell to test its adherence to the plates. B, Representative traces showing single-cell traction forces as a function of time. CTRL: control cells; IpaA-VBD: GFP-A483 transfectants. The rates (dF/dt) were measured as 0.12 and 0.40 for control cells and GFP-A483 transfectants, respectively, indicating faster force generation in GFP-A483 transfectants. C, The force F (in nN) and contact area A (arrow, in μm$^2$) at detachment are recorded to determine the "adhesion stress" σ=F/A. σ=0.3 and 6.5 nN/μm$^2$ for control cells and GFP-A483 transfectants, respectively, indicating an increased cell adhesion strength in GFP-A483 transfectants.

Our preliminary results indicate that, under the parameters used, A483 accelerates the kinetics of force generation (FIG. 19B), and clearly increases the maximum stress before detachment, e. g. the adhesion strength (FIG. 19C).

IpaA-VBD Enhances Vinculin-Mediated Cell Adhesion in the Absence of Mechanosensing.

To confirm this latter result at the scale of a whole cell population, we performed assays where cells, resuspended by trypsinization, were allowed to adhere for define amounts of time on Fn-coated substrates before washing. Then the number of cells that remained attached to the substrate was measured.

Figure 20:
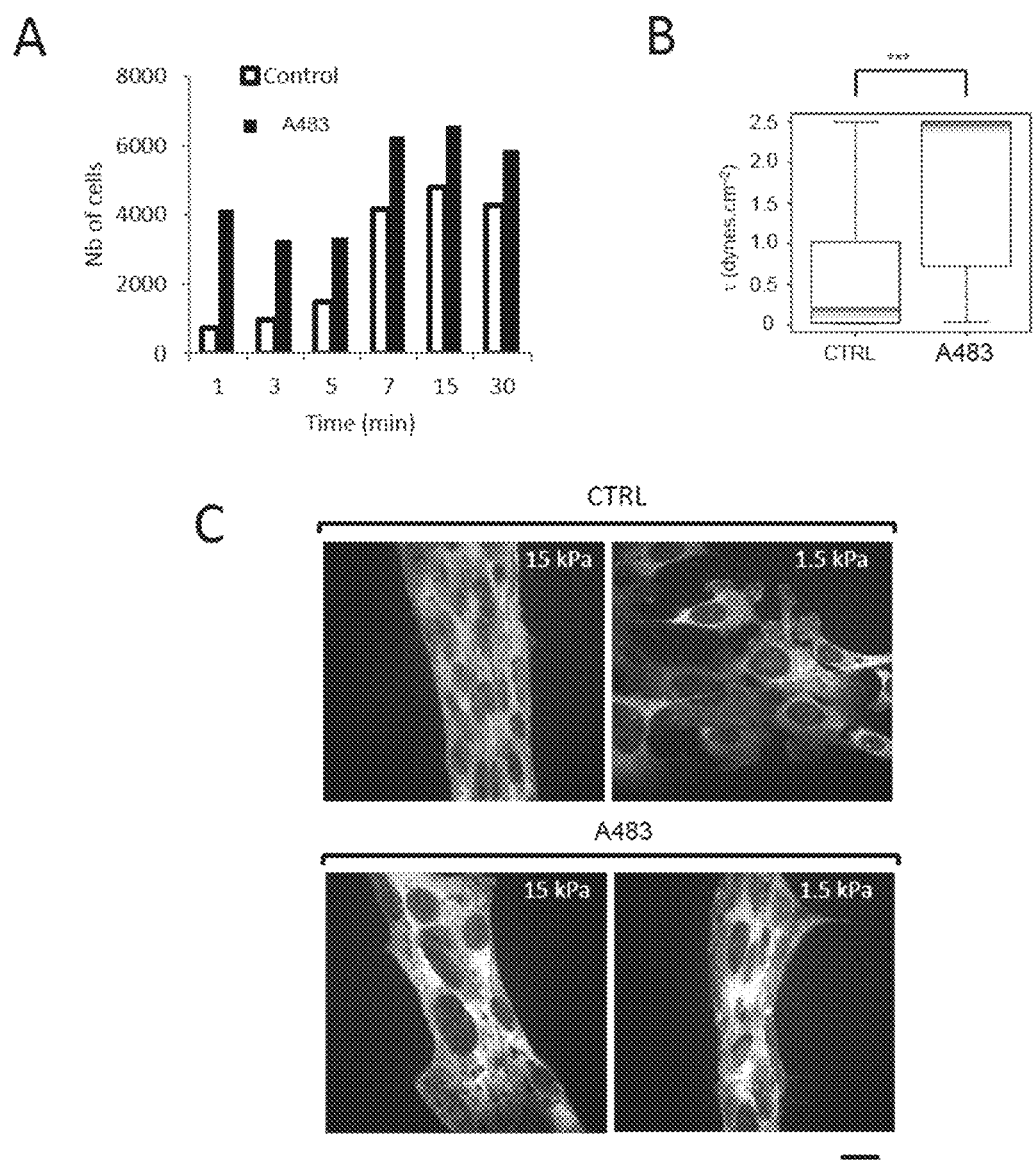
FIG. 20 is a set of graphs and images showing that A483 enhances vinculin-mediated cell adhesion in the absence of mechanosensing. A, Suspended cells were incubated for the indicated time with fibronectin-coated wells prior to washing. The number of adherent cells is indicated. B, Cells were perfused in a microfluidic chamber and allowed to adhere for 1 minute prior to shear stress application. Boxplot of the median resistance to shear stress for control (34 cells, N=2) and GFP-A483 (15 cells, N=1). ***: p=0.00039. C, Cells were plated on fibronectin-coated PDMS membranes with the indicated stiffness. Note the formation of myotubes in A483 transfectants at low substrate stiffness. CTRL: control cells; IpaA-VBD: GFP-A483 transfectants.

As previously observed, A483 induced the formation of large adhesion structures in C2.7 cells (FIG. 20A). While A483 transfectants induced a spectacular 5.6-fold increase in the number of adherent cells after 60 seconds of incubation, this increase was reduced to 1.3-fold when adhesion was tested after 30 min. These findings were quantified by measuring the resistance to shear stress of cells under flow as a function of the incubation time with the substrate in microfluidic chambers (FIG. 20B). Thus, through its direct binding via IpaA VBS3/TBS or indirect unveiling of binding sites on vinculin "supra-activated", A483 may "by-pass" mechanosensing normally associated with the initial steps of cell adhesions' formation. While we cannot rule out the possibility that A483 induces an original ex-nihilo adhesion structure, our current results rather argue that it allows the bypassing of actomyosin-dependent mechanosensing steps that would lead to vinculin supra-activation at high actomyosin contraction forces. To further test this, we plated the C2.7 myoblastic cells on various fibronectin-coated PDMS membranes showing different stiffness. As expected, at low substrate stiffness (1.5 kPa), control cells remained spread and isolated, whereas at high substrate stiffness (15 kPa), cells differentiated into myotubes (FIG. 20C). Strikingly, however, A483 expressing cells formed myotubes not only at high, but also at low substrate stiffness, consistent with bypassing of mechanosensing. Indeed, while A483 expressing cells show increased FAs' extension and adhesion, preliminary results indicate no difference in force generation between control and A483 cells.

These results indicate thus the by-passing of actomyosin-dependent mechanosensing steps, even on low-stiffness substrates, suggesting an efficient role of A483 in the treatment of metastasis and other soft-tissue cancers.

Effects of A483-Mediated Vinculin Supra-Activation on Adhesion Structure Composition and Dynamics.

Focal adhesion (FA) markers such as FAK, paxillin and vinculin are associated with nascent adhesions while VASP, a-actinin or zyxin are characteristic of mature FAs (FIG. 22). The kinetics and hierarchy of disappearance of these markers following actomyosin relaxing drugs are in good agreement with the recruitment of these markers during FA maturation as a result of increased traction forces. Following MAPK-dependent phosphorylation, however, zyxin has been shown to redistribute to stress fibers, along with VASP and α-actinin, and promote their stabilization. The identification of markers recruited by supra-active vinculin at FA will provide with information on whether A483 bypasses mechanosensing steps or generates a specific adhesion structure. Beyond cell adhesion, FA components have been involved in various processes including signaling linked to cell proliferation, cell death as well as inflammation.

Vinculin activation depending on actomyosin contraction was shown to be required for the scaffolding of mature FA markers. However, FA markers appear to differ in their requirements for vinculin-dependent recruitment, since upon drug-based actin relaxation experiments, some like vinexin and ponsins are stabilized by active mutant forms of vinculin deficient for HVD1-tail interaction, while others like α-actinin are not. The reason for these differences are not known, but in lights of evidence for vinculin supra-activation, it is possible that the recruitment of some of these FA markers is directly mediated by vinculin domains other than HVD1 specifically exposed on the supra-active form of vinculin.

Figure 21:
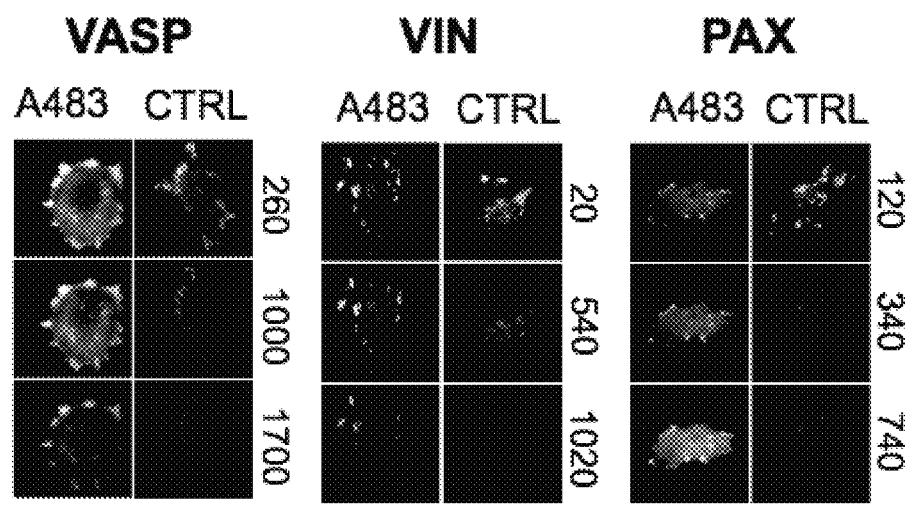
FIG. 21 is a set of images showing that IpaA prevents the disassembly of focal adhesions induced by the relaxation of the actomyosin contraction. MEF cells were transfected with focal adhesion proteins Paxillin-Cherry (PAX), Vinculin-Cherry (VIN) or VASP-Cherry (VASP). CTRL: single transfection; A483: cells were co-transfected with GFP-A483. The intensity of focal adhesion proteins (visualized as white dots) is shown at the indicated time points in seconds after the addition of the ROCK inhibitor Y-27632 by TIRF microscopy. A483 prevents the destabilization of FA markers induced by the ROCK inhibitor observed in control cells.

In preliminary experiments, we have analyzed the role of actomyosin contraction on the recruitment of FA markers linked to the supra-activation of vinculin, by treating cells with the Rho-kinase inhibitor Y-27632. The disappearance of markers from FAs was analyzed following in real-time using total internal reflection (TIRF) microscopy. As shown in FIG. 21, A483 transfection led to a stabilization of all FA markers studied compared to control cells. Strikingly, VASP, a marker of mature FAs, was also stabilized by A483, while previous studies had shown that this FA marker was not stabilized by active vinculin, deficient for head-tail intramolecular interaction.

Together, these experiments support the notion that A483 promotes the establishment of stable FAs in the absence of acto-myosin contraction required for mechanosensing and reinforce the efficient use of A483 in the treatment of cancers, including soft-tissue cancers.

Example 4: A483 Inhibits Melanocytes Migration and Matrigel Invasion

Cells were transfected by GFP-A524, GFP-A483 or Mock-transfected (without DNA, as a control).

Figure 24:
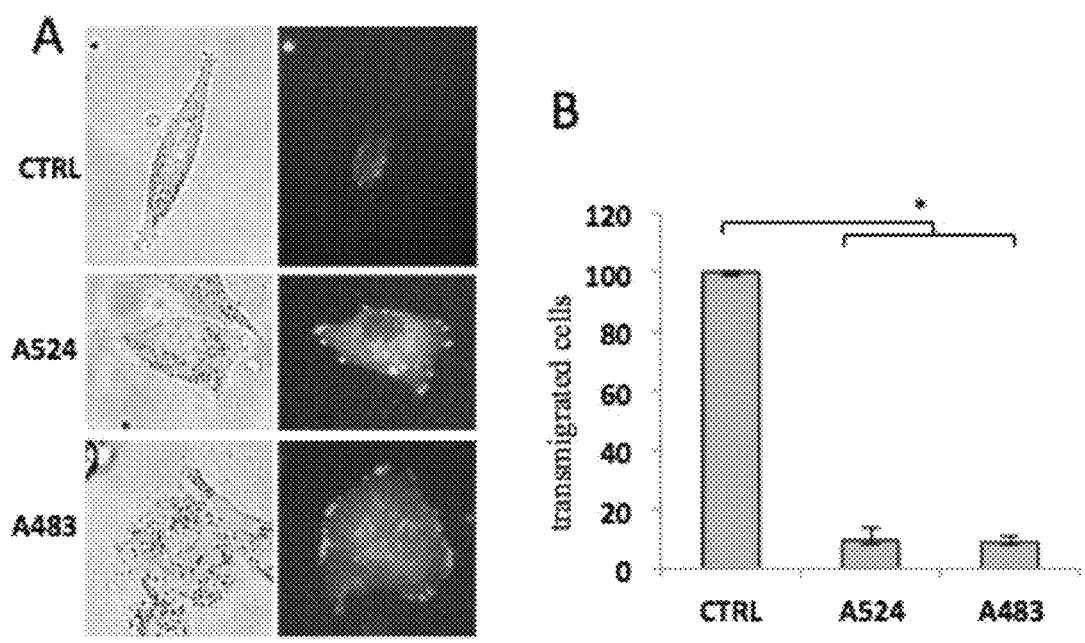
FIG. 24 is a set of micrographs and graph, showing the inhibition of melanocytes migration and matrigel invasion upon transfection with A483 or A524. A, Representative micrographs of melanocytes after transfection with A483, A524 or Mock-transfection (CTRL), showing the spread of A483 and A524-transfected cells. The transfection efficacy is estimated to about 20-30%, as scored by GFP fluorescence. B, Number of cells which migrated across a matrigel, for A483-, A524- and Mock (CTRL)-transfected melanocytes. The graph clearly indicates a strong inhibitory effect of both A483 and A524 on the migration of these melanocytes. Results are expressed as the average percentage SD relative to control cells of three independent experiments. CTRL: 1232 cells, A524: 96 cells; A483: 120 cells. Dunn rank test (*: p<0.025).

After transfection, control cells show a typical fusiform shape. A524- and A483-cells however were more spread, with both transfected constructs labeling peripheral adhesion structures (FIG. 24A).

Cells were further trypsinized, collected, and deposited in a matrigel insert. Following a 24-hour incubation, the matrigel was remove, the membrane was fixed and processed for fluorescence straining of cell nuclei with DAPI. Cells that transmigrated across the matrigel were scored (FIG. 24B). In despite of the 20-30% levels of transfection estimated from the scoring of GFP fluorescence for both A483 and A524 in FIG. 24A, the inhibition of cell migration in matrigel invasion assays associated with the constructs reached up to 90%.

Without willing to be bound by a theory, the Applicant suggests that this discrepancy could be explained by the underestimation of the actual levels of transfectants, combined with an inhibitory effect of these constructs on cell replication.

Preliminary experiments from the analysis of 6 movies for each sample in time lapse experiments indicate that the transfection of A483 shows a strong effect on cell migration. Remarkably, transfection with GFP-A524 did not drastically alter the motility of melanocytes. In these experiments, however, long term incubation (6 hours) were associated with a significant fraction of cells rounding up in the A524 and A483 transfected cells, suggesting a general stress on the cell fitness linked to the combine effects of the constructs and imaging parameters.

The invention claimed is:

1. A polypeptide comprising the three following vinculin binding sites (VBS):

VBS1: IYKAAKDVTTSLSKVLKNI (SEQ ID NO: 2) or a variant thereof, wherein the variant of SEQ ID NO: 2 is a polypeptide having a sequence identity of at least 90% with SEQ ID NO: 2;

VBS2: IYEKAKEVSSALSKVLSKI (SEQ ID NO: 3) or a variant thereof, wherein the variant of SEQ ID NO: 3 is a polypeptide having a sequence identity of at least 90% with SEQ ID NO: 3; and VBS3: IFEASKKVTNSLSNLISLI (SEQ ID NO: 4) or a variant thereof, wherein the variant of SEQ ID NO: 4 is a polypeptide having a sequence identity of at least 90% with SEQ ID NO: 4;

wherein said polypeptide consists of 140 to 160 amino acids and wherein said polypeptide is not cytotoxic upon cell transfection as compared to the full-length invasion plasmid antigen A (IpaA) protein of SEQ ID NO:1.

2. The polypeptide according to claim 1, wherein said polypeptide is SEQ ID NO: 5 or a variant thereof, wherein the variant of SEQ ID NO: 5 is a polypeptide having a sequence identity of at least 90% with SEQ ID NO: 5.

* * * * *